US009044460B2

(12) United States Patent
Bukhalid et al.

(10) Patent No.: US 9,044,460 B2
(45) Date of Patent: Jun. 2, 2015

(54) ANTIBODIES AGAINST EPIDERMAL GROWTH FACTOR RECEPTOR (EGFR) AND USES THEREOF

(75) Inventors: Raghida Bukhalid, Melrose, MA (US); Michael Feldhaus, Grantham, NH (US); Anne King, Cambridge, MA (US); Neeraj Kohli, Brighton, MA (US); Eric Krauland, Lebanon, NH (US); Ulrik Nielsen, Quincy, MA (US)

(73) Assignee: Merrimack Pharmaceuticals, Inc., Cambridge, MA (US)

( * ) Notice: Subject to any disclaimer, the term of this patent is extended or adjusted under 35 U.S.C. 154(b) by 756 days.

(21) Appl. No.: 13/100,920

(22) Filed: May 4, 2011

(65) Prior Publication Data
US 2011/0287002 A1    Nov. 24, 2011

Related U.S. Application Data

(60) Provisional application No. 61/331,093, filed on May 4, 2010.

(51) Int. Cl.
*A61K 39/395* (2006.01)
*C07K 16/28* (2006.01)
*A61K 39/00* (2006.01)

(52) U.S. Cl.
CPC ..... *A61K 39/39558* (2013.01); *A61K 2039/507* (2013.01); *C07K 2317/34* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| 7,226,592 | B2 | 6/2007 | Kreysch |
| 7,498,142 | B2 | 3/2009 | Yarden et al. |
| 7,771,958 | B2 | 8/2010 | Bacus et al. |
| 7,887,805 | B2 | 2/2011 | Pedersen et al. |
| 8,414,896 | B2 | 4/2013 | Pedersen et al. |
| 8,830,814 | B2 | 9/2014 | Manakkal et al. |
| 2004/0052785 | A1 | 3/2004 | Goodman et al. |
| 2005/0003403 | A1 | 1/2005 | Rossi et al. |
| 2006/0228355 | A1 | 10/2006 | Laeremans et al. |
| 2008/0206236 | A1 | 8/2008 | Haurum |
| 2008/0299120 | A1 | 12/2008 | Miller et al. |
| 2009/0004192 | A1 | 1/2009 | Pedersen et al. |
| 2009/0155288 | A1 | 6/2009 | Yarden et al. |
| 2009/0226447 | A1* | 9/2009 | Boone et al. ............. 424/139.1 |
| 2011/0287002 | A1 | 11/2011 | Bukhalid et al. |
| 2014/0127207 | A1 | 5/2014 | Bukhalid et al. |
| 2014/0170668 | A1 | 6/2014 | Bukhalid et al. |
| 2014/0234314 | A1 | 8/2014 | Bukhalid et al. |

FOREIGN PATENT DOCUMENTS

| CN | 101675075 | | 3/2010 |
| WO | 02/055106 | A2 | 7/2002 |
| WO | 2004/032961 | A1 | 4/2004 |
| WO | 2004/094613 | A2 | 11/2004 |
| WO | 2008/095504 | A1 | 8/2008 |
| WO | 2008/104183 | A2 | 9/2008 |
| WO | WO2009/030239 | * | 3/2009 |
| WO | 2010/019952 | A2 | 2/2010 |
| WO | 2011/140151 | A1 | 11/2011 |
| WO | 2011/140254 | A1 | 11/2011 |

OTHER PUBLICATIONS

International Preliminary Report on Patentability for Application No. PCT/US2011/035238, 7 pages, dated Nov. 6, 2012.
ClinicalTrials.gov, "A Phase I Study of Cetuximab in Combination With Gefitinib in Patients With Advanced/Metastatic Non-Small Cell Lung Cancer," Study NCT00162318, Bristol-Myers Squibb, 3 pages, date received Sep. 9, 2005.
ClinicalTrials.gov, "A Study of BIBW 2992 (Afatinib) in Patients With Metastatic Colorectal Cancer," Study NCT01152437, Boehringer Ingelheim Pharmaceuticals, 4 pages, date received Jun. 28, 2010.
ClinicalTrials.gov, "A Study of R1507 in Combination With Multiple Standard Chemotherapy Treatments in Patients With Advanced Solid Tumors," Study NCT00811993, Hoffmann-La Roche, 6 pages, dated received Dec. 18, 2008.
ClinicalTrials.gov, "A Study of SCH 717454 in Combination With Different Treatment Regimens in Subjects With Advanced Solid Tumors (P04722)," Study NCT00954512, Schering-Plough, 5 pages, dated received Jul. 23, 2009.
ClinicalTrials.gov, "An Umbrella, Modular Study Based on Epidermal Growth Factor Receptors (EGFR) Mutation Status," Study NCT00903734, M.D. Anderson Cancer Center, 5 pages, dated received May 14, 2009.
ClinicalTrials.gov, "Bevacizumab in Multiple Phase I Combinations," Study NCT00543504, M.D. Anderson Cancer Center, 7 pages, dated received Oct. 11, 2007.
ClinicalTrials.gov, "Bevacizumab and Gemcitabine Combined With Either Cetuximab or Erlotinib in Treating Patients With Advanced Pancreatic Cancer," Study NCT00091026, National Cancer Institute (NCI), 6 pages, dated received Sep. 7, 2004.
ClinicalTrials.gov, "BIBW 2992 (Afatinib) in Head & Neck Cancer," Study NCT00514943, Boehringer Ingelheim Pharmaceuticals, 5 pages, dated received Aug. 9, 2007.
ClinicalTrials.gov, "Carboplatin, Paclitaxel, Cetuximab, and Erlotinib Hydrochloride in Treating Patients With Metastatic or Recurrent Head and Neck Squamous Cell Cancer," Study NCT01316757, Fox Chase Cancer Center, 7 pages, Mar. 8, 2011.
ClinicalTrials.gov, "Cetuximab in Patients With Lung Adenocarcinoma Receiving Erlotinib That Have Developed 'Acquired Resistance' to Erlotinib," Study NCT00716456, Memorial Sloan-Kettering Cancer Center, 1 page, dated received Jul. 15, 2008.
ClinicalTrials.gov, "Clinical and Pathologic Studies of Patients Undergoing Treatment With EGFR Inhibitors," Study NCT01137162, Stanford University, 1 page, dated received Jun. 1, 2010.
ClinicalTrials.gov, "Combination Study of BMS-754807 and Erbitux in Subjects With Advanced or Metastatic Solid Tumors," Study NCT00908024, Bristol-Myers Squibb, 4 pages, dated received May 22, 2009.

(Continued)

Primary Examiner — Karen Canella
(74) *Attorney, Agent, or Firm* — Nelson Mullins Riley & Scarborough LLP; Jane E. Remillard, Esq.; Jill Gorny Sloper, Esq.

(57) ABSTRACT

Anti-EGFR antibodies, therapeutic compositions comprising combinations of anti-EGFR antibodies, as well as methods for using such antibodies and compositions to treat EGFR-related disorders (e.g., cancers), are disclosed.

12 Claims, 16 Drawing Sheets

(56) References Cited

OTHER PUBLICATIONS

ClinicalTrials.gov, "Dual Epidermal Growth Factor Receptor Inhibition With Erlotinib and Panitumumab With or Without Chemotherapy for Advanced Colorectal Cancer," Study NCT00940316, Northwestern University, 1 page, dated received Jul. 15, 2011.

ClinicalTrials.gov, "Dual Inhibition of EGFR Signalling Using the Combination of Cetuximab and Erlotinib (Dux)," Study NCT00784667, Austin Health, 1 page, dated received Nov. 3, 2008.

ClinicalTrials.gov, "Erlotinib and Cetuximab With or Without Bevacizumab in Treating Patients With Metastatic or Unresectable Kidney, Colorectal, Head and Neck, Pancreatic, or Non-Small Cell Lung Cancer," Study NCT00101348, National Cancer Institute (NCI), 6 pages, dated received Jan. 7, 2005.

ClinicalTrials.gov, "Erlotinib and Cetuximab in Treating Patients With Advanced Gastrointestinal Cancer, Head and Neck Cancer, Non-Small Cell Lung Cancer, or Colorectal Cancer," Study NCT00397384, Vanderbilt-Ingram Cancer Center, 1 page, dated received Nov. 8, 2006.

ClinicalTrials.gov, "Erlotinib and Cetuximab in Treating Patients With Advanced Solid Tumors With Emphasis on Non-Small Cell Lung Cancer," Study NCT00408499, University of California, Davis, 1 page, dated received Dec. 6, 2006.

ClinicalTrials.gov, "Erlotinib and Gemcitabine With or Without Panitumumab in Treating Patients With Metastatic Pancreatic Cancer," Study NCT00550836, National Cancer Institute (NCI), 6 pages, dated received Oct. 26, 2007.

ClinicalTrials.gov, "Erlotinib in Combination With Cetuximab," Study NCT00895362, M.D. Anderson Cancer Center, 5 pages, dated received May 6, 2009.

ClinicalTrials.gov, "Evaluating Preventive Therapy With Oint Threolone, Synthomycine or Aqua Cream Lotion, for EGFR'l Induced Acneiform Rash," Study NCT01256437, Rabin Medical Center, 4 pages, dated received Dec. 7, 2010.

ClinicalTrials.gov, "Histological Characterization and Differentiation of Rash From Other Epidermal Growth Factor Receptor (EGFR) Inhibitors," Study NCT00709878, Northwestern University, 1 page, dated received Jul. 1, 2008.

ClinicalTrials.gov, "Individualized Drug Treatment Selection Process for Treating Patients with Pancreatic Cancer That Can Be Removed by Surgery," Study NCT00276744, Sidney Kimmel Comprehensive Cancer Center, 5 pages, dated received Jan. 12, 2006.

ClinicalTrials.gov, "Lapatinib and Cetuximab in Patients With Solid Tumors (TYKERB-ITUX 1)," Study NCT01184482, Georgetown University, 4 pages, dated received Aug. 17, 2010.

ClinicalTrials.gov, "Menadione Topical Lotion in Treating Skin Discomfort and Psychological Distress in Patients With Cancer Receiving Panitumumab, Erlotinib Hydrochloride, or Cetuximab," Study NCT01393821, Mayo Clinic, 5 pages, dated received Jun. 27, 2011.

ClinicalTrials.gov, "Pharmocokinetic/Pharmacodynamic (PK/PD) Study of the Combination Cetuximab/Gefitinib," Study NCT00820417, Harrison Clinical Research, 1 page, dated received Jan. 9, 2009.

ClinicalTrials.gov, "Pharmacodynamic Separation of Pemetrexed and Erlotinib as Second-line Therapy in Patients With Advanced Non-small Cell Lung Cancer (NSCLC)," Study NCT00950365, Montefiore Medical Center, 1 page, dated received Jul. 30, 2009.

ClinicalTrials.gov, "Phase 1 Trial With SIR-Spheres and Cetuximab +/− Erlotinib," Study NCT01432119, M.D. Anderson Cancer Center, 6 pages, dated received Sep. 8, 2011.

ClinicalTrials.gov, "Safety and Efficacy of Radiation/Cetuximab Plus EGFR Antisense DNA for Head and Neck Squamous Cell Carcinoma," Study NCT00903461, University of Pittsburgh, 5 pages, dated received May 14, 2009.

ClinicalTrials.gov, "Study About Preventive Treatment of Folliculitis Induced by Epidermal Growth Factor Receptor (EGF-R) Inhibitors (DIPROCOL)," Study NCT00910676, Centre Oscar Lambret, 4 pages, dated received May 29, 2009.

ClinicalTrials.gov, "Study of AMG 479 With Biologics or Chemotherapy for Subjects With Advanced Solid Tumors," Study NCT00974896, Amgen, 5 pages, dated received Sep. 10, 2009.

ClinicalTrials.gov, "Study of Cetuximab in Combination With Tarceva in Patients With Solid Tumors," Study NCT00207077, Bristol-Myers Squibb, 3 pages, dated received Sep. 12, 2005.

ClinicalTrials.gov, "Sym004 in Patients With Advanced Solid Tumors," Study NCT01117428, Symphogen A/S, 1 page, dated received Apr. 23, 2010.

ClinicalTrials.gov, "Sym004 in SCCHN Patients Failing Anti-EGFR Based Therapy," Study NCT01417936, Symphogen A/S, 1 page, dated received Jul. 15, 2011.

ClinicalTrials.gov, "Temsirolimus (Torisel) and Erlotinib (Tarceva) in Platinum-Refractory/Ineligible, Advanced, Squamous Cell Carcinoma," Study NCT01009203, New Mexico Cancer Care Alliance, 4 pages, dated received Nov. 5, 2009.

ClinicalTrials.gov, "Tetracycline in Preventing Skin Rash in Patients Who Are Receiving Drugs Such as Gefitinib and Cetuximab for Cancer," Study NCT00091247, National Cancer Institute (NCI), 1 page, dated received Sep. 7, 2004.

ClinicalTrials.gov, "Topical Sunscreen in Preventing Skin Rash in Patients Receiving Drugs Such as Erlotinib or Cetuximab for Cancer," Study NCT00362986, National Cancer Institute (NCI), 4 pages, dated received Aug. 10, 2006.

ClinicalTrials.gov, "Trial of BIBW 2992 (Afatinib) + Cetuximab in Non-Small Cell Lung Cancer," Study NCT01090011, Boehringer Ingelheim Pharmaceuticals, 1 page, dated received Mar. 10, 2010.

ClinicalTrials.gov, "Validation of Cancer Questionnaire for Skin Toxicities in Patients With Colorectal Cancer or Lung Cancer Receiving Cetuximab, Panitumumab, or Erlotinib Hydrochloride," Study NCT01416688, National Cancer Institute (NCI), 5 pages, dated received Aug. 12, 2011.

ClinicalTrials.gov, "ZD6474, Cetuximab, and Irinotecan in Patients With Metastatic Colorectal Cancer," Study NCT00436072, Dana-Farber Cancer Institute, 5 pages, dated received Feb. 15, 2007.

Fogler, William E. et al., "Enhanced Cytotoxicity against Colon Carcinoma by Combinations of Noncompeting Monoclonal Antibodies to the 17-1A Antigen," Cancer Research, vol. 48:6303-6308 (1988).

Friedman, Lilach M. et al., "Synergistic down-regulation of receptor tyrosine kinases by combinations of mAbs: Implications for cancer innumotherapy," PNAS, vol. 102(6):1915-1920 (2005).

Kamat, Vishal et al., "Enhanced EGFR inhibition and distinct epitope recognition by EGFR antagonistic mAbs C225 and 425," Cancer Biology & Therapy, vol. 7(5):726-733 (2008).

Nahta, Rita et al., "The HER-2-Targeting Antibodies Trastuzumab and Pertuzumab Synergistically Inhibit the Survival of Breast Cancer Cells," Cancer Research, vol. 64:2343-2346 (2004).

Nowakowski, A. et al., "Potent neutralization of botulinum neurotoxin by recombinant oligoclonal antibody," PNAS, vol. 99(17):11346-11350 (2002).

Pedersen, Mikkel Wandahl et al., "Sym004: A Novel Synergistic Anti-Epidermal Growth Factor Receptor Antibody Mixture with Superior Anticancer Efficacy," Cancer Research, vol. 70(2):588-597 (2010).

Perera, Rushika M. et al., "Treatment of Human Tumor Xenografts with Monoclonal Antibody 806 in Combination with a Prototypical Epidermal Growth Factor Receptor-Specific Antibody Generates Enhanced Antitumor Activity," Clinical Cancer Research, vol. 11(17):6390-6399 (2005).

Regales, Lucia et al., "Dual targeting of EGFR can overcome a major drug resistance mutation in mouse models of EGFR mutant lung cancer," The Journal of Clinical Investigation, vol. 119(10):3000-3010 (2009).

Skartved, Niels Jorgen Ostergaard et al., "Preclinical Pharmacokinetics and Safety of Sym004: A Synergistic Antibody Mixture Directed against Epidermal Growth Factor Receptor," Clinical Cancer Research, vol. 17 (18):5962-5972 (2011).

Spangler, Jamie B. et al., "Combination antibody treatment down-regulates epidermal growth factor receptor by inhibiting endosomal recycling," PNAS, vol. 107(30):13252-13257 (2010).

Spiridon, Camelia I. et al., "Targeting Multiple Her-2 Epitopes with Monoclonal Antibodies Results in Improved Antigrowth Activity of a Human Breast Cancer Cell Line in Vitro and in Vivo," Clinical Cancer Research, vol. 8:1720-1730 (2002).

(56) References Cited

OTHER PUBLICATIONS

Baker, J.B. et al., "Tumour gene expression predicts response to cetuximab in patients with KRAS wild-type metastatic colorectal cancer," British Journal of Cancer, vol. 104:488-495 (2011).

Cochran, Jennifer R. et al., "Domain-level antibody epitope mapping through yeast surface display of epidermal growth factor receptor fragments," Journal of Immunological Methods, vol. 287:147-158 (2004).

Grandis, Jennifer Rubin et al., "Levels of TGF-alpha and EGFR Protein in Head and Neck Squamous Cell Carcinoma and Patient Survival," Journal of the National Cancer Institute, vol. 90(11):824-832 (1998).

Hatakeyama, Hiromitsu et al., "Regulation of Heparin-Binding EGF-Like Growth Factor by MiR-212 and Acquired Cetuximab-Resistance in Head and Neck Squamous Cell Carcinoma," PLoS ONE, vol. 5(9):e12702, 1-13 (2010).

Modjtahedi, H. et al., "Antitumor Activity of Combinations of Antibodies Directed Against Different Epitopes on the Extracellular Domain of the Human EGF Receptor," Cell Biophysics, vol. 22(1-3):129-146 (1993).

Saridaki, Zacharenia et al., "Impact of KRAS, BRAF, PIK3CA Mutations, PTEN, AREG, EREG Expression and Skin Rash in 2nd Line Cetuximab-Based Therapy of Colotectal Cancer Patients," PLoS ONE, vol. 6(1):e15980, 1-13 (2011).

Schoeberl, Birgit et al., "Therapeutically Targeting ErbB3: A Key Node in Ligand-Induced Activation of the ErbB Receptor-PI3K Axis," Science Signaling, vol. 2(77):ra31, 1-14 (2009).

Siena, Salvatore et al., "Biomarkers Predicting Clinical Outcome of Epidermal Growth Factor Receptor-Targeted Therapy in Metastatic Colorectal Cancer," J. Natl. Cancer, vol. 101:1-17 (2009).

Tabernero, Josep et al., "Pharmacogenomic and Pharmacoproteomic Studies of Cetuximab in Metastatic Colorectal Cancer: Biomarker Analysis of a Phase I Dose-Escalation Study," J. Clin. Oncol., vol. 28:1181-1189 (2010).

Yonesaka, Kimio et al., "Autocrine Production of Amphiregulin Predicts Sensitivity to Both Gefitinib and Cetuximab and EGFR Wild-type Cancers," Clin. Cancer Res., vol. 14(21):6963-6973 (2008).

European Search Report for Application No. 12275088.8, 12 pages, dated Oct. 11, 2012.

International Search Report for Application No. PCT/US2012/045235, 5 pages, dated Feb. 20, 2013.

International Preliminary Report on Patentability and Written Opinion for Application No. PCT/US2012/045235, 7 pages, dated Jan. 7, 2014.

Wikipedia, "Competitive inhibition," retrieved online at: http://en.wikipedia.org/wiki/Competitive_inhibition, 5 pages, dated Sep. 13, 2011.

* cited by examiner

IgG1 Domain ID using alignment with a Vbase database VH region

```
                              FR1                                      CDR1    Section 1
           1          10         20         30         40         50         60    63
SEQ ID NO: 1  MGEGLSWLFLVAILKGVQC QVQLVQSGAEVKKPGASVKVSCKASGYTFTSYGINWVR
SEQ ID NO: 2  MGGGLSWLFLVAILKGVQC QVQLVQSGAEVKKPGASVKVSCKASGYTFTSYGIHWVR
SEQ ID NO: 3  MGEGLSWLFLVAILKGVQC QVQLVQSGAEVKKPGASVKVSCKASGYTFTSYGINWVR
SEQ ID NO: 4  MGEGLSWLFLVAILKGVQC QVQLVQSGAEVKKPGASVKVSCKASGYIFTSYGIMVR
SEQ ID NO: 5  MGEGLSWLFLVAILKGVQC QVQLVQSGAEVKKPGASVKVSCKASGYTFTSYGIMVR
                                  QVQLVQSGAEVKKPGASVKVSCKASGYTFTSYGIMVR (SEQ ID NO: 59)VH1-18_JH5_Vbase (1)
                         FR2              CDR2                 FR3             Section 2
           64         70         80         90        100        110        120      126
SEQ ID NO: 1  QAPGQGLEWMGWISAYNGNTN YAQKLQGRVTMTTDTSTSTAYMELRSLRSDDTAVYYCARDSG
SEQ ID NO: 2  QAPGQGLEWMGWISAYNGNTN YAQKLQGRVTMTTDTSTSTAYMELRSLRSDDTAVYYCARDGG
SEQ ID NO: 3  QAPGQGLEWMGWISAYNGNTD YAQKLQGRVTMTTDTSTSTAYMELRSLRSDDTAVYYCARDLG
SEQ ID NO: 4  QAPGQGLEWMGWISAYNGNTN YAQKLQGRVTMTTDTSTSTAYMELRSLRSDDTAVYYCARDGG
SEQ ID NO: 5  QAPGQGLEWMGWISAYNGNTN YAQKLQGRVTMTTDTSTSTAYMELRSLRSDDTAVYYCARDLG
              QAPGQGLEWMGWISAYNGNTN YAQKLQGRVTMTTDTSTSTAYMELRSLRSDDTAVYYCAR (SEQ ID NO: 59)VH1-18_JH5_Vbase (39)
                JH5                                                      Section 3
        127 130        140        150    155
SEQ ID NO: 1  GYGSSG-SVFFDPWGQGTLVTVSS
SEQ ID NO: 2  GYGSSG-SVFFDPWGQGTLVTVSS
SEQ ID NO: 3  PIGFG-PPFFDPWNGQGTLVTVSS
SEQ ID NO: 4  GYGSGG-VCFDRWGRGTSVTVSS
SEQ ID NO: 5  GYGSSG-VCMFD2WGQGTLVTVSS (SEQ ID NO: 59)VH1-18_JH5_Vbase (99)
``` immediately following the JH sequence SS, all VH sequences end with the following VH constant region sequence: SEQ ID NO:18
ASTKGPSVFPLAPSSKSTSGGTAALGCLVKDYFPEPVTVSWNSGALTSGVHTFPAVLQSSGLYSLSSVVTVPSSSLGTQTYICNVNHKPS
NTKVDKKVEPKSCDKTHTCPPCPAPELLGGPSVFLFPPKPKDTLMISRTPEVTCVVVDVSHEDPEVKFNWYVDGVEVHNAKTKPREEQ
YNSTYRVVSVLTVLHQDWLNGKEYKCKVSNKALPAPIEKTISKAKGQPREPQVYTLPPSREEMTKNQVSTCLVKGFYPSDIAVEWESNG
QPENNYKTTPPVLDSDGSFFLYSKLTVDKSRWQQGNVFSCSVMHEALHNHYTQKSLSLSPGK Numbers above sequences are offset by +6, so that the glycine labeled 10 is properly amino acid number 4

Amino acids numbers 1-20 for each of SEQ ID NO:1, SEQ ID NO:2, SEQ ID NO:3, SEQ ID NO:4, and SEQ ID NO:5 are
MGFGLSWLFLVAILKGVQCQ (SEQ ID NO: 60)

*Fig. 1*

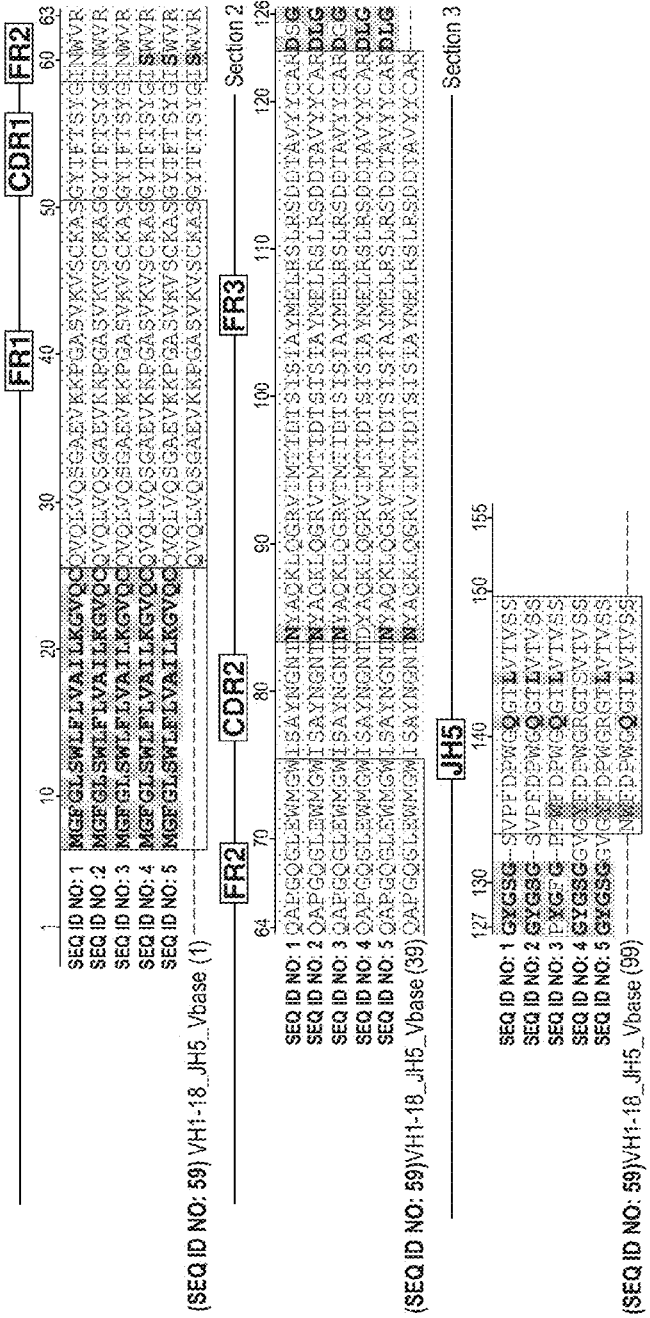

IgG1 Domain ID using alignment with Vbase database VH regions

```
                        1         10        20        30        40        50        60  63
                        |         |         |         |         |         |         |   |
                                                                          FR1              CDR1
SEQ ID NO: 6   MGFGLSWLFLVAILKGVQC QVQLVQSGAEVKKPGSSVKVSCKASGGTFSSYAISWVR
SEQ ID NO: 7   MGFGLSWIFLVAILKGVQC QVQLVQSGAEVKKPGSSVKVSCKASGGTFGSYAISWVR
SEQ ID NO: 8   MGFGLSWLFLVAILKGVQC QVQLVQSGAEVKKPGSSVKVSCKASGGTFSSYAISWVR
(SEQ ID NO: 61)VH1-69_JH3_Vbase (1)
SEQ ID NO: 9   MGFGLSWIFLFWAILKGVQC QVQLVQSGAEVKKPGSSVKVSCKASGGTFSSYAISWVR
(SEQ ID NO: 62)VH1-69_JH2_Vbase (1)

Section 2
                                   FR2                            CDR2                             FR3                                                  110       120    126
SEQ ID NO: 6   QAPGQGLEWMGSTIPIFGTANYAQKFQGRVTITADESTSTAYMELSSLRSEDTAVYYCAR
SEQ ID NO: 7   QAPGQGLEWMGSTIPIFGTANYAQKFQGRVTITADESTSTAYMELSSLRSEDTAVYYCAR    M
SEQ ID NO: 8   QAPGQGLEWMGSTIPIFGTANYAQKFQGRVTITADESTSTAYMELSSLRSEDTAVYYCAR    M
SEQ ID NO: 9   QAPGQGLEWMGSTIPIFGTANYAQKFQGRVTITADESTSTAYMELSSLRSEDTAVYYCARDPS M
(SEQ ID NO: 61)VH1-69_JH3_Vbase (39)
(SEQ ID NO: 62)VH1-69_JH2_Vbase (39)

Section 3
              127  130       140         152
                            JH3                    JH2
SEQ ID NO: 6   GRGXVAFDIWGQGTMVTASS
SEQ ID NO: 7   ARGXXAFDIWGQGTMVTVSS
SEQ ID NO: 8   VRGKVAFDIWGQGTMVVVSS
SEQ ID NO: 9   VDLYWYFDLWGRGTLVTVSS
(SEQ ID NO: 61)VH1-69_JH3_Vbase (99)  AFDIWGQGTMVTVSS
(SEQ ID NO: 62)VH1-69_JH2_Vbase (99)  YWYFDLWGRGTLVTVSS
```

Immediately following the JH sequence SS, all VH sequences end with the following VH constant region sequence: SEQ ID NO:18 ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVE PKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDW LNGKEYKCKVSNKALPAPIEKTISKAKGQPREPQVYTLPPSREEMTKNQVSTCLVKGFYPSDIAVEWESNGQPENNYKTTPPVLDSDGSFFLYSKLTVD KSRWQQGNVFSCSVMHEALHNHYTQKSLSLSPGK Numbers above sequences are offset by +6, so that the glycine labeled 10 is properly amino acid number 4

Amino acids numbers 1-20 for each of SEQ ID NO:6, SEQ ID NO:7, SEQ ID NO:8, and SEQ ID NO:9 are MGFGLSWLFLVAILKGVQCQ (SEQ ID NO: 60)

*Fig. 3*

IgG1 Domain ID using alignment with IMGT database VH regions

```
                           FR1                              CDR1           FR2
                 1         10        20        30        40        50        60   63
SEQ ID NO: 6     MGFGLSWLFLVAILKGVQCQ VQLVQSGAEVKKPGSSVKVSCKASGGTFSSYAISWVR
SEQ ID NO: 7     MGFGLSWILFLVAILKGVQC  QVQLVQSGAEVKKPGSSVKVSCKASGGTFSSYAISWVR
SEQ ID NO: 8     MGFGLSWLFLVAILKGVQC   QVQLVQSGAEVKKPGSSVKVSCKASGGTFSSYAISWVR
(SEQ ID NO: 61)VH1-69_JH3_Vbase(1)   QVQLVQSGAEVKKPGSSVKVSCKASGGTFSSKYAISWVR
SEQ ID NO: 9     MGFGLSWLFLVAILKGVQC   QVQLVQSGAEVKKPGSSVKVSCKASGGTFSSYAISWVR
(SEQ ID NO: 62)VH1-69_JH2_Vbase(1)   QVQLVQSGAEVKKPGSSVKVSCKASGGTFSSYAISWVR
                                                                              Section 2
              FR2                CDR2                    FR3
              64        70        80        90        100       110       120    126
SEQ ID NO: 6  QAPGQGLEWMGGIIPIFGTANYAQKFQGRVTITADESTSTAYMELSSLRSEDTAVYYCAR   M
SEQ ID NO: 7  QAPGQGLEWMGGIIPIFGTANYAQKFQGRVTITADESTSTAYMELSSLRSEDTAVYYCAR   M
SEQ ID NO: 8  QAPGQGLEWMGGIIPIFGTANYAQKFQGRVTITADESTSTAYMELSSLRSEDTAVYYCAR   M
(SEQ ID NO: 61)VH1-69_JH3_Vbase(39) QAPGQGLEWMGGIIPIFGTANYAQKFQGRVTITADESTSTAYMELSSLRSEDTAVYYCAR
SEQ ID NO: 9  QAPGQGLEWMGGIIPIFGTANYAQKFQGRVTITADESTSTAYMELSSLRSEDTAVYYCARDPS
(SEQ ID NO: 62)VH1-69_JH2_Vbase(39) QAPGQGLEWMGGIIPIFGTANYAQKFQGRVTITADESTSTAYMELSSLRSEDTAVYYCAR
                                                                               Section 3
                       JH3              152
                 127 130      140      150
SEQ ID NO: 6       GRGKVAFDIWGQGTMVTASS
SEQ ID NO: 7       ARGKVAFDIWGQGTMVTVSS
SEQ ID NO: 8       VRGKVAFDIWGQGTMVTVSS
(SEQ ID NO: 61)VH1-69_JH3_Vbase(99)  AFDIWGQGTMVTVSS
SEQ ID NO: 9       VDLYWYFDMWGRGTLVTVSS
                          JH2
(SEQ ID NO: 62)VH1-69_JH2_Vbase(99)    YWYFDMWGRGTLVTVSS
```

Immediately following the JH sequence SS, all VH sequences end with the following VH constant region sequence: SEQ ID NO:18
ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCD
KTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCK
VSNKALPAPIEKTISKAKGQPREPQVYTLPPSREEMTKNQVSTCLVKGFYPSDIAVEWESNGQPENNYKTTPPVLDSDGSFFLYSKLTVDKSRWQQGNVFSCSV
MHEALHNHYTQKSLSLSPGK Numbers above sequences are offset by +6, so that the glycine labeled 10 is properly amino acid number 4

Amino acids numbers 1-20 for each of SEQ ID NO:6, SEQ ID NO:7, SEQ ID NO:8, and SEQ ID NO:9 are MGFGLSWLFLVAILKGVQCQ (SEQ ID NO: 60)

Fig. 4

IgG1 Domain ID using alignment with a Vbase database VK region

```
                    1              10            20            30         FR1  40            50      CDR1  60            70  FR2  72
SEQ ID NO: 12  MGTPAQLLFLLLLWLPDTTGEIVMTQSPATLSLSPGERATLSCRASQSVSSNLAWYQQKPGQAPRL
SEQ ID NO: 13  MGTPAQLLFLLLLWLPDTTGEIVMTQSPATLSVSPGERATLSCRASQSVSSNLAWYQQKPGQAPRL
SEQ ID NO: 14  MGTPAQLLFLLLLWLPDTTGEIVMTQSPATLSVSPGERATLSCRASQSVSSNLAWYQQKPGQAPRL
(SEQ ID NO: 65)VK3-15_JK4_IMGT(1)  EIVMTQSPATLSVSPGERATLSCRASQSVSSNLAWYQQKPGQAPRL 73     80     CDR2   90         FR3  100           110         CDR3  120         JK4  130           140 Section 2
SEQ ID NO: 12  LIYGASTRATGIPARFSGSGSGTEFTLTISSLQSEDFAVYYCQQYN WPR AFGGGTKVEIK
SEQ ID NO: 13  LIYGASTRATGIPARFSGSGSGTEFTLTISSLQSEDFAVYYCQQYN WPR AFGGGTKVEIK
SEQ ID NO: 14  LIYGASTRATGIPARFSGSGSGTEFTLTISSLQSEDFAVYYCQQYNDWPR       FGGGTKVEIK
(SEQ ID NO: 65)VK3-15_JK4IMGT(47) LIYGASTRATGIPARFSGSGSGTEFTLTISSLQSEDFAVYYCQQYNNWPR     FGGGTKVEIK
```

Immediately following the JK sequence EIK, all VK sequences end with the following VK constant region sequence: SEQ ID NO:66
RTVAAPSVFIFPPSDEQLKSGTASVVCLLNNFYPREAKVQWKVDNALQSGNSQESVTEQDSKDSTYSLSSTLTLSKADYEKHKVYACEV
THQGLSSPVTKSFNRGEC Numbers above sequences are offset by +6, so that the proline labeled 10 is properly amino
acid number 4

Amino acids numbers 1 -20 for each of SEQ ID NO 12, SEQ ID NO:13, and SEQ ID NO:14
are MGTPAQLLFLLLLWLPDTTG (SEQ ID NO: 67)

*Fig. 8*

IgG1 Domain ID using alignment with a Vbase database VK region

```
                                FR1                    CDR1            FR2
         (1)    1         10         20         30         40         50         60    67
SEQ ID NO: 15  MGTPAQLLFLLLLWLPDTTGEIVLTQSPATLSLSPGERATLSCRASQSVSSSYLAWYQQKPG
SEQ ID NO: 16  MGTPAQLLFLLLLWLPDTTG
(SEQ ID NO: 70) VK3-11_JK4_IMGT (1)  EIVLTQSPATLSLSPGERATLSCRASQSVSSSYLAWYQQKPG
                                    EIVLTQSPATLSLSPGERATLSCRASQSVSSSYLAWYQQKPG

CDR2              FR3                            CDR3       JK4    Section 2
         (69)  68         80         90        100        110        120     130 133
SEQ ID NO: 15  APRLLIYDASNRATGIPARFSGSGSGTDFTLTISSLEPEDFAVYYCQQRG-WPR-TFGGGTKVEIK
SEQ ID NO: 16  APRLLIYDASNRATGIPARFSGSGSGTDFTLTISSLEPEDFAVYYCHQRG-WFS-TFGGGTKVEIK
(SEQ ID NO: 70) VK3-11_JK4_IMGT (43) APRLLIYDASNRATGIPARFSGSGSGTDFTLTISSLRPEDFAVYYCQQRSNWP--TFGGGTKVEIK
```

Immediately following the JK sequence EIK, all VK sequences end with the following VK constant region sequence: SEQ ID NO:66
RTVAAPSVFIFPPSDEQLKSGTASVVCLLNNFYPREAKVQWKVDNALQSGNSQESVTEQDSKDSTYSLSSTLTLSKADYEKHKVYACE
VTHQGLSSPVTKSFNRGEC Numbers above sequences are offset by +6, so that the proline labeled 10 is properly amino acid number 4

Amino acids numbers 1-20 for EACH of SEQ ID NO: 15 and SEQ ID NO: 16 are
MGTPAQLLFLLLLWLPDTTG (SEQ ID NO: 67)

*Fig. 14*

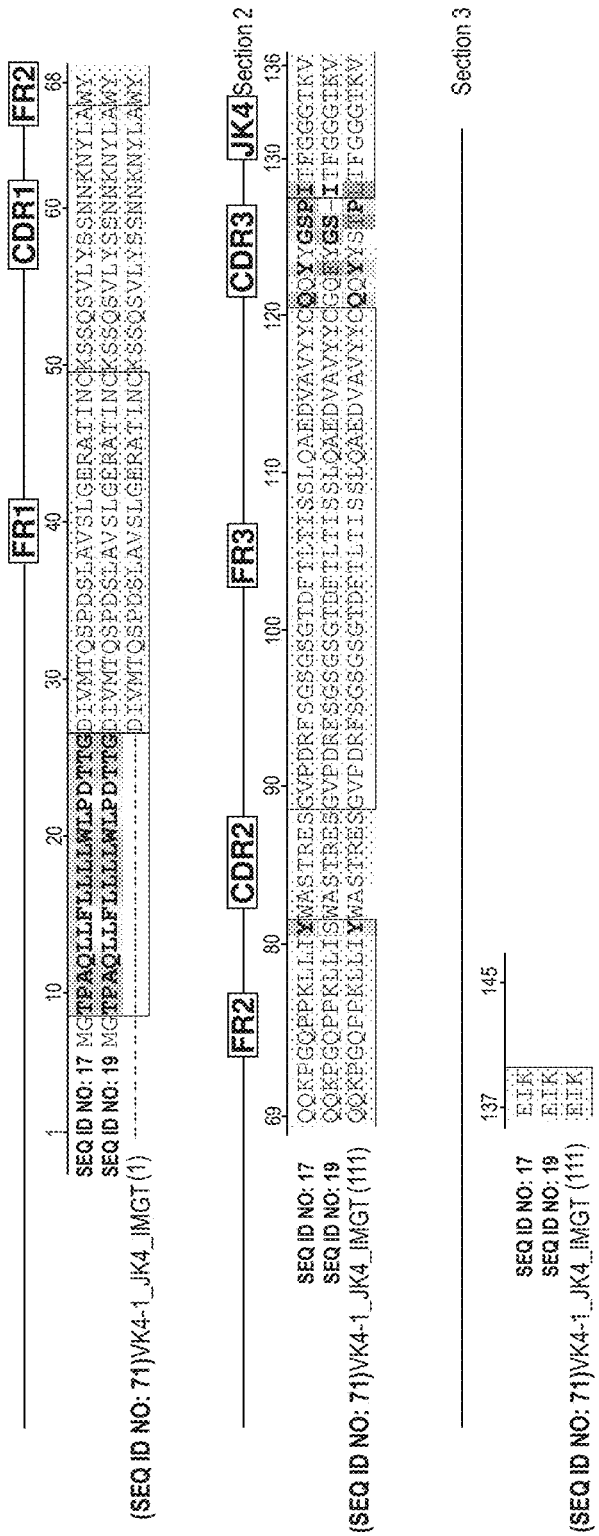

ANTIBODIES AGAINST EPIDERMAL GROWTH FACTOR RECEPTOR (EGFR) AND USES THEREOF

BACKGROUND

The natural immune system has evolved to make antibodies for efficient neutralization of pathogens. Natural antibody preparations isolated from immunized animals are polyclonal in origin, and exhibit immunodominance as compared to individual antibodies, which are restricted to one or a few epitopes of a particular antigen. Neutralizing antibodies are able to block a biological function of the antigen to which they bind. Mixtures of neutralizing antibodies may achieve neutralization that is greater than any individual antibody in the mixture.

Such results have been achieved by combining two or more neutralizing antibodies against the epidermal growth factor receptor, EGFR (ErbB1). Antibodies that bind to and inhibit EGFR have proven to provide useful anti-cancer benefits and are of great medical and commercial value. Particular combinations of pairs of antagonistic, yet non-competitive, anti-EGFR antibodies resulted in downregulation of EGFR which was faster and more effective than application of either antibody alone (Friedman et al. (2005) PNAS 102:1915-1920). The combination of two cross-competitive (i.e., competitive with each other for binding to antigen) anti-EGFR antibodies has shown to be non-synergistic. It is possible that binding of a plurality of antibodies to distinct epitopes of EGFR forms lattices of complexed receptors on cell surfaces, leading to more efficient internalization and degradation than obtained with antibodies targeting a single epitope. The combination of a particular pair of anti-EGFR receptor antibodies have also been reported to result in additive and in some cases synergistic, antitumor activity in vivo (Perera et al. (2005) Clin Cancer Res 11:6390-6399). Monoclonal antibody 806, raised against the mutant de2-7 EGFR, combined with antagonistic antibody 528 displayed significantly higher anti-tumor activity in a glioma xenograft model than treatment with either antibody alone. The mechanism of the synergistic anti-tumor activity was shown to be associated with rapid downregulation of EGFR, which was not induced by treatment with the individual antibodies. Similarly EGFR phosphorylation was greatly reduced in the presence of another pair of anti-EGFR antibodies, cetuximab and EMD55900 (Kamat et al. (2008) Cancer Biol Ther 7:726-33).

Certain combinations of antibodies targeting the related receptor, ErbB2, have also been shown to function in synergy (Friedman et al. (2005). Trastuzumab combined with pertuzumab inhibited the survival of BT474 breast cancer cells at doses in which individual antibodies are ineffective (Nahta et al. (2004) Cancer Res 64:2343-2346). In another study three non-competitive anti-ErbB2 antibodies demonstrated far more effective in vitro killing of BT474 cells in combination than individually and similar results were obtained in a BT474 in vivo xenograft model (Spiridon et al. (2002) Clin Cancer Res 8:1699-701).

Other evidence that combining more than one antibody may enhance the growth suppressive (e.g., cytotoxic) effect of antibodies on tumor cells has been reported. For example, monoclonal antibodies to the tumor antigen 17-1A were combined, tumor cell lysis was studied, an it was found that that monoclonal antibodies, as well as combinations of competing antibodies, were ineffective, whereas combinations of two or more non-competing antibodies resulted in complete tumor cell lysis.

Accordingly, additional approaches and methods for producing combinatorial action so as to enhance the responsiveness of tumors to anti-EGFR antibody combinations are still needed, including combinations that enhance signaling inhibition and combinations that provide more effective cytostatic or cytotoxic outcomes.

SUMMARY

Novel monoclonal antibodies that bind to EGFR and inhibit various EGFR functions are provided herein. These antibodies, when combined with each other or with other anti-ErbB receptor antibodies (e.g., other anti-EGFR antibodies), are capable of exhibiting a synergistic or additive therapeutic effect compared to the administration of each antibody alone. These antibodies, particularly when administered in combinations as herein provided, are useful for treating a variety of disorders (e.g., cancers) associated with EGFR-mediated cellular signaling. Accordingly, combinations of novel monoclonal antibodies that bind to EGFR and inhibit various EGFR functions are also provided herein. Uses of these antibodies for diagnostic and therapeutic purposes are also provided, as are uses of the antibody combinations herein disclosed.

In one embodiment, monoclonal antibodies that bind EGFR and combinations of such antibodies are provided. These antibodies and combinations exhibit one or more of the following properties:

(a) inhibition of AKT or ERK phosphorylation, e.g., EGFR-dependant AKT or ERK phosphorylation, as measured in a cell-based assay;
(b) inhibition of the growth of cells expressing EGFR;
(c) inhibition of EGF ligand binding to EGFR;
(d) inhibition of EGFR dimerization; or
(e) downregulation of EGFR on cell surfaces (e.g., by internalization and recycling of the receptor, and/or internalization and degradation of the receptor).

In a particular embodiment, the antibodies (i.e., when combined) bind non-overlapping epitopes, as determined using a surface plasmon resonance assay (e.g., BIACORE) or FACS, or other such assays. In another particular embodiment, the antibodies additively or synergistically provide at least one of the functional properties described above, i.e., (a) inhibition of AKT or ERK phosphorylation, e.g., EGFR-dependant AKT or ERK phosphorylation, as measured in a cell-based assay;
(b) inhibition of the growth of cells expressing EGFR;
(c) inhibition of ligand binding to EGFR (e.g., inhibition of binding of one or more ligands that bind EGFR, including EGF, transforming growth factor (TGF), or amphiregulin);
(d) inhibition of EGFR dimerization; or
(e) downregulation of EGFR on cell surfaces.

In another embodiment, the individual monoclonal antibodies inhibit the actions of EGFR ligands, yet do not cross-compete (i.e., they bind to distinct epitopes).

Particular anti-EGFR monoclonal antibodies provided herein include those that comprise a heavy chain variable region comprising an amino acid sequence selected from the group consisting of SEQ ID NOs:1-11 or a light chain variable region comprising an amino acid sequence selected from the group consisting of SEQ ID NOs: 12-17 and 19-22. Antibodies herein provided also include those that comprise a heavy and a light chain variable region comprising the following amino acid sequences:

TABLE I

| * | Heavy Chain | | Light Chain |
|---|---|---|---|
| va | SEQ ID NO: 9 | and | SEQ ID NO: 20; |
| vb | SEQ ID NO: 10 | and | SEQ ID NO: 21; |
| vc | SEQ ID NO: 11 | and | SEQ ID NO: 22; |
| vd | SEQ ID NO: 1 | and | SEQ ID NO: 12; |
| ve | SEQ ID NO: 2 | and | SEQ ID NO: 13; |
| vf | SEQ ID NO: 3 | and | SEQ ID NO: 14; |
| vg | SEQ ID NO: 4 | and | SEQ ID NO: 15; |
| vh | SEQ ID NO: 5 | and | SEQ ID NO: 16; |
| vi | SEQ ID NO: 6 | and | SEQ ID NO: 17; |
| vj | SEQ ID NO: 8 | and | SEQ ID NO: 19. |

* Antibody name, i.e., va, vb, vc, etc.

Other particular antibodies herein include those that comprise the following heavy and light chain CDR3, CDR2, and CDR1, sequences (each two digit number in this Table II represents a SEQ ID NO: as set forth in Tables VI and VII below).

TABLE II

| | Heavy chain (SEQ ID NO:) | | | Light Chain (SEQ ID NO:) | | |
|---|---|---|---|---|---|---|
| ** | CDR3 | CDR2 | CDR1 | CDR3 | CDR2 | CDR1 |
| ca | 34 | 30 | 29 | 49 | 45 | 48; |
| cb | 37 | 36 | 35 | 51 | 45 | 50; |
| cc | 38 | 36 | 35 | 52 | 45 | 48; |
| cd | 31 | 30 | 29 | 55 | 54 | 53; |
| ce | 32 | 30 | 29 | 55 or 56 | 54 | 53; |
| cf | 33 | 30 | 29 | 56 | 54 | 53; |
| cg | 25 | 24 | 23 | 41 | 40 | 39; |
| ch | 26 | 24 | 23 | 42 | 40 | 39; |
| ci | 27 | 24 | 23 | 43 | 40 | 39; |
| cj | 28 | 24 | 23 | 46 | 45 | 44; |
| ck | 28 | 24 | 23 | 47 | 45 | 44. |

** Antibody name, i.e., ca, cb, cc, etc.

Also encompassed by the present invention are monoclonal antibodies that bind to the same or overlapping epitopes bound by any of the particular antibodies described herein below.

Antibodies disclosed herein include all known forms of antibodies and other protein scaffolds with antibody-like properties. For example, the antibody can be a human antibody, a humanized antibody, a bispecific antibody, an immunoconjugate, a chimeric antibody or a protein scaffold with antibody-like properties, such as fibronectin or ankyrin repeats. The antibody also can be a Fab, Fab'2, ScFv, affibody, nanobody, or a domain antibody. The antibody also can have any isotype, including any of the following isotypes: IgG1, IgG2, IgG3, IgG4, IgM, IgA1, IgA2, IgAsec, IgD, and IgE. IgG antibodies are preferred.

Exemplary combinations of two antibodies (hereinafter "pair" or "pairs") herein provided include:

TABLE III

Each named pair also encompasses pairs of one each of antibodies that compete for binding to EGFR with each of the named antibodies of the pair

| *** | ** | | |
|---|---|---|---|
| a | ca and cd; | x | cc and ck; |
| b | ca and ce; | y | va and vd; |
| c | ca and cf; | z | va and ve; |
| d | ca and cg | aa | va and vf; |
| e | ca and ch; | ab | va and vg; |
| f | ca and ci; | ac | va and vh; |
| g | ca and cj; | ad | va and vi; |
| h | ca and ck; | ae | va and vj; |

TABLE III-continued

Each named pair also encompasses pairs of one each of antibodies that compete for binding to EGFR with each of the named antibodies of the pair

| *** | ** | | |
|---|---|---|---|
| i | cb and cd; | ag | vb and vd; |
| j | cb and ce; | ah | vb and ve; |
| k | cb and cf; | ai | vb and vf; |
| l | cb and cg | aj | vb and vg |
| m | cb and ch; | ak | vb and vh; |
| n | cb and ci; | al | vb and vj; |
| o | cb and cj; | am | vb and vj; |
| p | cb and ck; | ao | vc and vd; |
| q | cc and cd; | ap | vc and ve; |
| r | cc and ce; | aq | vc and vf; |
| s | cc and cf; | ar | vc and vg |
| t | cc and cg | as | vc and vh; |
| u | cc and ch; | at | vc and vi; |
| v | cc and ci; | au | vc and vj; |
| w | cc and cj; | | |

***Name of antibody pair

As set forth in the above tables, a named antibody is considered to be an antibody that will compete with itself.

Exemplary combinations of three of more antibodies include each pair designated a-x immediately above in combination with a third antibody not present in the particular pair and selected from cd, ce, cf, cg, ch, ci, cj, and ck and further include each binary combination designated above as y, z, aa, ab, ac, ad, ae, ag, ah, ai, aj, ak, al, am, ao, ap, aq, ar, as, at, au, or av in combination with a third antibody not present in the particular pair and selected from vd, ye, vf, vg, vh, vi, and vj.

Exemplary combinations of three antibodies (hereinafter "trio" or "trios") herein provided also include those named in TABLE IV and Table V below, as well as trios comprising, for each trio named in TABLE IV and Table V, below, one each of antibodies that compete for binding to EGFR with each of the antibodies of that named trio.

TABLE IV

| Trio Name | 1st antibody | 2nd Antibody | 3rd Antibody |
|---|---|---|---|
| 1c | ca | cg | cd |
| 2c | ca | cg | ce |
| 3c | ca | cg | cf |
| 4c | ca | ch | cd |
| 5c | ca | ch | ce |
| 6c | ca | ch | cf |
| 7c | ca | ci | cd |
| 8c | ca | ci | ce |
| 9c | ca | ci | cf |
| 10c | ca | cj | cd |
| 11c | ca | cj | ce |
| 12c | ca | cj | cf |
| 13c | ca | ck | cd |
| 14c | ca | ck | ce |
| 15c | ca | ck | cf |
| 16c | cb | cg | cd |
| 17c | cb | cg | ce |
| 18c | cb | cg | cf |
| 19c | cb | ch | cd |
| 20c | cb | ch | ce |
| 21c | cb | ch | cf |
| 22c | cb | ci | cd |
| 23c | cb | ci | ce |
| 24c | cb | ci | cf |
| 25c | cb | cj | cd |
| 26c | cb | cj | ce |
| 27c | cb | cj | cf |
| 28c | cb | ck | cd |
| 29c | cb | ck | ce |
| 30c | cb | ck | cf |
| 31c | cc | cg | cd |

TABLE IV-continued

| Trio Name | 1st antibody | 2nd Antibody | 3rd Antibody |
|---|---|---|---|
| 32c | cc | cg | ce |
| 33c | cc | cg | cf |
| 34c | cc | ch | cd |
| 35c | cc | ch | ce |
| 36c | cc | ch | cf |
| 37c | cc | ci | cd |
| 38c | cc | ci | ce |
| 39c | cc | ci | cf |
| 40c | cc | cj | cd |
| 41c | cc | cj | ce |
| 42c | cc | cj | cf |
| 43c | cc | ck | cd |
| 44c | cc | ck | ce |
| 45c | cc | ck | cf |

TABLE V

| Trio Name | 1st antibody | 2nd Antibody | 3rd Antibody |
|---|---|---|---|
| 1v | va | vi | vd |
| 2v | va | vi | ve |
| 3v | va | vi | vf |
| 4v | va | vi | vg |
| 5v | va | vi | vh |
| 6v | va | vj | vd |
| 7v | va | vj | ve |
| 8v | va | vj | vf |
| 9v | va | vj | vg |
| 10v | va | vj | vh |
| 11v | vb | vi | vd |
| 12v | vb | vi | ve |
| 13v | vb | vi | vf |
| 14v | vb | vi | vg |
| 15v | vb | vi | vh |
| 16v | vb | vj | vd |
| 17v | vb | vj | ve |
| 18v | vb | vj | vf |
| 19v | vb | vj | vg |
| 20v | vb | vj | vh |
| 21v | vc | vi | vd |
| 22v | vc | vi | ve |
| 23v | vc | vi | vf |
| 24v | vc | vi | vg |
| 25v | vc | vi | vh |
| 26v | vc | vj | vd |
| 27v | vc | vj | ve |
| 28v | vc | vj | vf |
| 29v | vc | vj | vg |
| 30v | vc | vj | vh |

As set forth in the above Tables I-V, a named antibody is considered to be an antibody that will compete with itself for binding to EGFR.

In the following Tables VI and VII, CDR amino acid sequences are set forth immediately above the corresponding SEQ ID NOs in each column, while corresponding full heavy or light chain variable sequences are indicated by SEQ ID NO in the preceding row in the left hand column.

TABLE VI

| Heavy Chain | CDR 1 | CDR 2 | CDR 3 |
|---|---|---|---|
| SEQ ID NO: 1 | SYG | ISAYNGNT | DSGGYGSGS |
|  | SEQ ID NO: 23 | SEQ ID NO: 24 | SEQ ID NO: 25 |
| SEQ ID NO: 2 | SYG | ISAYNGNT | DLGGYGSGS |
|  | SEQ ID NO: 23 | SEQ ID NO: 24 | SEQ ID NO: 26 |
| SEQ ID NO: 3 | SYG | ISAYNGNT | DGGPYGFGP |
|  | SEQ ID NO: 23 | SEQ ID NO: 24 | SEQ ID NO: 27 |
| SEQ ID NO: 4 | SYG | ISAYNGNT | DLGGYGSGGV |
|  | SEQ ID NO: 23 | SEQ ID NO: 24 | SEQ ID NO: 28 |

TABLE VI-continued

| Heavy Chain | CDR 1 | CDR 2 | CDR 3 |
|---|---|---|---|
| SEQ ID NO: 5 | SYG | ISAYNGNT | DLGGYGSGGV |
|  | SEQ ID NO: 23 | SEQ ID NO: 24 | SEQ ID NO: 28 |
| SEQ ID NO: 6 | SYA | IIPIFGTA | MGRGKV |
|  | SEQ ID NO: 29 | SEQ ID NO: 30 | SEQ ID NO: 31 |
| SEQ ID NO: 7 | SYA | IIPIFGTA | MARGKV |
|  | SEQ ID NO: 29 | SEQ ID NO: 30 | SEQ ID NO: 32 |
| SEQ ID NO: 8 | SYA | IIPIFGTA | MVRGKV |
|  | SEQ ID NO: 29 | SEQ ID NO: 30 | SEQ ID NO: 33 |
| SEQ ID NO:9 | SYA | IIPIFGTA | DPSVDL |
|  | SEQ ID NO: 29 | SEQ ID NO: 30 | SEQ ID NO: 34 |
| SEQ ID NO: 10 | SGSYY | IYYSGST | DSPYYG |
|  | SEQ ID NO: 35 | SEQ ID NO: 36 | SEQ ID NO: 37 |
| SEQ ID NO: 11 | SGSYY | IYYSGST | EPLYD |
|  | SEQ ID NO: 35 | SEQ ID NO: 36 | SEQ ID NO: 38 |

TABLE VII

| Light Chain | CDR 1 | CDR 2 | CDR 3 |
|---|---|---|---|
| SEQ ID NO: 12 | QSVSSN | GAS | QDYRSWPR |
|  | SEQ ID NO: 39 | SEQ ID NO: 40 | SEQ ID NO: 41 |
| SEQ ID NO: 13 | QSVSSN | GAS | QDYRTWPR |
|  | SEQ ID NO: 39 | SEQ ID NO: 40 | SEQ ID NO: 42 |
| SEQ ID NO: 14 | QSVSSN | GAS | QQYNDWPR |
|  | SEQ ID NO: 39 | SEQ ID NO: 40 | SEQ ID NO: 43 |
| SEQ ID NO: 15 | QSVSSY | DAS | QQRGSWPR |
|  | SEQ ID NO: 44 | SEQ ID NO:45 | SEQ ID NO: 46 |
| SEQ ID NO: 16 | QSVSSY | DAS | HQRGTWPS |
|  | SEQ ID NO: 44 | SEQ ID NO: 45 | SEQ ID NO: 47 |
| SEQ ID NO: 17 | QSVLYSSNNKNY | WAS | QQYYGSP |
|  | SEQ ID NO: 53 | SEQ ID NO: 54 | SEQ ID NO: 55 |
| SEQ ID NO: 19 | QSVLYSSNNKNY | WAS | GQFYGS |
|  | SEQ ID NO: 53 | SEQ ID NO: 54 | SEQ ID NO: 56 |
| SEQ ID NO: 20 | QSISSW | DAS | QQFAAHA |
|  | SEQ ID NO: 48 | SEQ ID NO: 45 | SEQ ID NO: 49 |
| SEQ ID NO: 21 | QDITNY | DAS | HQYNAFP |
|  | SEQ ID NO: 50 | SEQ ID NO: 45 | SEQ ID NO: 51 |
| SEQ ID NO: 22 | QSISSW | DAS | QQYIEYA |
|  | SEQ ID NO: 48 | SEQ ID NO: 45 | SEQ ID NO: 52 |

Contemplated compositions may further include an additional therapeutic agent. Such compositions can be administered sequentially or together with other therapeutic treatments, such as anti-cancer therapies, e.g., one or more of other antibodies, chemotherapeutic agents and radiation.

Methods for selecting particular combinations of antibodies are also provided. In one embodiment, such methods include selecting anti-EGFR antibodies that have a particular IC50 and/or IC90 with respect to an EGFR activity or function (e.g., an IC90 of better than 80 nM for inhibiting EGFR-mediated signaling). Such antibodies can then be administered in combination (e.g., together) or sequentially. In another embodiment, the method includes the step of further selecting combinations of antibodies that do not compete with each other for binding to EGFR. Additional selection criteria include at least one of the following properties:

(i) inhibition of the growth of cells expressing EGFR in vivo;
(ii) inhibition of an EGFR ligand binding to EGFR;
(iii) inhibition of EGFR dimerization; or
(iv) downregulation of EGFR on cell surfaces.

Kits comprising one or more antibody or composition disclosed herein are also contemplated, optionally, contained within a single vial and/or with instructions for use in treating or diagnosing a disease associated with EGFR, such as cancers.

Antibodies and compositions disclosed herein can be used in a broad variety of therapeutic and diagnostic applications, particularly oncological applications. Accordingly, in another aspect, provided herein are methods for inhibiting EGFR activity in a subject by administering one or more antibodies or compositions described herein in an amount sufficient to inhibit EGFR-mediated activity. Particular therapeutic indications which can be treated include, for example, cancers of organs or tissues such as skin, brain and central nervous system, head and neck, esophagus, stomach, colon, rectum, anus, liver, pancreas, bile duct, gallbladder, lung or bronchus, breast, ovary, uterus, cervix, vagina, testis, germ cells, prostate, kidney, ureter, urinary bladder, adrenal, pituitary, thyroid, bone, muscle or other connective tissues, leukemia, multiple myeloma, Hodgkin's lymphoma and non-Hodgkin's lymphoma.

Antibodies of disclosed herein also can be used to diagnose or prognose diseases (e.g., cancers) associated with EGFR, for example, by contacting one or more antibodies, antibody pairs or antibody trios disclosed herein (e.g., ex vivo or in vivo) with cells from the subject, and measuring the level of binding to EGFR on the cells, wherein abnormally high levels of binding to EGFR indicate that the subject has a cancer associated with EGFR.

Other features and advantages of the invention will be apparent from the following detailed description, and from the claims.

BRIEF DESCRIPTION OF THE FIGURES

FIG. 1. Amino acid sequences for variable heavy regions comprised by SEQ ID NO:1, SEQ ID NO:2, SEQ ID NO:3, SEQ ID NO:4, and SEQ ID NO:5. Sequences are demarcated to show CDR positions as per the Vbase database. The sequence spanning the end of FR3 to the beginning of the JH region comprises CDR3. The amino acid sequence for the constant heavy region is also set forth.

FIG. 2. Amino acid sequences for variable heavy regions comprised by SEQ ID NO:1, SEQ ID NO:2, SEQ ID NO:3, SEQ ID NO:4, and SEQ ID NO:5. Sequences are demarcated to show CDR positions as per the IMGT database. The sequence spanning the end of FR3 to the beginning of the JH region comprises CDR3. The amino acid sequence for the constant heavy region is also set forth.

FIG. 3. Amino acid sequences for variable heavy regions comprised by SEQ ID NO:6, SEQ ID NO:7, SEQ ID NO:8, and SEQ ID NO:9. Sequences are demarcated to show CDR positions as per the Vbase database. The sequence spanning the end of FR3 to the beginning of the JH region comprises CDR3. The amino acid sequence for the constant heavy region is also set forth.

FIG. 4. Amino acid sequences for variable heavy regions comprised by SEQ ID NO:6, SEQ ID NO:7, SEQ ID NO:8, and SEQ ID NO:9. Sequences are demarcated to show CDR positions as per the IMGT database. (The sequence spanning the end of FR3 to the beginning of the JH region comprises CDR3. The amino acid sequence for the constant heavy region is also set forth.

FIG. 8. Amino acid sequences for variable light regions comprised by SEQ ID NO:12, SEQ ID NO:13, and SEQ ID NO:14. Sequences are demarcated to show CDR positions as per the Vbase database. The amino acid sequence for the constant light region is also set forth.

FIG. 14. Amino acid sequences for the variable light regions comprised by SEQ ID NO:15 and SEQ ID NO:16. Sequences are demarcated to show CDR positions as per the Vbase database. The amino acid sequence for the constant light region is also set forth.

FIG. 16. Amino acid sequences for the variable light regions comprised by SEQ ID NO:17 and SEQ ID NO:19. Sequences are demarcated to show CDR positions as per the Vbase database. The amino acid sequence for the constant light region is also set forth.

DETAILED DESCRIPTION

I. Definitions

Figure 5:
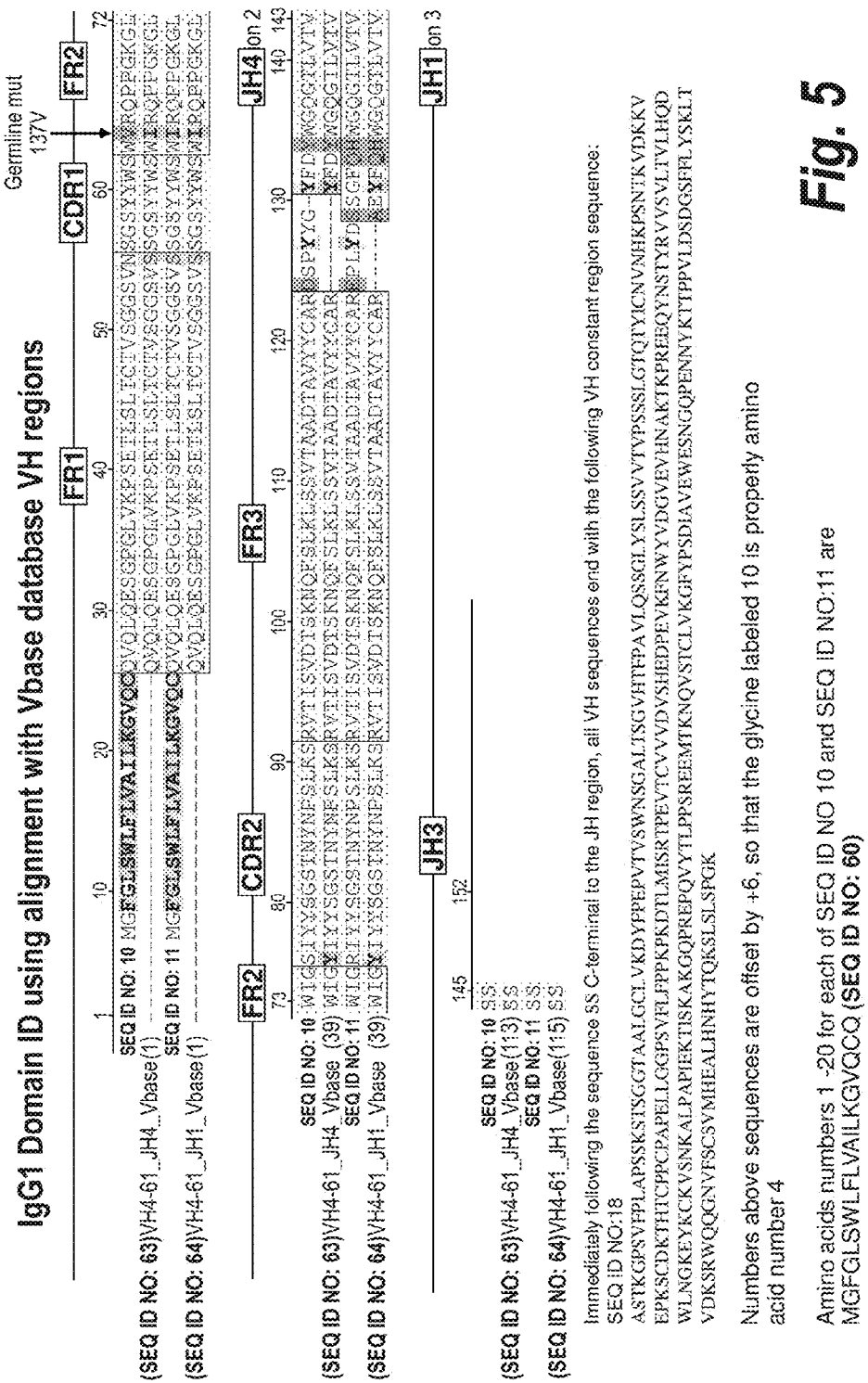
FIG. 5. Amino acid sequences for variable heavy regions comprised by SEQ ID NO:10, and SEQ ID NO:11. Sequences are demarcated to show CDR positions as per the Vbase database. The sequence spanning the end of FR3 to the beginning of the JH region comprises CDR3. The amino acid sequence for the constant heavy region is also set forth.
Figure 6:
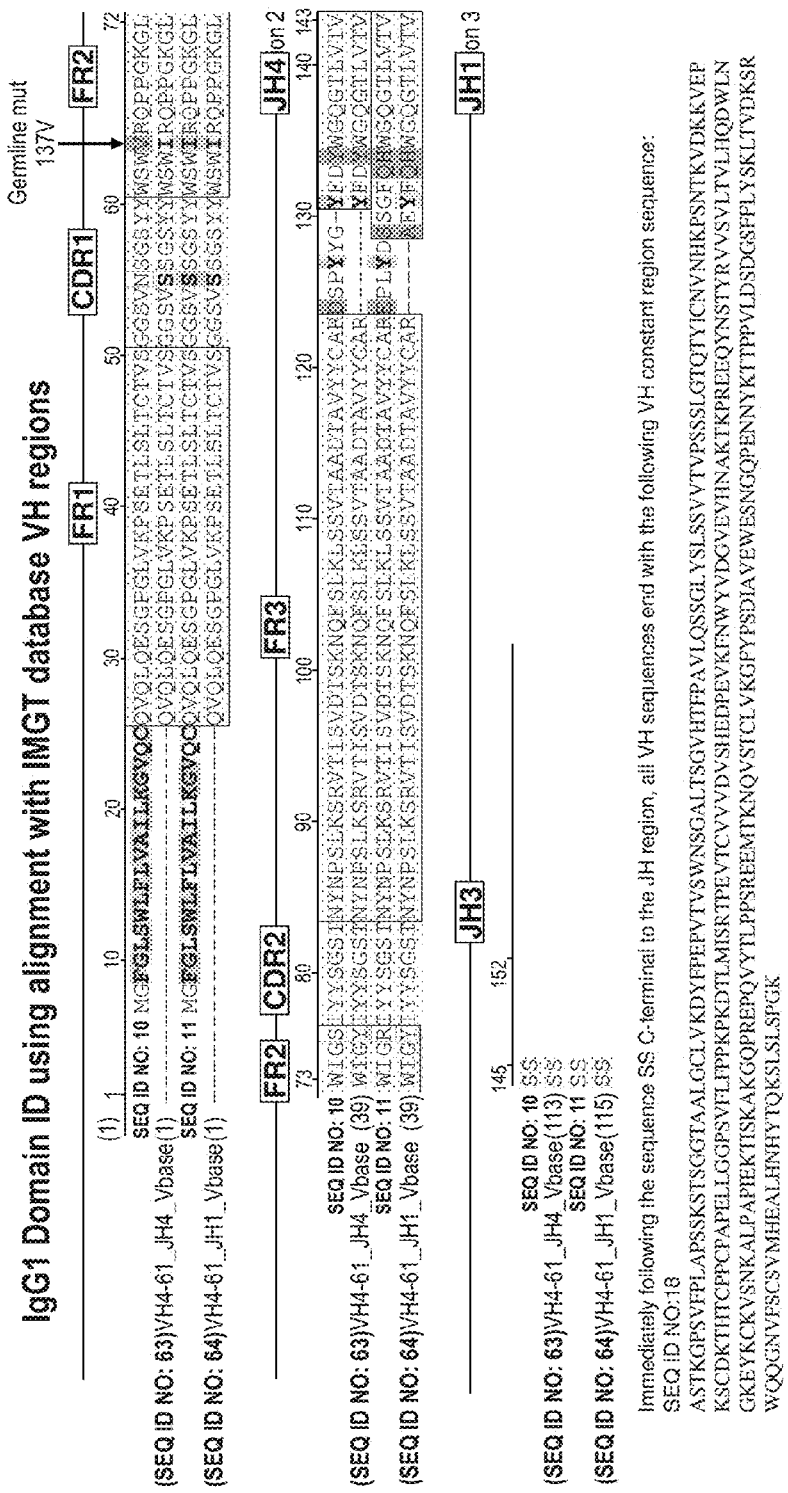
FIG. 6. Amino acid sequences for variable heavy regions comprised by SEQ ID NO:10, and SEQ ID NO:11. Sequences are demarcated to show CDR positions as per the IMGT database The sequence spanning the end of FR3 to the beginning of the JH region comprises CDR3. The amino acid sequence for the constant heavy region is also set forth.
Figure 7:
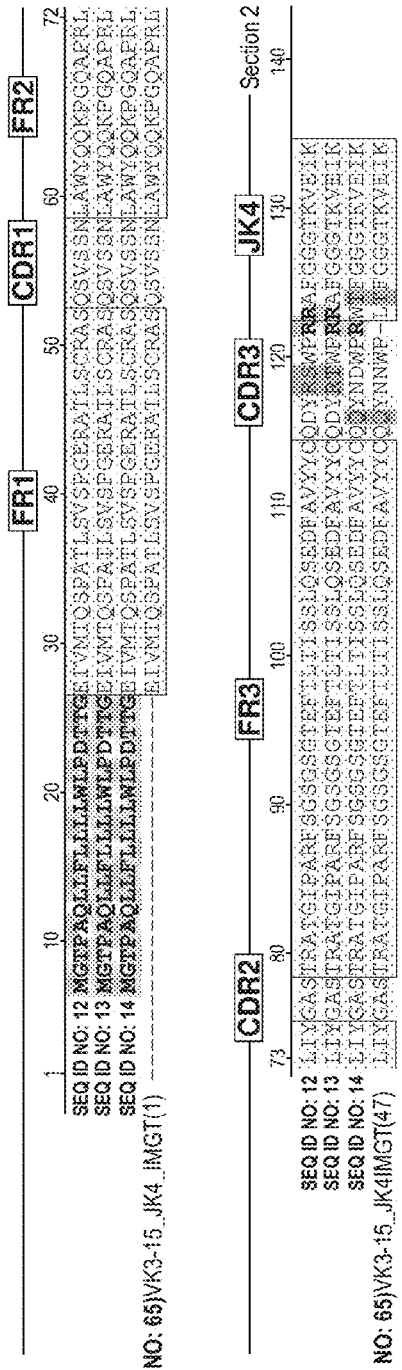
FIG. 7. Amino acid sequences for variable light regions (V kappa) comprised by SEQ ID NO:12, SEQ ID NO:13, and SEQ ID NO:14. Sequences are demarcated to show CDR positions as per the IMGT database. The amino acid sequence for the constant light region is also set forth.
Figure 9:
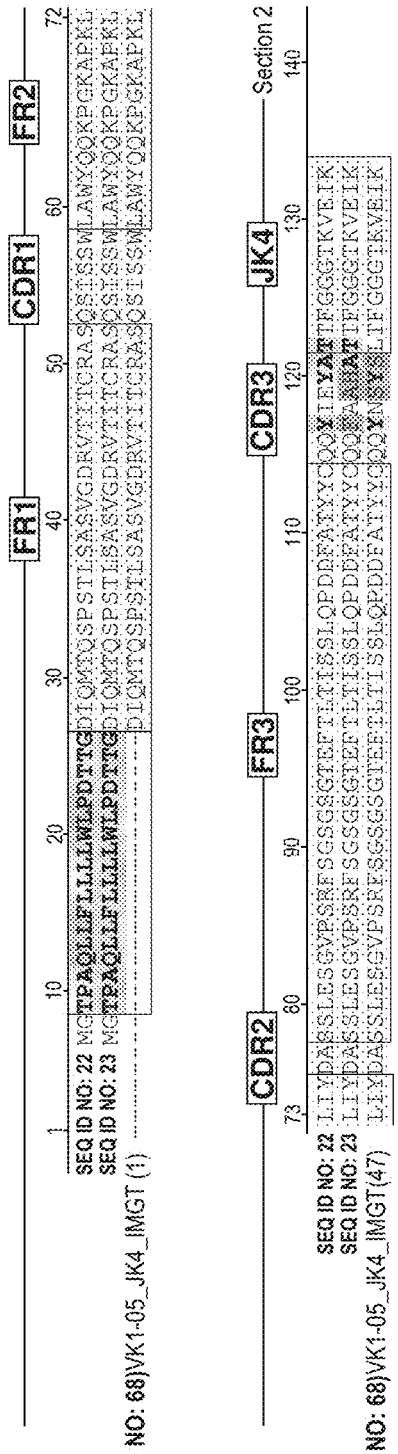
FIG. 9. Amino acid sequences for variable light regions comprised by SEQ ID NO:20 and SEQ ID NO:22. Sequences are demarcated to show CDR positions as per the IMGT database. The amino acid sequence for the constant light region is also set forth.
Figure 10:
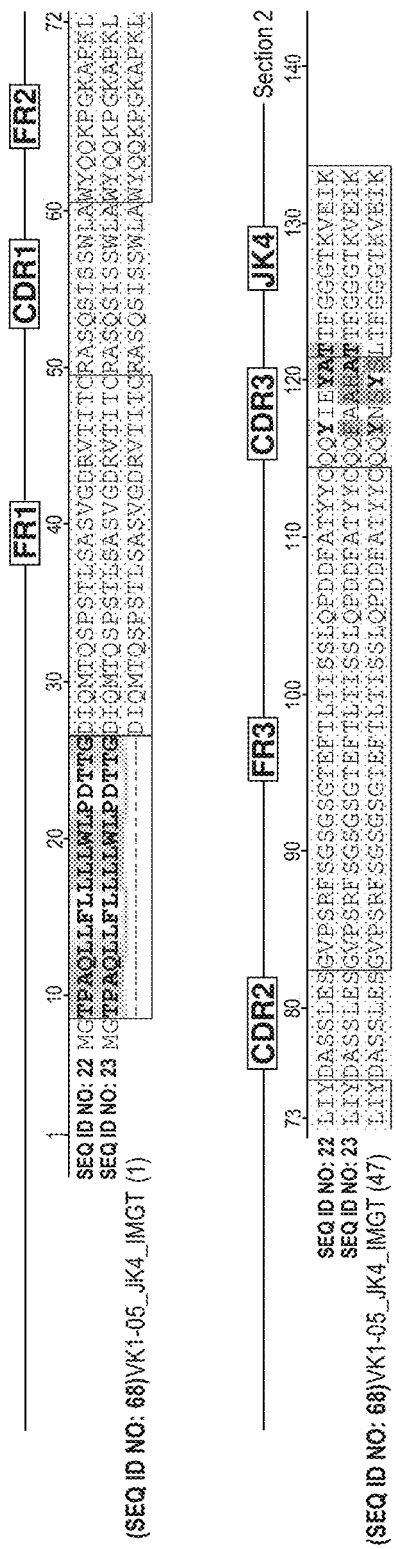
FIG. 10. Amino acid sequences for variable light regions comprised by SEQ ID NO:20 and SEQ ID NO:22. Sequences are demarcated to show CDR positions as per the Vbase database. The amino acid sequence for the constant light region is also set forth.
Figure 11:
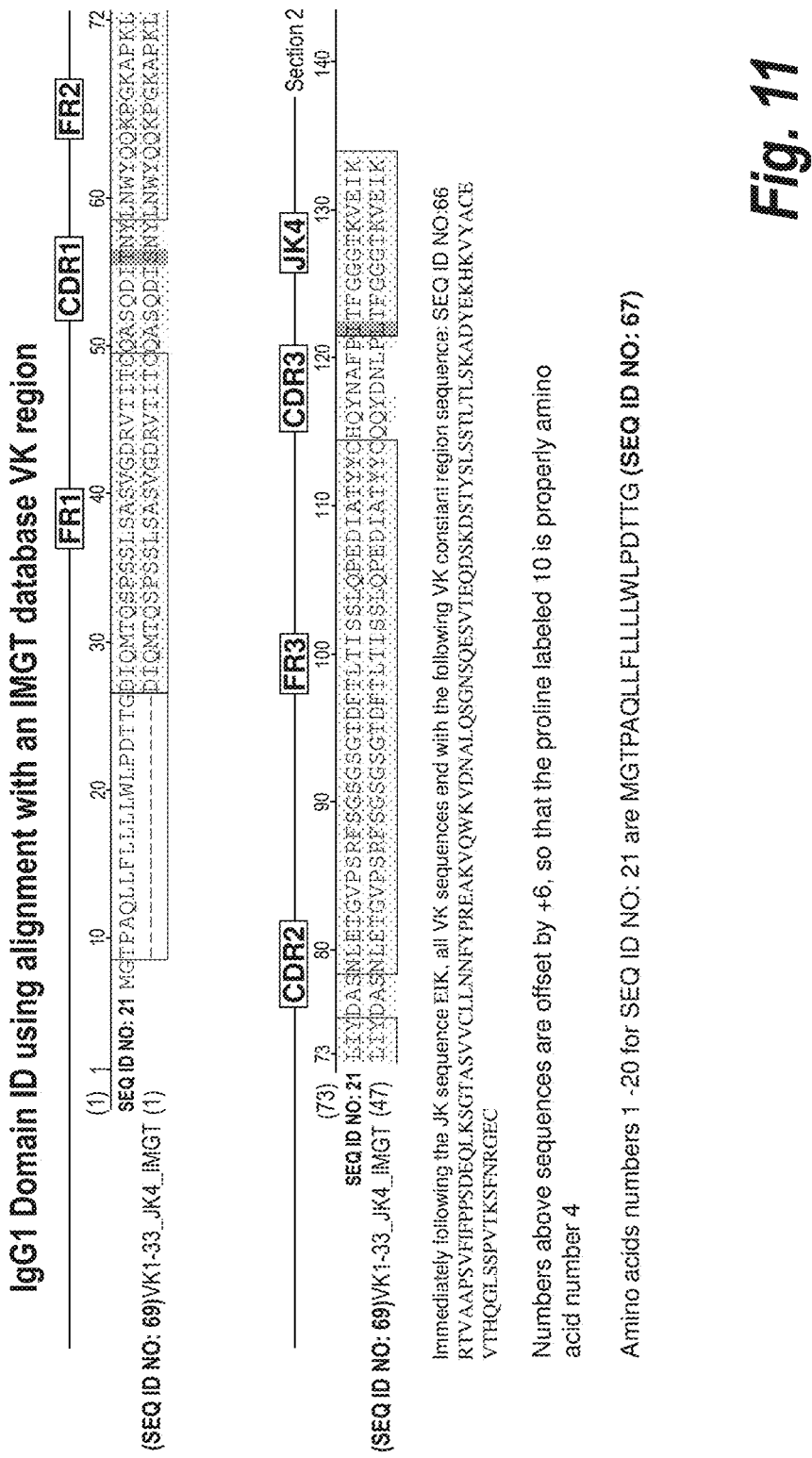
FIG. 11. Amino acid sequences for the variable light regions comprised by SEQ ID NO:21. Sequences are demarcated to show CDR positions as per the IMGT database. The amino acid sequence for the constant light region is also set forth.
Figure 12:
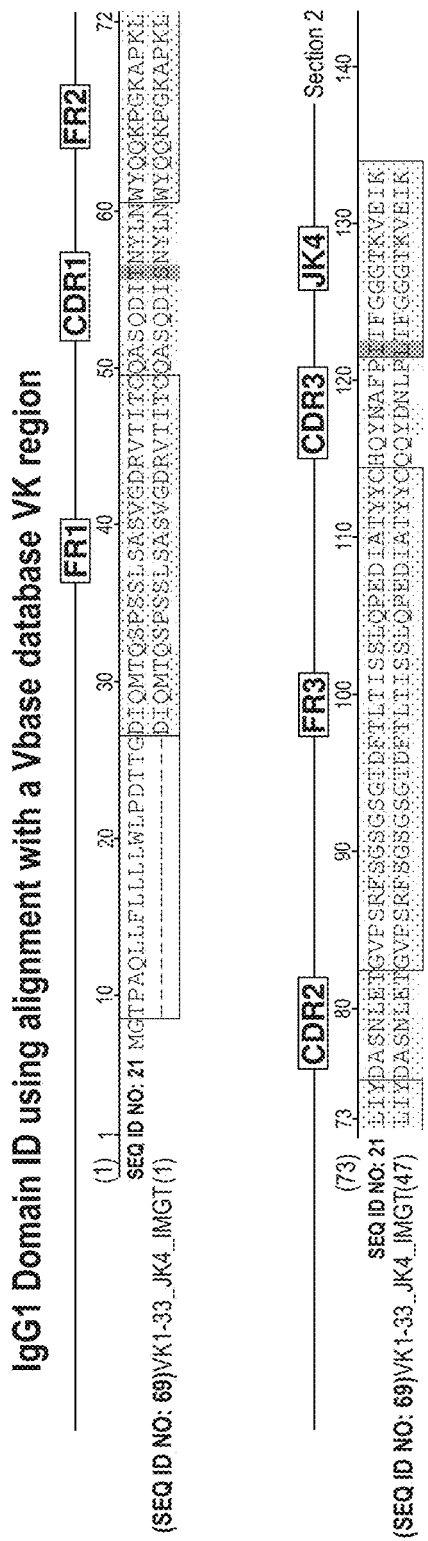
FIG. 12. Amino acid sequences for the variable light regions comprised by SEQ ID NO:21. Sequences are demarcated to show CDR positions as per the Vbase database. The amino acid sequence for the constant light region is also set forth.
Figure 13:
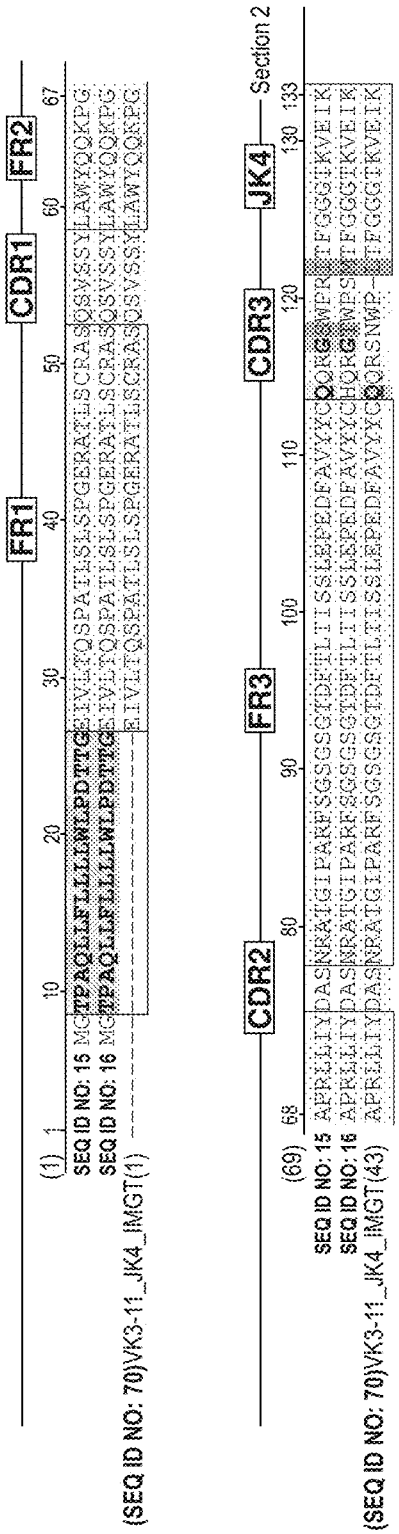
FIG. 13. Amino acid sequences for the variable light comprised by SEQ ID NO:15 and SEQ ID NO:16. Sequences are demarcated to show CDR positions as per the IMGT database. The amino acid sequence for the constant light region is also set forth.
Figure 15:
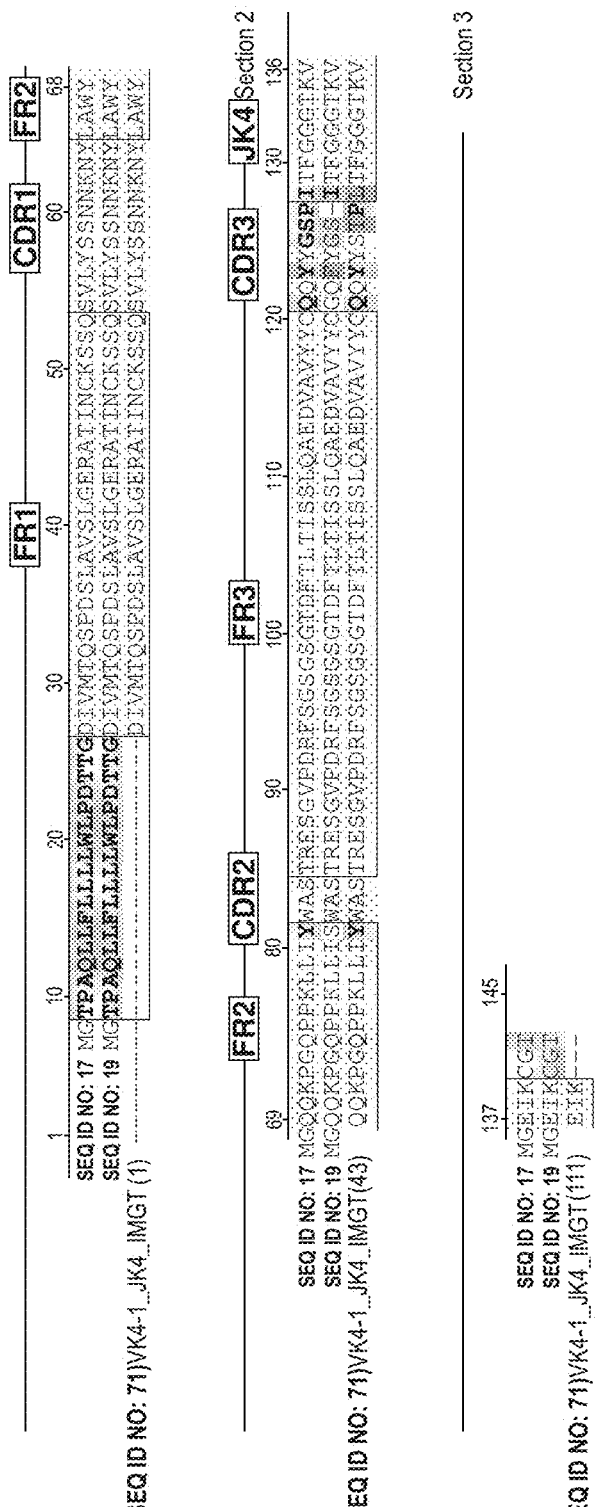
FIG. 15. Amino acid sequences for the variable light regions comprised by SEQ ID NO:17 and SEQ ID NO:19. Sequences are demarcated to show CDR positions as per the IMGT database. The amino acid sequence for the constant light region is also set forth.

The terms "EGFR," "ErbB1," and "EGF receptor" are used interchangeably herein to refer to human EGFR protein; see UniProtKB/Swiss-Prot entry P00533 (SEQ ID NO:57).

The term "inhibition" as used herein, refers to any statistically significant decrease in biological activity, including full blocking of the activity. For example, "inhibition" can refer to a statistically significant decrease of about 10%, 20%, 30%, 40%, 50%, 60%, 70%, 80%, 90%, or about 100% in biological activity.

Inhibition of phosphorylation, as used herein, refers to the ability of an antibody to statistically significantly decrease the phosphorylation of a substrate protein relative to the signaling in the absence of the antibody (control). As is known in the art, intracellular signaling pathways include, for example, phosphoinositide 3'-kinase/Akt (PI3K/Akt/PTEN or "AKT") and/or mitogen-activated protein kinase (MAPK/ERK or "ERK") pathways. As is also known in the art, EGFR mediated signaling can be measured by assaying for the level phosphorylation of the substrate (e.g., phosphorylation or no phosphorylation of AKT and/or ERK). Accordingly, in one embodiment, anti-EGFR antibodies of the present invention provide statistically significant inhibition of the level of phosphorylation of either or both of AKT and ERK by at least 10%, or at least 20%, or at least 30%, or at least 40%, or at least 50%, or at least 60%, or at least 70%, or at least 80%, or at least 90%, or about 100% relative to the level of phosphorylation of AKT and/or ERK in the absence of such antibody (control). Such EGFR mediated signaling can be measured using art recognized techniques which measure a protein in a cellular cascade involving EGFR, e.g., ELISA, Western, or multiplex methods, such as Luminex®.

The phrase "inhibition of the growth of cells expressing EGFR," as used herein, refers to the ability of an antibody to statistically significantly decrease the growth of a cell expressing EGFR relative to the growth of the cell in the absence of the antibody (control) either in vivo or in vitro. In one embodiment, the growth of a cell expressing EGFR (e.g., a cancer cell) may be decreased by at least 10%, or at least 20%, or at least 30%, or at least 40%, or at least 50%, or at least 60%, or at least 70%, or at least 80%, or at least 90%, or about 100% when the cells are contacted with the antibody of the present invention, relative to the growth measured in the absence of the antibody (control). Cellular growth can be assayed using art recognized techniques which measure the rate of cell division, the fraction of cells within a cell population undergoing cell division, and/or the rate of cell loss from a cell population due to terminal differentiation or cell death (e.g., using a cell titer glow assay or thymidine incorporation).

The phrase "inhibition of an EGFR ligand binding to EGFR," as used herein, refers to the ability of an antibody to statistically significantly decrease the binding of an EGFR ligand to its receptor, EGFR, relative to the EGFR ligand binding in the absence of the antibody (control). This means that, in the presence of the antibody, the amount of the EGFR ligand that binds to EGFR relative to a control (no antibody), is statistically significantly decreased. The amount of an EGFR ligand which binds EGFR may be decreased in the presence of an antibody of the invention by at least 10%, or at least 20%, or at least 30%, or at least 40%, or at least 50%, or at least 60%, or at least 70%, or at least 80%, or at least 90%, or about 100% relative to the amount in the absence of the antibody (control). A decrease in EGFR ligand binding can be measured using art-recognized techniques that measure the level of binding of labeled EGFR ligand (e.g., radiolabelled EGF or radiolabeled betacellulin) to cells expressing EGFR in the presence or absence (control) of the antibody.

The phrase "inhibition of EGFR dimerization," as used herein, refers to the ability of an antibody to statistically significantly decrease EGFR dimerization (pairing with another ErbB receptor to form homodimers, e.g., ErbB1/ErbB1 pairings, or heterodimers, e.g., ErbB1/ErbB3 pairings) relative to EGFR dimerization in the absence of the antibody (control). In one embodiment, dimerization of EGFR may be decreased by at least 10%, or at least 20%, or at least 30%, or at least 40%, or at least 50%, or at least 60%, or at least 70%, or at least 80%, or at least 90%, or about 100% when cells expressing EGFR are contacted with the antibody of the present invention, relative to dimerization of EGFR measured in the absence of the antibody (control). A decrease in EGFR dimerization can be measured using art-recognized techniques that measure the level of EGFR dimerization in the presence or absence (control) of the antibody.

The phrase "downregulation of EGFR expression," as used herein, refers to the ability of an antibody to statistically significantly decrease the expression of EGFR on a cell surface, for example, by increasing internalization of EGFR relative to EGFR expression in the absence of the antibody (control). In one embodiment, expression of EGFR may be decreased by at least 10%, or at least 20%, or at least 30%, or at least 40%, or at least 50%, or at least 60%, or at least 70%, or at least 80%, or at least 90%, or about 100% when cells expressing EGFR are contacted with the antibody of the present invention, relative to expression of EGFR on the cell surface measured in the absence of the antibody (control). Downregulation of EGFR expression on a cell surface includes, for example, an increase in internalization/recycling of the receptor, and/or an increase in internalization/degradation of the receptor. An increase in EGFR internalization can be measured using art-recognized techniques that measure the level of EGFR internalization in the presence or absence (control) of the antibody.

With respect to combinations of EGFR antibodies (described herein), the words "additive" or "additivity," as used herein, refer to the activity of two or more antibodies wherein their combined activity (relative to a particular function, e.g., inhibition of cell growth) is equal to the sum of their individual activities. That is, the sum of the activities of two or more antibodies provided herein, when acting individually on a cell expressing EGFR, is approximately equivalent to the combined effect of the same antibodies acting together on the same cell. In one embodiment, the additive effect is measured with respect to any of the properties discussed above (e.g., inhibition of AKT or ERK phosphorylation, inhibition of the growth of cells expressing EGFR, etc.).

The words "synergy" or "synergistic," as used herein, refer to the activity of two or more antibodies wherein their combined activity (relative to a particular function, e.g., inhibition of cell growth) is greater than the expected additive effect of their individual activities. For example, the expected additive effect can be defined according to Bliss independence criteria. In accordance with the Bliss criteria, the effect of two or more drugs (e.g., antibodies) is equal to the sum of the effects of the individual drugs minus the multiplication of the effects of the individual drugs:

$$E12 = E1 + E2 - E1*E2$$

where E1 is the % inhibition by drug 1, E2 is the % inhibition by drug 2, and E12 is the expected % inhibition by the combination.

The synergistic effect can apply to any of the properties discussed herein (e.g., inhibition of EGFR-dependant AKT or ERK phosphorylation, inhibition of the growth of cells expressing EGFR, etc.). In a particular embodiment, at least 10%, or at least 20%, or at least 30%, or at least 40%, or at least 50%, or at least 60%, or at least 70%, or at least 80%, or at least 90%, or greater increase in activity of the combined antibodies relative to the additive effect of their individual activities is achieved.

The term "antibody" or "immunoglobulin," as used interchangeably herein, includes whole antibodies and any antigen binding fragment (antigen-binding portion) or single chain cognates thereof. An "antibody" comprises at least one heavy (H) chain and one light (L) chain. In naturally occurring IgGs, for example, these heavy and light chains are inter-connected by disulfide bonds and there are two paired heavy and light chains, these two also inter-connected by disulfide bonds. Each heavy chain is comprised of a heavy chain variable region (abbreviated herein as $V_H$) and a heavy chain constant region. The heavy chain constant region is comprised of three domains, CH1, CH2 and CH3. Each light chain is comprised of a light chain variable region (abbreviated herein as $V_L$) and a light chain constant region. The light chain constant region is comprised of one domain, CL. The $V_H$ and $V_L$ regions can be further subdivided into regions of hypervariability, termed complementarity determining regions (CDR), interspersed with regions that are more conserved, termed framework regions (FR) or Joining (J) regions (JH or JL in heavy and light chains respectively). Each $V_H$ and $V_L$ is composed of three CDRs three FRs and a J domain, arranged from amino-terminus to carboxy-terminus in the following order: FR1, CDR1, FR2, CDR2, FR3, CDR3, J. The variable regions of the heavy and light chains bind with an antigen. The constant regions of the antibodies may mediate the binding of the immunoglobulin to host tissues or factors, including various cells of the immune system (e.g., effector cells) or humoral factors such as the first component (Clq) of the classical complement system. one or more fragments of an antibody that retain the ability to specifically bind to an antigen (e.g., EGFR). It has been shown that fragments of a full-length antibody can perform the antigen-binding function of an antibody. Examples of binding fragments denoted as an antigen-binding portion or fragment of an antibody include (i) a Fab fragment, a monovalent fragment consisting of the $V_L$, $V_H$, CL and CH1 domains; (ii) a F(ab')$_2$ fragment, a bivalent fragment comprising two Fab fragments linked by a disulfide bridge at the hinge region; (iii) a Fd fragment consisting of the $V_H$ and CH1 domains; (iv) a Fv fragment consisting of the $V_L$ and $V_H$ domains of a single arm of an antibody, (v) a dAb including VH and VL domains; (vi) a dAb fragment (Ward et al. (1989) *Nature* 341, 544-546), which consists of a $V_H$ domain; (vii) a dAb which consists of a VH or a VL domain; and (viii) an isolated complementarity determining region (CDR) or (ix) a combination of two or more isolated CDRs which may optionally be joined by a synthetic linker. Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions are paired to form monovalent molecules (such a single chain cognate of an immunoglobulin fragment is known as a single chain Fv (scFv). Such single chain antibodies are also intended to be encompassed within the term "antibody". Antibody fragments are obtained using conventional techniques known to those with skill in the art, and the fragments are screened for utility in the same general manner as are intact antibodies. Antigen-binding portions can be produced by recombinant DNA techniques, or by enzymatic or chemical cleavage of intact immunoglobulins.

The term "monoclonal antibody" as used herein refers to an antibody obtained from a population of substantially homogeneous antibodies, i.e., the individual antibodies comprising the population are identical except for possible naturally occurring mutations that may be present in minor amounts. Antigen binding fragments (including scFvs) of such immunoglobulins are also encompassed by the term "monoclonal antibody" as used herein. Monoclonal antibodies are highly specific, being directed against a single antigenic site. Furthermore, in contrast to conventional (polyclonal) antibody preparations, which typically include different antibodies, directed against different determinants (epitopes), each monoclonal antibody is directed against a single determinant on the antigen. Monoclonal antibodies can be prepared using any art recognized technique and those described herein such as, for example, a hybridoma method, a transgenic animal, recombinant DNA methods (see, e.g., U.S. Pat. No. 4,816,567), or using phage antibody libraries using the techniques described in, for example, U.S. Pat. No. 7,388,088 and U.S. patent application Ser. No. 09/856,907 (PCT Int. Pub. No. WO 00/31246). Monoclonal antibodies include chimeric antibodies, human antibodies and humanized antibodies and may occur naturally or be produced recombinantly.

The term "recombinant antibody," refers to antibodies that are prepared, expressed, created or isolated by recombinant means, such as (a) antibodies isolated from an animal (e.g., a mouse) that is transgenic or transchromosomal for immunoglobulin genes (e.g., human immunoglobulin genes) or a hybridoma prepared therefrom, (b) antibodies isolated from a host cell transformed to express the antibody, e.g., from a transfectoma, (c) antibodies isolated from a recombinant, combinatorial antibody library (e.g., containing human antibody sequences) using phage display, and (d) antibodies prepared, expressed, created or isolated by any other means that involve splicing of immunoglobulin gene sequences (e.g., human immunoglobulin genes) to other DNA sequences. Such recombinant antibodies may have variable and constant regions derived from human germline immunoglobulin sequences. In certain embodiments, however, such recombinant human antibodies can be subjected to in vitro mutagenesis and thus the amino acid sequences of the $V_H$ and $V_L$ regions of the recombinant antibodies are sequences that, while derived from and related to human germline $V_H$ and $V_L$ sequences, may not naturally exist within the human antibody germline repertoire in vivo.

The term "chimeric immunoglobulin" or antibody refers to an immunoglobulin or antibody whose variable regions derive from a first species and whose constant regions derive from a second species. Chimeric immunoglobulins or antibodies can be constructed, for example by genetic engineering, from immunoglobulin gene segments belonging to different species.

The term "human antibody," as used herein, is intended to include antibodies having variable regions in which both the framework and CDR regions are derived from human germline immunoglobulin sequences as described, for example, by Kabat et al. (See Kabat, et al. (1991) *Sequences of proteins of Immunological Interest, Fifth Edition*, U.S. Department of Health and Human Services, NIH Publication No. 91-3242). Furthermore, if the antibody contains a constant region, the constant region also is derived from human germline immunoglobulin sequences. The human antibodies may include amino acid residues not encoded by human germline immunoglobulin sequences (e.g., mutations introduced by random or site-specific mutagenesis in vitro or by somatic mutation in vivo). However, the term "human antibody", as used herein, is not intended to include antibodies in which CDR sequences derived from the germline of another mammalian species, such as a mouse, have been grafted onto human framework sequences.

The human antibody can have at least one or more amino acids replaced with an amino acid residue, e.g., an activity enhancing amino acid residue that is not encoded by the human germline immunoglobulin sequence. Typically, the human antibody can have up to twenty positions replaced with amino acid residues that are not part of the human germline immunoglobulin sequence. In a particular embodiment, these replacements are within the CDR regions as described in detail below.

The term "humanized immunoglobulin" or "humanized antibody" refers to an immunoglobulin or antibody that includes at least one humanized immunoglobulin or antibody chain (i.e., at least one humanized light or heavy chain). The term "humanized immunoglobulin chain" or "humanized antibody chain" (i.e., a "humanized immunoglobulin light chain" or "humanized immunoglobulin heavy chain") refers to an immunoglobulin or antibody chain (i.e., a light or heavy chain, respectively) having a variable region that includes a variable framework region substantially from a human immunoglobulin or antibody and complementarity determining regions (CDRs) (e.g., at least one CDR, two CDRs, or three CDRs) substantially from a non-human immunoglobulin or antibody, and further includes constant regions (e.g., one constant region or portion thereof, in the case of a light chain, and preferably three constant regions in the case of a heavy chain). The term "humanized variable region" (e.g., "humanized light chain variable region" or "humanized heavy chain variable region") refers to a variable region that includes a variable framework region substantially from a human immunoglobulin or antibody and complementarity determining regions (CDRs) substantially from a non-human immunoglobulin or antibody.

A "bispecific" or "bifunctional antibody" is an artificial hybrid antibody having two different paired heavy and light chains and two different binding sites. Bispecific antibodies can be produced by a variety of methods including fusion of hybridomas or linking of Fab' fragments. In a particular embodiment, a bispecific antibody according to the present invention includes binding sites for both EGFR and a binding site for anther ErbB receptor (i.e., ErbB2, ERbB3, or ErbB4), or any of the FGF receptors.

As used herein, a "heterologous antibody" is defined in relation to the transgenic non-human organism or plant producing such an antibody.

An "isolated antibody," as used herein, is intended to refer to an antibody that is substantially free of other antibodies having different antigenic specificities (e.g., an isolated antibody that specifically binds to EGFR is substantially free of antibodies that specifically bind antigens other than EGFR). In addition, an isolated antibody is typically substantially free of other cellular material and/or chemicals. In one embodiment of the invention, a combination of "isolated" monoclonal antibodies having different EGFR binding specificities are combined in a well-defined composition.

As used herein, "isotype" refers to the antibody class (e.g., IgM or IgG1) that is encoded by heavy chain constant region genes. In some embodiments, a monoclonal antibody of the invention is of the IgG1 isotype. In other embodiments, a monoclonal antibody of the invention is of the IgG2 isotype.

As used herein, "isotype switching" refers to the phenomenon by which the class, or isotype, of an antibody changes from one Ig class or isotype to one of the other Ig classes or isotypes.

As used herein, "nonswitched isotype" refers to the isotypic class of heavy chain that is produced when no isotype switching has taken place; the CH gene encoding the nonswitched isotype is typically the first CH gene immediately downstream from the functionally rearranged VDJ gene. Isotype switching has been classified as classical or non-classical isotype switching. Classical isotype switching occurs by recombination events that involve at least one switch sequence region in a gene encoding an antibody. Non-classical isotype switching may occur by, for example, homologous recombination between human $\sigma_\mu$ and human $\Sigma_\mu$ (δ-associated deletion). Alternative non-classical switching mechanisms, such as intertransgene and/or interchromosomal recombination, among others, may occur and effectuate isotype switching.

The term "switch sequence" refers to those DNA sequences responsible for switch recombination. A "switch donor" sequence, typically a µ switch region, will be 5' (i.e., upstream) of the construct region to be deleted during the switch recombination. The "switch acceptor" region will be between the construct region to be deleted and the replacement constant region (e.g., γ, ε, etc.). As there is no specific site where recombination always occurs, the final gene sequence will typically not be predictable from the construct.

An "antigen" is an entity (e.g., a proteinaceous entity or peptide) to which an antibody binds. In various embodiments of the present invention, an antigen is EGF. In a particular embodiment according to the invention, an antigen is human EGFR.

The term "epitope" or "antigenic determinant" refers to a site on an antigen to which an immunoglobulin or antibody specifically binds. Epitopes can be formed both from contiguous amino acids or noncontiguous amino acids juxtaposed by tertiary folding of a protein. Epitopes formed from contiguous amino acids are typically retained on exposure to denaturing solvents, whereas epitopes formed by tertiary folding are typically lost on treatment with denaturing solvents. An epitope typically includes at least 3, 4, 5, 6, 7, 8, 9, 10, 11, 12, 13, 14 or 15 amino acids, often contiguous amino acids, in a unique spatial conformation. Methods for determining what epitopes are bound by a given antibody (i.e., epitope mapping) are well known in the art and include, for example, immunoblotting and immunoprecipitation assays, wherein overlapping or contiguous peptides from EGFR are tested for reactivity with the given anti-EGFR antibody. Methods of determining spatial conformation of epitopes are also well known in the art and include, for example, x-ray crystallography and 2- or more dimensional nuclear magnetic resonance.

Accordingly, also encompassed by the present invention are antibodies that bind to an epitope on EGFR which comprise all or a portion of an epitope recognized by the particular antibodies described herein (e.g., the same or an overlapping region or a region between or spanning the region). In another embodiment, the invention provides antibodies that compete for binding to EGFR with the antibodies described herein. Competing antibodies and antibodies that recognize the same or an overlapping epitope can be identified using routine techniques such as an immunoassay, for example, by showing the ability of one antibody to block the binding of another antibody to a target antigen, i.e., a competitive binding assay. Competitive binding may be determined using an assay such as described in the Examples below.

The terms "specific binding," "specifically binds," "selective binding," and "selectively binds," mean that an antibody exhibits appreciable affinity for a particular antigen or epitope and, generally, does not exhibit significant cross-reactivity with other antigens and epitopes. "Appreciable" or preferred binding includes binding with a $K_D$ of $10^6$, $10^7$, $10^8$, $10^9$, or $10^{10}$ $M^{-1}$ or better. The $K_D$ of an antibody antigen interaction (the affinity constant) indicates the concentration of antibody at which 50% of antibody and antigen molecules are bound together. $K_D$ is a ratio of the association constant, $k_a$ and the dissociation constant, $k_d$, i.e., $K_D = k_d/k_a$. Thus, at a suitable fixed antigen concentration, 50% of a higher (i.e., stronger) affinity antibody will bind antigen molecules at a lower antibody concentration than would be required to achieve the same percent binding with a lower affinity antibody. Thus a lower $K_D$ value indicates a higher (stronger) affinity. As used herein, "better" affinities are stronger affinities, and are of lower numeric value than their comparators, with a $K_D$ of $10^7 M^{-1}$ being of lower numeric value and therefore representing a better affinity than a $K_D$ of $10^6 M^{-1}$. Affinities better (i.e., with a lower $K_D$ value and therefore stronger) than $10^7 M^{-1}$, preferably better than $10^8 M^{-1}$, are generally preferred. Values intermediate to those set forth herein are also contemplated, and a preferred binding affinity can be indicated as a range of affinities, for example preferred binding affinities for anti-EGFR antibodies disclosed herein are, $10^6$ to $10^{12} M^{-1}$, preferably $10^7$ to $10^{12} M^{-1}$, more preferably $10^8$ to $10^{12}$ $M^{-1}$. An antibody that "does not exhibit significant cross-reactivity" is one that will not appreciably bind to an off target antigen (e.g., a non-EGFR protein). For example, in one embodiment, an antibody that specifically binds to EGFR will exhibit at least a two, and preferably three, or four or more orders of magnitude better binding affinity (i.e., binding exhibiting a two, three, or four or more orders of magnitude lower $K_D$ value) for EGFR than for ErbB molecules other than ErbB1 (EGFR) or for non-ErbB proteins or peptides. Specific or selective binding can be determined according to any art-recognized means for determining such binding, including, for example, according to Scatchard analysis and/or competitive (competition) binding assays as described herein.

The term "$K_D$," as used herein, is intended to refer to the dissociation equilibrium constant of a particular antibody-antigen interaction or the affinity of an antibody for an antigen. In one embodiment, the antibody according to the present invention binds an antigen (e.g., EGFR) with an affinity ($K_D$) of 100 nM or better (i.e., or less) (e.g., 90 nM, 80 nM, 70 nM, 60 nM, 50 nM, 40 nM, 30 nM, 20 nM, or 10 nM or less), as measured using a surface plasmon resonance assay, a cell binding assay, or an equilibrium dialysis assay. In a particular embodiment, an antibody binds EGFR with an affinity (as represented by dissociation constant $K_D$) of 8 nM or better (e.g., 7 nM, 6 nM, 5 nM, 4 nM, 2 nM, 1.5 nM, 1.4 nM, 1.3 nM, 1.2 nM, 1.1 nM, 1 nM or lower), as measured by a surface plasmon resonance assay or a cell binding assay. In other embodiments, an antibody binds an antigen (e.g., EGFR) with an affinity ($K_D$) of approximately less than $10^{-7}M$, such as approximately less than $10^{-8}M$, $10^{-9}M$ or $10^{-10}M$ or even lower when determined by surface plasmon resonance (SPR) technology in a BIACORE 3000 instrument using recombinant EGFR as the analyte and the antibody as the ligand, and binds to the predetermined antigen with an affinity that is at least two-fold greater than its affinity for binding to a non-specific antigen (e.g., BSA, casein) other than the predetermined antigen or a closely-related antigen. Other methods for determining $K_D$ include equilibrium binding to live cells expressing EGFR via flow cytometry (FACS) or in solution using KinExA® technology.

The term "$K_{off}$," as used herein, is intended to refer to the off rate constant for the dissociation of an antibody from the antibody/antigen complex.

The terms "IC50" and "IC90," as used herein, refer to the measure of the effectiveness of a compound (e.g., an anti-EGFR antibody) in inhibiting a biological or biochemical function (e.g., the function or activity of EGFR) by 50% and 90%, respectively. For example, IC50 indicates how much of an anti-EGFR antibody is needed to inhibit the activity of EGFR (e.g., the growth of a cell expressing EGFR) by half. That is, it is the half maximal (50%) inhibitory concentration (IC) of an anti-EGFR antibody (50% IC, or $IC_{50}$). According to the FDA, IC50 represents the concentration of a drug that is required for 50% inhibition in vitro. The IC50 and IC90 can be determined by techniques known in the art, for example, by constructing a dose-response curve and examining the effect of different concentrations of the antagonist (i.e., the anti-EGFR antibody) on reversing EGFR activity.

As used herein, "glycosylation pattern" is defined as the pattern of carbohydrate units that are covalently attached to a protein, more specifically to an immunoglobulin protein.

The term "rearranged" as used herein refers to a configuration of a heavy chain or light chain immunoglobulin locus wherein a V segment is positioned immediately adjacent to a D-J or J segment in a conformation encoding essentially a complete $V_H$ or $V_L$ domain, respectively. A rearranged immunoglobulin gene locus can be identified by comparison to germline DNA; a rearranged locus will have at least one recombined heptamer/nonamer homology element.

The term "unrearranged" or "germline configuration" as used herein in reference to a V segment refers to the configuration wherein the V segment is not recombined so as to be immediately adjacent to a D or J segment.

The term "nucleic acid molecule," as used herein, is intended to include DNA molecules and RNA molecules. A nucleic acid molecule may be single-stranded or double-stranded, but preferably is double-stranded DNA.

The term "isolated nucleic acid molecule," as used herein in reference to nucleic acids encoding antibodies or antibody fragments (e.g., $V_H$, $V_L$, CDR3), is intended to refer to a nucleic acid molecule in which the nucleotide sequences are free of other genomic nucleotide sequences, e.g., those encoding antibodies that bind antigens other than EGFR, which other sequences may naturally flank the nucleic acid in human genomic DNA.

The term "modifying," or "modification," as used herein, is intended to refer to changing one or more amino acids in the antibodies or antigen-binding portions thereof. The change can be produced by adding, substituting or deleting an amino acid at one or more positions. The change can be produced using known techniques, such as PCR mutagenesis. For example, in some embodiments, an antibody or an antigen-binding portion thereof identified using the methods of the invention can be modified, to thereby modify the binding affinity of the antibody or antigen-binding portion thereof to EGFR. "Conservative amino acid substitutions" in the sequences of the antibodies are provided, i.e., nucleotide and amino acid sequence modifications which do not abrogate the binding of the antibody encoded by the nucleotide sequence or containing the amino acid sequence, to the antigen, i.e., EGFR. Conservative amino acid substitutions include the substitution of an amino acid in one class by an amino acid of the same class, where a class is defined by common physicochemical amino acid side chain properties and high substitution frequencies in homologous proteins found in nature, as determined, for example, by a standard Dayhoff frequency exchange matrix or BLOSUM matrix. Six general classes of amino acid side chains have been categorized and include: Class I (Cys); Class II (Ser, Thr, Pro, Ala, Gly); Class III (Asn, Asp, Gln, Glu); Class IV (His, Arg, Lys); Class V (Ile, Leu, Val, Met); and Class VI (Phe, Tyr, Trp). For example, substitution of an Asp for another class III residue such as Asn, Gln, or Glu, is a conservative substitution. Thus, a predicted non-essential amino acid residue in an anti-EGFR antibody is preferably replaced with another amino acid residue from the same class. Methods of identifying nucleotide and amino acid conservative substitutions which do not eliminate antigen binding are well-known in the art.

The term "non-conservative amino acid substitution" refers to the substitution of an amino acid in one class with an amino acid from another class; for example, substitution of an Ala, a class II residue, with a class III residue such as Asp, Asn, Glu, or Gln.

Alternatively, in another embodiment, mutations (conservative or non-conservative) can be introduced randomly along all or part of an anti-EGFR antibody coding sequence, such as by saturation mutagenesis, and the resulting modified anti-EGFR antibodies can be screened for binding activity.

A "consensus sequence" is a sequence formed from the most frequently occurring amino acids (or nucleotides) in a family of related sequences. In a family of proteins, each position in the consensus sequence is occupied by the amino acid occurring most frequently at that position in the family. If two amino acids occur equally frequently, either can be included in the consensus sequence. A "consensus framework" of an immunoglobulin refers to a framework region in the consensus immunoglobulin sequence. Similarly, the consensus sequence for the CDRs of can be derived by optimal alignment of the CDR amino acid sequences of EGFR antibodies of the present invention.

For nucleic acids, the term "substantial homology" indicates that two nucleic acids, or designated sequences thereof, when optimally aligned and compared, are identical, with appropriate nucleotide insertions or deletions, in at least about 80% of the nucleotides, usually at least about 90% to 95%, and more preferably at least about 98% to 99.5% of the nucleotides. Alternatively, substantial homology exists when the segments will hybridize under selective hybridization conditions, to the complement of the strand.

The nucleic acids may be present in whole cells, in a cell lysate, or in a partially purified or substantially pure form. A nucleic acid is "isolated" or "rendered substantially pure" when purified away from other cellular components or other contaminants, e.g., other cellular nucleic acids or proteins, by standard techniques, including alkaline/SDS treatment, CsCl banding, column chromatography, agarose gel electrophoresis and others well known in the art.

The nucleic acid compositions, while often comprising a native sequence (except for modified restriction sites and the like), from either cDNA, genomic or mixtures thereof may alternately be mutated, in accordance with standard techniques to provide altered gene sequences. For coding sequences, these mutations, may modify the encoded amino acid sequence as desired. In particular, DNA sequences substantially homologous to native V, D, J, constant, switches and other such sequences described herein are contemplated.

The term "operably linked" refers to a nucleic acid sequence placed into a functional relationship with another nucleic acid sequence. For example, DNA for a presequence or secretory leader is operably linked to DNA for a polypeptide if it is expressed as a pre-protein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice. A nucleic acid is "operably linked" when it is placed into a functional relationship with another nucleic acid sequence. For instance, a promoter or enhancer is operably linked to a coding sequence if it affects the transcription of the sequence. With respect to transcription regulatory sequences, operably linked means that the DNA sequences being linked are contiguous and, where necessary to join two protein coding regions, contiguous and in reading frame. For switch sequences, operably linked indicates that the sequences are capable of effecting switch recombination.

The term "vector," as used herein, is intended to refer to a nucleic acid molecule capable of transporting another nucleic acid to which it has been linked. One type of vector is a "plasmid," which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. The terms, "plasmid" and "vector" may be used interchangeably. However, other forms of expression vectors, such as viral vectors (e.g., replication defective retroviruses, adenoviruses and adeno-associated viruses), which serve equivalent functions are also contemplated.

The term "recombinant host cell" (or simply "host cell"), as used herein, is intended to refer to a cell into which a recombinant expression vector has been introduced. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein.

The terms "treat," "treating," and "treatment," as used herein, refer to therapeutic or preventative measures described herein. The methods of "treatment" employ administration to a subject, an antibody or antibody pair or trio disclosed herein, for example, a subject having a disease or disorder associated with EGFR dependent signaling or predisposed to having such a disease or disorder, in order to prevent, cure, delay, reduce the severity of, or ameliorate one or more symptoms of the disease or disorder or recurring disease or disorder, or in order to prolong the survival of a subject beyond that expected in the absence of such treatment.

The term "disease associated with EGFR dependent signaling," or "disorder associated with EGFR dependent signaling," as used herein, includes disease states and/or symptoms associated with a disease state, where increased levels of EGFR and/or activation of cellular cascades involving EGFR are found. The term "disease associated with EGFR dependent signaling," also includes disease states and/or symptoms associated with the activation of alternative EGFR signaling pathways. In general, the term "disease associated with EGFR dependent signaling," refers to any disorder, the onset, progression or the persistence of the symptoms of which requires the participation of EGFR. Exemplary EGFR-mediated disorders include, but are not limited to, for example, cancer.

The terms "cancer" and "cancerous" refer to or describe the physiological condition in mammals that is typically characterized by unregulated cell growth. Examples of cancer include but are not limited to, carcinoma, lymphoma, blastoma, sarcoma, and leukemia. More particular examples of such cancers include squamous cell cancer, small-cell lung cancer, non-small cell lung cancer, gastric cancer, pancreatic cancer, glial cell tumors such as glioblastoma and neurofibromatosis, cervical cancer, ovarian cancer, liver cancer, bladder cancer, hepatoma, breast cancer, colon cancer, melanoma, colorectal cancer, endometrial carcinoma, salivary gland carcinoma, kidney cancer, renal cancer, prostate cancer, vulval cancer, thyroid cancer, hepatic carcinoma and various types of head and neck cancer. In a particular embodiment, a cancer treated or diagnosed using the methods disclosed herein is selected from melanoma, breast cancer, ovarian cancer, renal carcinoma, gastrointestinal/colon cancer, lung cancer, and prostate cancer.

The term "effective amount," as used herein, refers to that amount of an antibody or an antigen binding portion thereof that binds EGFR, which is sufficient to effect treatment, prognosis or diagnosis of a disease associated with EGFR dependent signaling, as described herein, when administered to a subject. Therapeutically effective amounts of antibodies provided herein, when used alone or in combination, will vary depending upon the relative activity of the antibodies and combinations (e.g., in inhibiting cell growth) and depending upon the subject and disease condition being treated, the weight and age of the subject, the severity of the disease condition, the manner of administration and the like, which can readily be determined by one of ordinary skill in the art. The dosages for administration can range from, for example, about 1 ng to about 10,000 mg, about 5 ng to about 9,500 mg, about 10 ng to about 9,000 mg, about 20 ng to about 8,500 mg, about 30 ng to about 7,500 mg, about 40 ng to about 7,000 mg, about 50 ng to about 6,500 mg, about 100 ng to about 6,000 mg, about 200 ng to about 5,500 mg, about 300 ng to about 5,000 mg, about 400 ng to about 4,500 mg, about 500 ng to about 4,000 mg, about 1 µg to about 3,500 mg, about 5 µg to about 3,000 mg, about 10 µg to about 2,600 mg, about 20 µg to about 2,575 mg, about 30 µg to about 2,550 mg, about 40 µg to about 2,500 mg, about 50 µg to about 2,475 mg, about 100 µg to about 2,450 mg, about 200 µg to about 2,425 mg, about 300 µg to about 2,000, about 400 µg to about 1,175 mg, about 500 µg to about 1,150 mg, about 0.5 mg to about 1,125 mg, about 1 mg to about 1,100 mg, about 1.25 mg to about 1,075 mg, about 1.5 mg to about 1,050 mg, about 2.0 mg to about 1,025 mg, about 2.5 mg to about 1,000 mg, about 3.0 mg to about 975 mg, about 3.5 mg to about 950 mg, about 4.0 mg to about 925 mg, about 4.5 mg to about 900 mg, about 5 mg to about 875 mg, about 10 mg to about 850 mg, about 20 mg to about 825 mg, about 30 mg to about 800 mg, about 40 mg to about 775 mg, about 50 mg to about 750 mg, about 100 mg to about 725 mg, about 200 mg to about 700 mg, about 300 mg to about 675 mg, about 400 mg to about 650 mg, about 500 mg, or about 525 mg to about 625 mg, of an antibody. Dosage regiments may be adjusted to provide the optimum therapeutic response. An effective amount is also one in which any toxic or detrimental effects (i.e., side effects) of an antibody are minimized and/or outweighed by the beneficial effects.

The term "therapeutic agent" in intended to encompass any and all compounds that have an ability to decrease or inhibit the severity of the symptoms of a disease or disorder, or increase the frequency and/or duration of symptom-free or symptom-reduced periods in a disease or disorder, or inhibit or prevent impairment or disability due to a disease or disorder affliction, or inhibit or delay progression of a disease or disorder, or inhibit or delay onset of a disease or disorder, or inhibit or prevent infection in an infectious disease or disorder. Non-limiting examples of therapeutic agents include small organic molecules, monoclonal antibodies, bispecific antibodies, recombinantly engineered biologics, RNAi compounds, tyrosine kinase inhibitors, and commercial antibodies. In certain embodiments, tyrosine kinase inhibitors include, e.g., one or more of erlotinib, gefitinib, and lapatinib, which are currently marketed pharmaceuticals. Commercially available pharmaceutical anti-EGFR antibodies include cetuximab and panitumumab. Other pharmaceutical anti-EGFR antibodies include zalutumumab, nimotuzumab, and matuzumab, which are in development.

The term "patient" includes human and other mammalian subjects that receive either prophylactic or therapeutic treatment.

The term "subject" includes any mammal, e.g., a primate. For example, the methods and compositions herein disclosed can be used to treat a subject having cancer. In a particular embodiment, the subject is a human.

The term "sample" refers to tissue, body fluid, or a cell (or a fraction of any of the foregoing) taken from a patient or a subject. Normally, the tissue or cell will be removed from the patient, but in vivo diagnosis is also contemplated. In the case of a solid tumor, a tissue sample can be taken from a surgically removed tumor and prepared for testing by conventional techniques. In the case of lymphomas and leukemias, lymphocytes, leukemic cells, or lymph tissues can be obtained (e.g., leukemic cells from blood) and appropriately prepared. Other samples, including urine, tears, serum, plasma, cerebrospinal fluid, feces, sputum, cell extracts etc. can also be useful for particular cancers.

Various aspects of the disclosure are described in further detail in the following subsections.

II. Methods for Producing Antibodies (i) Monoclonal Antibodies

Monoclonal antibodies can be produced using a variety of known techniques, such as the standard somatic cell hybridization technique, viral or oncogenic transformation of B lymphocytes, or yeast or phage display techniques using libraries of human antibody genes. In particular embodiments, the antibodies are fully human monoclonal antibodies.

Accordingly, in one embodiment, a hybridoma method is used for producing an antibody that binds EGFR. In this method, a mouse or other appropriate host animal can be immunized with a suitable antigen in order to elicit lymphocytes that produce or are capable of producing antibodies that will specifically bind to the antigen used for immunization. Alternatively, lymphocytes may be immunized in vitro. Lymphocytes can then be fused with myeloma cells using a suitable fusing agent, such as polyethylene glycol, to form a hybridoma cell. Culture medium in which hybridoma cells are growing is assayed for production of monoclonal antibodies directed against the antigen. After hybridoma cells are identified that produce antibodies of the desired specificity, affinity, and/or activity, the clones may be subcloned by limiting dilution procedures and grown by standard methods. Suitable culture media for this purpose include, for example, D-MEM or RPMI-1640 medium. In addition, the hybridoma cells may be grown in vivo as ascites tumors in an animal. The monoclonal antibodies secreted by the subclones can be separated from the culture medium, ascites fluid, or serum by conventional immunoglobulin purification procedures such as, for example, protein A-Sepharose, hydroxylapatite chromatography, gel electrophoresis, dialysis, or affinity chromatography.

In another embodiment, antibodies that bind EGFR can be isolated from antibody libraries generated using well know techniques such as those described in, for example, U.S. Pat. Nos. 5,223,409; 5,403,484; and 5,571,698 to Ladner et al.; U.S. Pat. Nos. 5,427,908 and 5,580,717 to Dower et al.; U.S. Pat. Nos. 5,969,108 and 6,172,197 to McCafferty et al.; and U.S. Pat. Nos. 5,885,793; 6,521,404; 6,544,731; 6,555,313; 6,582,915 and 6,593,081 to Griffiths et al. Additionally, production of high affinity (nM range) human antibodies by chain shuffling, as well as combinatorial infection and in vivo recombination as a strategy for constructing very large phage libraries may also be used. See, e.g., U.S. patent application Ser. No. 09/856,907 (PCT Int. Pub. No. WO 00/31246)

In a particular embodiment, the monoclonal antibody that binds EGFR is produced using phage display. This technique involves the generation of a human Fab library having a unique combination of immunoglobulin sequences isolated from human donors and having synthetic diversity in the heavy-chain CDRs is generated. The library is then screened for Fabs that bind to EGFR.

In yet another embodiment, human monoclonal antibodies directed against EGFR can be generated using transgenic or transchromosomic mice carrying parts of the human immune system rather than the mouse system (see e.g., U.S. Pat. Nos. 5,545,806; 5,569,825; 5,625,126; 5,633,425; 5,789,650; 5,877,397; 5,661,016; 5,814,318; 5,874,299; and 5,770,429; all to Lonberg and Kay; U.S. Pat. No. 5,545,807 to Surani et al.; PCT Publication Nos. WO 92/03918, WO 93/12227, WO 94/25585, WO 97/13852, WO 98/24884 and WO 99/45962, all to Lonberg and Kay; and PCT Publication No. WO 01/14424 to Korman et al.).

In another embodiment, human antibodies can be raised using a mouse that carries human immunoglobulin sequences on transgenes and transchomosomes, such as a mouse that carries a human heavy chain transgene and a human light chain transchromosome (see e.g., PCT Publication WO 02/43478 to Ishida et al.).

Still further, alternative transgenic animal systems expressing human immunoglobulin genes are available in the art and can be used to raise anti-EGFR antibodies. For example, an alternative transgenic system referred to as the Xenomouse (Abgenix, Inc.) can be used; such mice are described in, for example, U.S. Pat. Nos. 5,939,598; 6,075,181; 6,114,598; 6,150,584 and 6,162,963 to Kucherlapati et al.

Moreover, alternative transchromosomic animal systems expressing human immunoglobulin genes are available in the art and can be used to raise anti-EGFR antibodies. For example, mice carrying both a human heavy chain transchromosome and a human light chain tranchromosome can be used. Furthermore, cows carrying human heavy and light chain transchromosomes have been described in the art and can be used to raise anti-EGFR antibodies.

In yet another embodiment, antibodies can be prepared using a transgenic plant and/or cultured plant cells (such as, for example, tobacco, maize and duckweed) that produce such antibodies. For example, transgenic tobacco leaves expressing antibodies can be used to produce such antibodies by, for example, using an inducible promoter. Also, transgenic maize can be used to express such antibodies and antigen binding portions thereof. Antibodies can also be produced in large amounts from transgenic plant seeds including antibody portions, such as single chain antibodies (scFv's), for example, using tobacco seeds and potato tubers.

The binding specificity of monoclonal antibodies (or portions thereof) that bind EGFR prepared using any technique including those disclosed here, can be determined by immunoprecipitation or by an in vitro binding assay, such as radio-immunoassay (RIA) or enzyme-linked immunoabsorbent assay (ELISA). The binding affinity of a monoclonal antibody or portion thereof also can be determined by Scatchard analysis.

In certain embodiments, an EGFR antibody produced using any of the methods discussed above may be further altered or optimized to achieve a desired binding specificity and/or affinity using art recognized techniques, such as those described herein.

In one embodiment, partial antibody sequences derived from an EGFR antibody may be used to produce structurally and functionally related antibodies. For example, antibodies interact with target antigens predominantly through amino acid residues that are located in the six heavy and light chain complementarity determining regions (CDRs). For this reason, the amino acid sequences within CDRs are more diverse between individual antibodies than sequences outside of CDRs. Because CDR sequences are responsible for most antibody-antigen interactions, it is possible to express recombinant antibodies that mimic the properties of specific naturally occurring antibodies by constructing expression vectors that include CDR sequences from the specific naturally occurring antibody grafted onto framework sequences from a different antibody with different properties. Such framework sequences can be obtained from public DNA databases that include germline antibody gene sequences.

Thus, one or more structural features of an anti-EGFR antibody, such as the CDRs, can be used to create structurally related anti-EGFR antibodies that retain at least one desired functional property, e.g., inhibiting growth of cells expressing EGFR.

In a particular embodiment, one or more CDR regions selected from SEQ ID NOs:23-56 is combined recombinantly with known human framework regions and CDRs to create additional, recombinantly-engineered, anti-EGFR antibodies. The heavy and light chain variable framework regions can be derived from the same or different antibody sequences.

It is well known in the art that antibody heavy and light chain CDR3 domains play a particularly important role in the binding specificity/affinity of an antibody for an antigen. Accordingly, in certain embodiments, antibodies are generated that include the heavy and/or light chain CDR3s of the particular antibodies described herein. The antibodies can further include the heavy and/or light chain CDR1 and/or CDR2s of the antibodies disclosed herein.

The CDR 1, 2, and/or 3 regions of the engineered antibodies described above can comprise the exact amino acid sequence(s) as those disclosed herein. However, the ordinarily skilled artisan will appreciate that some deviation from the exact CDR sequences may be possible, particularly for CDR1 and CDR2 sequences, which can tolerate more variation than CDR3 sequences without altering epitope specificity (such deviations are, e.g., conservative amino acid substitutions). Accordingly, in another embodiment, the engineered antibody may be composed of one or more CDR1s and CDR2s that are, for example, 90%, 95%, 98%, 99% or 99.5% identical to the corresponding CDRs of an antibody named herein.

In another embodiment, one or more residues of a CDR may be altered to modify binding to achieve a more favored on-rate of binding. Using this strategy, an antibody having ultra high binding affinity of, for example, $10^{10}$ M$^{-1}$ or more, can be achieved. Affinity maturation techniques, well known in the art and those described herein, can be used to alter the CDR region(s) followed by screening of the resultant binding molecules for the desired change in binding. Accordingly, as CDR(s) are altered, changes in binding affinity as well as immunogenicity can be monitored and scored such that an antibody optimized for the best combined binding and low immunogenicity are achieved.

Modifications can also be made within one or more of the framework or joining regions of the heavy and/or the light chain variable regions of an antibody, so long as antigen binding affinity subsequent to these modifications is better than $10^6$ M$^{-1}$.

In another embodiment, the antibody is further modified with respect to effector function, so as to enhance the effectiveness of the antibody in treating cancer, for example. For example cysteine residue(s) may be introduced in the Fc region, thereby allowing interchain disulfide bond formation in this region. The homodimeric antibody thus generated may have improved internalization capability and/or increased complement-mediated cell killing and antibody-dependent cellular cytotoxicity (ADCC). Homodimeric antibodies with enhanced anti-tumor activity may also be prepared using heterobifunctional cross-linkers. Alternatively, an antibody can be engineered which has dual Fc regions and may thereby have enhanced complement lysis and ADCC capabilities.

Also provided are bispecific antibodies and immunoconjugates, as discussed below.

(ii) Bispecific Antibodies

Bispecific antibodies herein include at least two binding specificities for EGFR which preferably bind non-overlapping or non-competing epitopes. Such bispecific antibodies can include additional binding specificities, e.g., a third EGFR binding specificity and/or a binding specificity for another ErbB receptor (e.g., ErbB3) or another antigen, such as the product of an oncogene. Bispecific antibodies can be prepared as full length antibodies or antibody fragments (e.g. F(ab')$_2$ bispecific antibodies).

Methods for making bispecific antibodies are well known in the art (see, e.g., WO 05117973 and WO 06091209). For example, production of full length bispecific antibodies can be based on the coexpression of two paired immunoglobulin heavy chain-light chains, where the two chains have different specificities. Various techniques for making and isolating bispecific antibody fragments directly from recombinant cell culture have also been described. For example, bispecific antibodies have been produced using leucine zippers. Another strategy for making bispecific antibody fragments by the use of single-chain Fv (sFv) dimers has also been reported.

In a particular embodiment, the bispecific antibody comprises a first antibody (or binding portion thereof) which binds to EGFR derivatized or linked to another functional molecule, e.g., another peptide or protein (e.g., another antibody or ligand for a receptor) to generate a bispecific molecule that binds to at least two different binding sites or target molecules. An antibody may be derivatized or linked to more than one other functional molecule to generate multispecific molecules that bind to more than two different binding sites and/or target molecules; such multispecific molecules are also intended to be encompassed by the term "bispecific molecule" as used herein. To create a bispecific molecule, an antibody disclosed herein can be functionally linked (e.g., by chemical coupling, genetic fusion, noncovalent association or otherwise) to one or more other binding molecules, such as another antibody, antibody fragment, peptide or binding mimetic, such that a bispecific molecule results.

Accordingly, bispecific molecules comprising at least one first binding specificity for EGFR and a second binding specificity for a second target epitope are contemplated. In a particular embodiment, the second target epitope is an Fc receptor, e.g., human FcγRI (CD64) or a human Fcα receptor (CD89). Therefore, bispecific molecules capable of binding both to FcγR, FcαR or FcεR expressing effector cells (e.g., monocytes, macrophages or polymorphonuclear cells (PMNs)), and to target cells expressing EGFR are also provided. These bispecific molecules target EGFR expressing cells to effector cell and trigger Fc receptor-mediated effector cell activities, such as phagocytosis of an EGFR expressing cells, antibody dependent cell-mediated cytotoxicity (ADCC), cytokine release, or generation of superoxide anion.

In one embodiment, the bispecific molecules comprise as a binding specificity at least one antibody, or an antibody fragment thereof, including, e.g., an Fab, Fab', F(ab')$_2$, Fv, or a single chain Fv. The antibody may also be a light chain or heavy chain dimer, or any minimal fragment thereof such as a Fv or a single chain construct as described in Ladner et al. U.S. Pat. No. 4,946,778.

The bispecific molecules can be prepared by conjugating the constituent binding specificities, e.g., the anti-FcR and anti-EGFR binding specificities, using methods known in the art. For example, each binding specificity of the bispecific molecule can be generated separately and then conjugated to one another. When the binding specificities are proteins or peptides, a variety of coupling or cross-linking agents can be used for covalent conjugation. Examples of cross-linking agents include protein A, carbodiimide, N-succinimidyl-S-acetyl-thioacetate (SATA), 5,5'-dithiobis(2-nitrobenzoic acid) (DTNB), o-phenylenedimaleimide (oPDM), N-succinimidyl-3-(2-pyridyldithio)propionate (SPDP), and sulfosuccinimidyl 4-(N-maleimidomethyl) cyclohaxane-1-carboxylate (sulfo-SMCC). Preferred conjugating agents are SATA and sulfo-SMCC, both available from Pierce Chemical Co. (Rockford, Ill.).

When the binding specificities are antibodies, they can be conjugated via sulfhydryl bonding of the C-terminus hinge regions of the two heavy chains. In a particularly preferred embodiment, the hinge region is modified to contain an odd number of sulfhydryl residues, preferably one, prior to conjugation.

Alternatively, both binding specificities can be encoded in the same vector and expressed and assembled in the same host cell. This method is particularly useful where the bispecific molecule is a mAb×mAb, mAb×Fab, Fab×F(ab')$_2$ or ligand× Fab fusion protein. A bispecific molecule can be a single chain molecule comprising one single chain antibody and a binding determinant, or a single chain bispecific molecule comprising two binding determinants. Bispecific molecules may comprise at least two single chain molecules. Methods for preparing bispecific molecules are described for example in U.S. Pat. No. 5,260,203; U.S. Pat. No. 5,455,030; U.S. Pat. No. 4,881,175; U.S. Pat. No. 5,132,405; U.S. Pat. No. 5,091,513; U.S. Pat. No. 5,476,786; U.S. Pat. No. 5,013,653; U.S. Pat. No. 5,258,498; and U.S. Pat. No. 5,482,858.

Binding of the bispecific molecules to their specific targets can be confirmed by, for example, enzyme-linked immunosorbent assay (ELISA), radioimmunoassay (RIA), FACS analysis, bioassay (e.g., growth inhibition), or Western Blot assay. Each of these assays generally detects the presence of protein-antibody complexes of particular interest by employing a labeled reagent (e.g., an antibody) specific for the complex of interest. For example, the FcR-antibody complexes can be detected using e.g., an enzyme-linked antibody or antibody fragment which recognizes and specifically binds to the antibody-FcR complexes. Alternatively, the complexes can be detected using any of a variety of other immunoassays. For example, the antibody can be radioactively labeled and used in a radioimmunoas say (RIA). The radioactive isotope can be detected by such means as the use of a γ-counter or a scintillation counter or by autoradiography.

(iii) Immunoconjugates

Immunoconjugates provided herein can be formed by conjugating the antibodies described herein to another therapeutic agent. Suitable agents include, for example, a cytotoxic agent (e.g., a chemotherapeutic agent), a toxin (e.g. an enzymatically active toxin of bacterial, fungal, plant or animal origin, or fragments thereof), and/or a radioactive isotope (i.e., a radioconjugate).

Chemotherapeutic agents useful in the generation of such immunoconjugates have been described above. Enzymatically active toxins and fragments thereof which can be used include diphtheria A chain, nonbinding active fragments of diphtheria toxin, exotoxin A chain (from *Pseudomonas aeruginosa*), ricin A chain, abrin A chain, modeccin A chain, alpha-sarcin, Aleurites fordii proteins, dianthin proteins, Phytolaca americana proteins (PAPI, PAPII, and PAP-S), momordica charantia inhibitor, curcin, crotin, sapaonaria officinalis inhibitor, gelonin, mitogellin, restrictocin, phenomycin, enomycin and the tricothecenes. A variety of radionuclides are available for the production of radioconjugated anti-EGFR antibodies. Examples include $^{212}Bi$, $^{131}I$, $^{131}In$, $^{90}Y$ and $^{186}Re$.

Immunoconjugates can be made using a variety of bifunctional protein coupling agents such as N-succinimidyl-3-(2-pyridyldithiol) propionate (SPDP), iminothiolane (IT), bifunctional derivatives of imidoesters (such as dimethyl adipimidate HCL), active esters (such as disuccinimidyl suberate), aldehydes (such as glutareldehyde), bis-azido compounds (such as bis (p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). Carbon-14-labeled 1-isothiocyanatobenzyl-3-methyldiethylene triaminepentaacetic acid (MX-DTPA) is an exemplary chelating agent for conjugation of radionucleotide to the antibody (see, e.g., WO94/11026).

III. Methods for Screening Antibodies

Subsequent to producing antibodies they can be screened for various properties, such as those described herein, using a variety of assays that are well known in the art.

In one embodiment, the antibodies are screened (e.g., by flow cytometry or ELISA) for binding to EGFR using, for example, purified EGFR and/or EGFR-expressing cells, such as A431 cells. The epitopes bound by the anti-EGFR antibodies can further be identified and compared, for example, to identify non-competing antibodies (e.g., antibodies that bind different epitopes), as well as antibodies which compete for binding and/or bind the same or overlapping epitopes.

Competitive antibodies (such as antibodies that compete for binding to ERGFR with any of the antibodies identified in Tables I and II, above) and non-competitive antibodies can be identified using routine techniques. Such techniques include, for example, an immunoassay, which shows the ability of one antibody to block (or not block) the binding of another antibody to a target antigen, i.e., a competitive binding assay. Competitive binding is determined in an assay in which the immunoglobulin under test inhibits specific binding of a reference antibody to a common antigen, such as EGFR. Numerous types of competitive binding assays are known, for example: solid phase direct or indirect radioimmunoassay (RIA), solid phase direct or indirect enzyme immunoassay (EIA), sandwich competition assay; solid phase direct biotin-avidin EIA; solid phase direct labeled assay, solid phase direct labeled sandwich assay; solid phase direct $^{125}I$ labeled RIA; solid phase direct biotin-avidin EIA; and direct labeled RIA. The surface plasmon resonance technique set forth in the Materials and Methods of the Examples and in Example 2, below, can also be used advantageously for this purpose. Typically, such an assay involves the use of purified antigen bound to a solid surface or cells bearing either of these, an unlabeled test immunoglobulin and a labeled reference immunoglobulin. Competitive inhibition is measured by determining the amount of label bound to the solid surface or cells in the presence of the test immunoglobulin. Usually the test immunoglobulin is present in excess. Usually, when a competing antibody is present in excess, it will inhibit specific binding of a reference antibody to a common antigen by at least 50-55%, 55-60%, 60-65%, 65-70% 70-75% or more.

Other screening techniques for determining the epitope bound by antibodies disclosed herein include, for example, x-ray analysis of crystals of antigen:antibody complexes, which provides atomic resolution of the epitope. Other methods monitor the binding of the antibody to antigen fragments or mutated variations of the antigen where loss of binding due to a modification of an amino acid residue within the antigen sequence is often considered an indication of an epitope component. In addition, computational combinatorial methods for epitope mapping can also be used. These methods rely on the ability of the antibody of interest to affinity isolate specific short peptides from combinatorial phage display peptide libraries. The peptides are then regarded as leads for the definition of the epitope corresponding to the antibody used to screen the peptide library. For epitope mapping, computational algorithms have also been developed which have been shown to map conformational discontinuous epitopes.

In another embodiment, the antibodies (e.g., non-competing antibodies anti-EGFR antibodies) are screened for the ability to bind to epitopes exposed upon binding to ligand, e.g., EGF (i.e., do not inhibit the binding of EGFR-binding ligands to EGFR). Such antibodies can be identified by, for example, contacting cells which express EGFR (e.g. A431 cells) with a labeled EGFR ligand (e.g., radiolabeled or biotinylated EGF) in the absence (control) or presence of the anti-EGFR antibody. If the antibody does not inhibit EGF binding to EGFR, then no statistically significantly decrease in the amount of label recovered, relative to the amount in the absence of the antibody, will be observed. Alternatively, if the antibody inhibits EGF binding to EGFR, then a statistically significantly decrease in the amount of label recovered, relative to the amount in the absence of the antibody, will be observed.

Antibodies also can be screened (tested) for their binding affinity. This can be done, for example, using a plasmon resonance assay, e.g., as described below.

Antibodies also can be screened for their ability to inhibit signaling through EGFR using signaling assays, such as, those described herein. For example, the ability of an antibody to inhibit EGFR ligand mediated phosphorylation of EGFRs can be assessed by treating cells expressing EGFR with an EGFR ligand (e.g., EGF) in the presence and absence of the antibody. The cells can then be lysed, crude lysates centrifuged to remove insoluble material, and EGFR phosphorylation measured, for example, by Western blotting followed by probing with an anti-phosphotyrosine antibody.

Alternatively, the ability of an antibody to inhibit downstream signaling through EGFR can be measured by kinase assays for known substrates of EGFR such as, for example, AKT and/or ERK, following EGFR stimulation by EGF ligand. For example, cells expressing EGFR can be stimulated with EGF ligand and incubated with a candidate antibody. Cell lysates subsequently prepared from such cells can be immunoprecipitated with an antibody for a substrate of EGFR (or a protein in a cellular pathway involving EGFR) such as, an anti-AKT antibody, and assayed for kinase activity (e.g., AKT kinase activity) using art-recognized techniques. A decrease in or complete disappearance in level or activity (e.g., kinase activity) of a EGFR substrate or protein in a pathway involving EGFR in the presence of the antibody, relative to the level or activity in the absence of the antibody is indicative of an antibody which inhibits EGFR signaling.

Antibodies that decrease levels of EGFR on cell surfaces can be identified by their ability to downregulate or inhibit EGFR expression on tumor cells. In certain embodiments, the antibodies decrease EGFR on cell surfaces by inducing internalization (or increasing endocytosis) of EGFR (e.g., by internalization and recycling of the receptor and/or internalization and degradation of the receptor). To test this, EGFR can be biotinylated and the number of EGFR molecules on the cell surface can be readily determined, for example, by measuring the amount of biotin on a monolayer of cells in culture in the presence or absence of an antibody, followed by immunoprecipitation of EGFR and probing with streptavidin. A decrease in detection of biotinylated EGFR over time in the presence of an antibody is indicative of an antibody that decreases EGFR levels on cell surfaces.

Antibodies can also be tested for their ability to inhibit growth of cells expressing EGFR (either in vivo or in vitro), such as tumor cells, using art recognized techniques, including the Cell Titer Glow Assay described in the Examples below and Tritium-labeled thymidine incorporation assay. Antibodies also can be screened for the ability to inhibit spheroid growth of cells expressing EGFR. This can be done by using an assay that approximates conditions of a developing tumor growth as described herein.

In another embodiment, combinations of anti-EGFR antibodies are screened for IC50 and/or IC90 values relative to inhibiting a particular EGFR activity or function, such as EGFR-mediated signaling (e.g., as measured by ELISA, Western, or multiplex methods, such as Luminex®. Combinations of antibodies, each of which possesses a particularly desired IC50 and/or IC90 value (e.g., an IC90 of about 80 nM for inhibiting EGFR signaling) can then be selected. In one embodiment, the combination has a greater IC50 or IC90 value than a known reference antibody (e.g., cetuximab). In another embodiment, the combination has an additive IC50 or IC90 (i.e., the sum of the activities of the antibodies, when acting individually on a cell expressing EGFR, is approximately equivalent to the combined effect of the same antibodies acting together on the same cell) In another embodiment, the combination has a synergistic IC50 or IC90 (i.e., the sum of the effects of the antibodies, when acting individually on a cell expressing EGFR, is less than the combined effect of the same antibodies acting together on the same cell).

IV. Pharmaceutical Compositions

In another aspect, herein provided is a composition, e.g., a pharmaceutical composition, containing one or a combination of monoclonal antibodies formulated together with a pharmaceutically acceptable carrier. In one embodiment, the compositions include a combination of multiple (e.g., two or more) isolated antibodies that bind different epitopes on EGFR. Such antibodies preferably have an additive or synergistic effect relative to inhibiting a particular EGFR activity or function, such as EGFR-mediated signaling.

As used herein, "pharmaceutically acceptable carrier" includes any and all solvents, dispersion media, coatings, antibacterial and antifungal agents, isotonic and absorption delaying agents, and the like that are physiologically compatible. Preferably, the carrier is suitable for intravenous, intramuscular, subcutaneous, parenteral, spinal or epidermal administration (e.g., by injection or infusion). Depending on the route of administration, the active compound, i.e., antibody, bispecific and multispecific molecule, may be coated in a material to protect the compound from the action of acids and other natural conditions that may inactivate the compound.

Compositions can be administered alone or in combination therapy, i.e., combined with other agents. For example, the combination therapy can include a composition provided herein with at least one or more additional therapeutic agents, such as the anti-cancer agents described herein. The compositions can also be administered in conjunction with radiation therapy and/or surgery. Particular combinations of anti-EGFR antibodies may also be administered separately or sequentially, with or without additional therapeutic agents.

Compositions can be administered by a variety of methods known in the art. As will be appreciated by the skilled artisan, the route and/or mode of administration will vary depending upon the desired results. The antibodies can be prepared with carriers that will protect the antibodies against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art.

To administer compositions by certain routes of administration, it may be necessary to coat the constituents, e.g., antibodies, with, or co-administer the compositions with, a material to prevent its inactivation. For example, the compositions may be administered to a subject in an appropriate carrier, for example, liposomes, or a diluent. Acceptable diluents include saline and aqueous buffer solutions. Liposomes include water-in-oil-in-water CGF emulsions as well as conventional liposomes.

Acceptable carriers include sterile aqueous solutions or dispersions and sterile powders for the extemporaneous preparation of sterile injectable solutions or dispersion. The use of such media and agents for pharmaceutically active substances is known in the art. Except insofar as any conventional medium or agent is incompatible with the antibodies, use thereof in compositions provided herein is contemplated. Supplementary active constituents can also be incorporated into the compositions.

Therapeutic compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, or sodium chloride in the composition.

Including in the composition an agent that delays absorption, for example, monostearate salts and gelatin can bring about prolonged absorption of the injectable compositions.

Sterile injectable solutions can be prepared by incorporating the monoclonal antibodies in the required amount in an appropriate solvent with one or a combination of ingredients enumerated above, as required, followed by sterilization microfiltration. Generally, dispersions are prepared by incorporating the antibodies into a sterile vehicle that contains a basic dispersion medium and the required other ingredients from those enumerated above. In the case of sterile powders for the preparation of sterile injectable solutions, the preferred methods of preparation are vacuum drying and freeze-drying (lyophilization) that yield a powder of the active ingredient plus any additional desired ingredient from a previously sterile-filtered solution thereof.

Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. For example, human antibodies may be administered once or twice weekly by subcutaneous injection or once or twice monthly by subcutaneous injection.

It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of antibodies calculated to produce the desired therapeutic effect in association with the required pharmaceutical carrier. The specification for the dosage unit forms provided herein are dictated by and directly dependent on (a) the unique characteristics of the antibodies and the particular therapeutic effect to be achieved, and (b) the limitations inherent in the art of compounding such antibodies for the treatment of sensitivity in individuals. Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

For the therapeutic compositions, formulations include those suitable for oral, nasal, topical (including buccal and sublingual), rectal, and parenteral administration. Parenteral administration is the most common route of administration for therapeutic compositions comprising antibodies. The formulations may conveniently be presented in unit dosage form and may be prepared by any methods known in the art of pharmacy. The amount of antibodies that can be combined with a carrier material to produce a single dosage form will vary depending upon the subject being treated, and the particular mode of administration. This amount of antibodies will generally be an amount sufficient to produce a therapeutic effect. Generally, out of one hundred percent, this amount will range from about 0.001 percent to about ninety percent of antibody by mass, preferably from about 0.005 percent to about 70 percent, most preferably from about 0.01 percent to about 30 per cent.

The phrases "parenteral administration" and "administered parenterally" as used herein means modes of administration other than enteral and topical administration, usually by injection, and includes, without limitation, intravenous, intramuscular, intraarterial, intrathecal, intraventricular, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion. Examples of suitable aqueous and nonaqueous carriers which may be employed in the pharmaceutical compositions provided herein include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Particular examples of adjuvants which are well-known in the art include, for example, inorganic adjuvants (such as aluminum salts, e.g., aluminum phosphate and aluminumhydroxide), organic adjuvants (e.g., squalene), oil-based adjuvants, virosomes (e.g., virosomes which contain a membrane-bound heagglutinin and neuraminidase derived from the influenza virus).

Prevention of presence of microorganisms may be ensured both by sterilization procedures and by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of one or more agents that delay absorption such as aluminum monostearate or gelatin.

When compositions are administered as pharmaceuticals, to humans and animals, they can be given alone or as a pharmaceutical composition containing, for example, 0.001 to 90% (more preferably, 0.005 to 70%, such as 0.01 to 30%) of active ingredient in combination with a pharmaceutically acceptable carrier.

Regardless of the route of administration selected, compositions provided herein, may be used in a suitable hydrated form, and they may be formulated into pharmaceutically acceptable dosage forms by conventional methods known to those of skill in the art.

Actual dosage levels of the antibodies in the pharmaceutical compositions provided herein may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts. A physician or veterinarian having ordinary skill in the art can readily determine and prescribe the effective amount of the composition required. For example, the physician or veterinarian could start doses of the antibodies at levels lower than that required to achieve the desired therapeutic effect and gradually increasing the dosage until the desired effect is achieved. In general, a suitable daily dose of compositions provided herein will be that amount of the antibodies which is the lowest dose effective to produce a therapeutic effect. Such an effective dose will generally depend upon the factors described above. It is preferred that administration be intravenous, intramuscular, intraperitoneal, or subcutaneous, preferably administered proximal to the site of the target. If desired, the effective daily dose of a therapeutic composition may be administered as two, three, four, five, six or more sub-doses administered separately at appropriate intervals throughout the day, optionally, in unit dosage forms. While it is possible for antibodies to be administered alone, it is preferable to administer antibodies as a formulation (composition).

Therapeutic compositions can be administered with medical devices known in the art, such as, for example, those disclosed in U.S. Pat. Nos. 5,399,163, 5,383,851, 5,312,335, 5,064,413, 4,941,880, 4,790,824, 4,596,556, 4,487,603, 4,486,194, 4,447,233, 4,447,224, 4,439,196, and 4,475,196.

In certain embodiments, the monoclonal antibodies can be formulated to ensure proper distribution in vivo. For example, the blood-brain barrier (BBB) excludes many highly hydrophilic compounds. To ensure that therapeutic antibodies cross the BBB (if desired), they can be formulated, for example, in liposomes. For methods of manufacturing liposomes, see, e.g., U.S. Pat. Nos. 4,522,811; 5,374,548; 5,399,331; 5,891,468; 6,056,973; 6,224,903; 6,316,024; 7,122,202; and 7,507,407. The liposomes may comprise one or more moieties that attach to and/or are selectively transported into specific cells or organs, thus enhance targeted drug delivery.

V. Methods of Using Antibodies

Also provided are methods of using antibodies that bind EGFR in a variety of ex vivo and in vivo diagnostic and therapeutic applications involving EGFR dependent signaling, including a variety of cancers.

Accordingly, in one embodiment, a method is provided for treating a disease associated with EGFR dependent signaling by administering to a subject an antibody or preferably a combination of antibodies provided herein in an amount effective to treat the disease. Suitable diseases include, for example, a variety of cancers including, but not limited to, melanoma, breast cancer, ovarian cancer, renal carcinoma, gastrointestinal cancer, colon cancer, lung cancer, pancreatic cancer, skin cancer, head and neck cancer glioblastoma, prostate cancer and other solid and/or metastatic tumors.

The antibody can be administered alone or with another therapeutic agent that acts in conjunction with or synergistically with the antibody to treat the disease associated with EGFR mediated signaling. Such therapeutic agents include those described herein, for example, small organic molecules, monoclonal antibodies, bispecific antibodies, recombinantly engineered biologics, RNAi compounds, tyrosine kinase inhibitors, and commercial antibodies, as well as anticancer agents (e.g., cytotoxins, chemotherapeutic agents, small molecules and radiation).

Also provided are kits comprising one or more anti-EGFR antibodies, optionally contained in a single vial, and include, e.g., instructions for use in treating or diagnosing a disease associated with EGFR upregulation and/or EGFR dependent signaling. The kits may include a label indicating the intended use of the contents of the kit. The term label includes any writing, marketing materials or recorded material supplied on or with the kit, or which otherwise accompanies the kit.

Other embodiments are described in the following non-limiting Examples.

EXAMPLES

Materials and Methods

Throughout the examples, the following materials and methods are used unless otherwise stated.

In general, unless otherwise indicated, conventional techniques of chemistry, molecular biology, recombinant DNA technology, immunology (especially, e.g., antibody technology), and standard techniques of polypeptide preparation are used.

Cell Lines

All the cell lines to be used in the experiments described below are obtained from the National Cancer Institute or ATCC.

Cell Lines:
A431—epidermoid carcinoma
OVCAR-3—ovarian cancer
Du 145—prostate carcinoma
ADRr—breast carcinoma
Pulverization of Tumor Cells A cryopulverizer (COVARIS Inc.) is used for the pulverization of tumors. Tumors are stored in special bags (pre-weighed before the addition of the tumor) and placed in liquid nitrogen while handling them. For small tumors, 200 µL of Lysis buffer is first added to the bag containing the tumor, frozen in liquid nitrogen and then pulverized to improve the recovery of the tumor from the bag. Pulverized tumors are transferred to 2 mL EPPENDORF tubes and placed in liquid nitrogen until ready for further processing.

Lysis of Tumor Cells

Tumors are lysed in Lysis buffer supplemented with protease and phosphatase inhibitors. Lysis Buffer is added to the tumor aliquots in a final concentration of about 62.5 mg/mL. Tumor samples are homogenized by vortexing for 30 sec and incubating on ice for about 30 min. The lysates are spun for about 10 min in Qiagen Qiashredder columns for further homogenization of the samples. Cleared lysates are aliquoted into fresh tubes for further processing.

BCA Assay

BCA assay (Pierce) is performed following the manufacturer's protocol on all tumor samples. The total protein concentration (in mg/mL) of each tumor sample is later used in the normalization of the ELISA results.

ELISA Assay

All ELISA reagents for the total and phospho-EGFR ELISAs are purchased from R&D Systems as Duoset kits. 96-half well GREINER high binding plates (Cat. #675077; GREINER BIO-ONE, Monroe, N.C.) are coated with 50 uL of an antibody and incubated overnight at room temperature. Next morning, plates are washed 3 times with 1000 µl/well in a BIOTEK plate washer with PBST (0.05% Tween-20). Plates are subsequently blocked for about 1 hour at room temperature with 2% BSA in PBS. The plates are washed 3 times with 1000 µl/well in the BIOTEK plate washer with PBST (0.05% Tween-20). 50 µL of cell lysates and standards diluted in 50% Lysis buffer and 1% BSA are used in duplicates for further processing. Samples are incubated for 2 hrs at 4° C. with shaking and washed 3 times with 1000 µl/well in the BIOTEK plate washer with PBST (PBS with 0.05% Tween-20). About 50 µl of a detection antibody diluted in 2% BSA, PBST is added and incubated for about 1 hour at room temperature. For phospho-EGFR, the detection antibody is directly conjugated to horse radish peroxidase (HRP) and incubated for 2 hrs at room temperature. The plate is washed 3 times with 1000 µl/well in the BIOTEK plate washer with PBST (0.05% Tween-20). About 50 µl of Streptavidin-HRP is added and incubate for 30 min at room temperature (except for pErbB3). The plates are washed 3 times with 1000 µl/well in the BIOTEK plate washer with PBST (0.05% Tween-20). About 50 µL of SUPERSIGNAL PICO ELISA substrate is added and the plate is read using a Fusion plate reader. The data is analysed using EXCEL. Duplicate samples are averaged and the error bars are used to represent the standard deviation between the two replicates.

Inhibition of AKT and/or ERK Signaling

EGFR mediated signaling via AKT or ERK is measured using art recognized techniques using kinase assays for such proteins. See, for example, US patent publication No. 2010-0056761.

EGFR Dimerization Assay

To measure the extent of EGFR homodimerization in cells, co-precipitation assays using two kinds of epitope-tagged EGFR constructs are used, e.g., EGFR-flag and EGFR-myc which contain Flag and Myc tags, respectively, in the C-terminal region of EGFR. EGFR-flag and EGFR-myc are co-transfected into cells, e.g., COS-7 cells and incubated in serum-free media. The cell lysates are precipitated with anti-Flag antibody and the precipitated material is analyzed by Western blotting using the anti-Myc antibody, or vice versa. The amount of co-precipitation of EGFR-myc with the anti-Flag antibody, and EGFR-flag co-precipitated with anti-Myc antibody in the presence and absence (control) of antibody is measured and compared.

EGFR Internalization Assay

To measure the extent of EGFR internalization (i.e., decrease in EGFR expression), cells expressing radiolabeled EGFR (e.g., $^{125}$I) are incubated in the presence and absence (control) of antibody. The ratio of internalized and surface radioactivity is determined and compared.

Binding Affinity

Dissociation constants of anti-EGFR antibodies may be measured using two independent techniques, e.g., a Surface Plasmon Resonance Assay and a cell binding assay using A431 cells. Affinities and cross reactivity of antibodies are also measured in solution with recombinant EGF receptor using KinExA instrumentation (SAPIDYNE Instruments, Boise, Id.). The procedure used 12 three-fold titrated dilutions of ErbB1.6his (1000 nM, 333 nM, 111 nM, 37 nM, 12.3 nM, 4.1 nM, 1.37 nM, 450 pM, 150 pM, 50 pM, 17 pM) prepared in 5 mL tubes keeping the concentration of antibodies in each tube constant at 250 pM. 15 mL of 2 ug/mL Cy5 labeled Ga human IgG secondary antibody is prepared via a 1:1000 dilution of stock solution (2 mg/mL). ErbB1.6HIS conjugated PMMA beads are coupled according to SAPIDYNE's KinExA protocol. 100 ug of ErbB1-6his is added to a pre-measured aliquot of 200 mg PMMA beads. 1×PBS is then added to the solution to make the final volume 1 ml. This solution is then incubated at room temp for 1 hr. The beads are then transferred to a bead vial with 27 ml 1×PBS. The experiment is then setup by entering the parameters in the KinExA Pro software.

Surface Plasmon Resonance Assay

The Surface Plasmon Resonance Assay is performed as follows.

Either antibody or antigen (300 RU) is immobilized on a CM5 chip using amine coupling. Different concentrations of antibodies or antigens are then injected to study their association and dissociation with the immobilized protein. Between different injections, the chip is regenerated using suitable regeneration buffer (such as glycine, pH 2.5). The dissociation phase is fitted using Equation 1 to determine $K_{off}$ (dissociate rate):

$$R = R_o * \exp(-K_{off} * t) \quad (1)$$

The association phase is fitted using this value of $K_{off}$ and Equation 2 to determine determine $K_{on}$ (association rate) and $K_D$ (equlibrium constant).

$$R = \frac{R_{max} * C}{K_D + C}(1 - \exp(-(K_{on} * C + K_{off})t)) \quad (2)$$

where C represents either the antigen or antibody concentration in solution, $R_{max}$ represents the saturation signal and t represents the time.

Cell Binding Assay

Cell binding assays for determining the $K_D$ values are performed as follows: A431 cells are detached with 3 mLs trypsin-EDTA at 37° C. for 5 minutes. Complete DMEM (10 mLs) is added immediately to the trypsinized cells, resuspended gently and spun down in a Beckman tabletop centrifuge at 1100 rpm for 5 minutes. Cells are resuspended in stain buffer (PBS+0.2% BSA+0.1% sodium azide) at a concentration of $2 \times 10^6$ cells per ml and 50 µl ($1 \times 10^5$ cells) aliquots are plated in a 96-well titer plate.

A 300 µl stock solution of 2000 nM anti-EGFR antibody is prepared in stain buffer and 100 ul of it is serially diluted into 200 ul of stain buffer. The concentrations of the diluted antibody range from 2000 nM to 0.1 nM. 150 µl aliquots of the different protein dilutions are then added directly to the 50 ul cell suspension giving final concentrations of 1500 nM, 500 nM, 166.7 nM, 55.6 nM, 18.5 nM, 6.17 nM, 2.05 nM, 0.68 nM, 0.23 nM and 0.076 nM of the antibody.

Aliquoted cells in the 96-well plate are incubated with the protein dilutions for 2 hr at room temperature with shaking and washed 3 times with 300 µl stain buffer. Cells are then incubated with 100 µl of a 1:750 dilution of Alexa 647-labeled goat anti-human IgG in BD stain buffer for 45 minutes with shaking at 4° C. Finally, cells are washed twice, pelleted and resuspended in 250 µl stain buffer+0.5 µg/ml propidium iodide. Analysis of 10,000 cells is done in a FACSCALIBUR flow cytometer using the FL4 channel. MFI values and the corresponding concentrations of the anti-EGFR-antibodies are plotted on the y-axis and x-axis, respectively. The $K_D$ of the molecule is determined using GRAPHPAD PRISM software using the one-site binding model for a non-linear regression curve.

The $K_D$ value is calculated based on the formula Y=Bmax*X/$K_D$+x(Bmax=fluorescence at saturation. X=antibody concentration. Y=degree of binding).

Inhibition of Tumor Cell Proliferation

Inhibition of cellular proliferation of cells expressing EGFR (e.g., cancer cells) is examined as follows: Du145, A431 or OVCAR-3 cells are seeded in 96 well tissue culture plates at 20,000 cells per well and grown in RPMI-1640 medium supplemented with antibiotics, 2 mM L-glutamine and 10% fetal bovine serum (FBS) for 24 hours at 37 degrees Celsius and 5% carbon dioxide. Medium is then switched to RPMI-1640 (with antibiotics, 2 mM L-glutamine, 0.5% FBS) which is without or with antibody at 200 nM, 20 nM, 2 nM, 0.2 nM, 0.02 nM and 0 nM concentrations (a control IgG is used as an isotype control). Cells are grown for 36 hours at 37° C. and 5% carbon dioxide. The cells then are pulsed with 25 µl of a 1:40 dilution of $^3$H-Thymidine (20 Ci/mmol, 1 mCi/ml), incubated over night (18 hrs), harvested to FILTER-MATS and read on a beta counter Inhibition of EGFR Phosphorylation in Tumor Cells To assess inhibition of EGFR phosphorylation in vivo, samples are lysed and BCA and ELISA assays are performed as described above.

Inhibition of EGF Induced EGFR Phosphorylation

Inhibition of EGF induced EGFR phosphorylation is examined as follows: OVCAR-3 and ADRr cells are plated at a density of 35,000 cells/well in a 96 well plate. Cells are incubated in 10% serum for 24 hrs and then serum starved for 14 hrs. Cells are then preincubated with different concentrations of anti-EGFR antibodies for 40 minutes. Following pre incubation, the medium is removed and the cells are stimulated for 5 minutes at 37° C., 5% $CO_2$ with 50 nM human EGF. EGF controls (5 minutes, 5 nM), 10% serum and 0% serum controls are also used. Cells are washed with 1× cold PBS and lysed in 50 µl ice cold lysis buffer (R & D SYSTEMS ELISA Kit Buffer 12 with freshly added protease inhibitors) by incubating on ice for 30 minutes. Lysates are either analyzed immediately or frozen at −80° C. until use.

Inhibition of EGF-Mediated Signaling in Tumor Cells

Inhibition of ligand-mediated tumor cell signaling is investigated as follows: OVCAR-3 or Du145 cells are seeded in 96 well tissue culture plates and grown in RPMI-1640 medium supplemented with antibiotics, 2 mM L-glutamine and 10% fetal bovine serum (FBS) for 24 hours at 37° C. and 5% carbon dioxide. Cells are serum starved in RPMI-1640 medium with antibiotics and 2 mM L-glutamine for 24 hours at 37° C. and 5% carbon dioxide. Cells are pre-treated with and without the anti-EGFR antibody at 1 µM, 250 nM, 63 nM, 16 nM, 4.0 nM, 1.0 nM, 240 pM and 61 pM concentrations for 30 minutes then stimulated with EGF ligand for 10 minutes at 37° C. and 5% carbon dioxide. Cells are washed with cold PBS then harvested with mammalian protein extract (MPER) lysis buffer (Pierce, 78505) containing 150 mM NaCl 5 mM sodium pyrophosphate, 10 mM bpV (phen), 50 mM phenalarsine, 1 mM sodium orthovanadate, and protease inhibitor cocktail (Sigma, P714). Cell lysates are diluted two-fold with 4% bovine serum albumin in phosphate buffered saline with 0.1% Tween-20, then analyzed by ELISA for AKT (a downstream effector of EGFR) and EGFR phosphorylation.

To test for AKT phosphorylation, lysates are run on an ELISA plate with a capture antibody specific for AKT and biotinylated detection antibody specific to the phosphorylation site on serine 473 of AKT. Signal is generated with streptavidin conjugated to horseradish-peroxidase reacted with chemiluminescent substrate (Pierce, 37070).

Example 1

Production of Antibodies

In order to obtain human anti-EGFR antibodies, expression libraries are screened in accordance with methods disclosed in US Patent Publications 20100056386 and 20090181855.

Example 2

Binding Affinity/Epitope Binning

Surface Plasmon Resonance (SPR) is used to analyze binding affinity. Specifically, one of the proteins (antibody or target) is immobilized on the surface of the chip (as described herein) and the other protein is added. The association/dissociation interaction of the two proteins is measured. As the protein in solution associates with the immobilized protein, an increase in refractive index results which is captured by the resonance signal. As the protein dissociates, a decrease in signal results.

Epitope binning (EGF blocking) is analyzed using BIACORE analysis as described above. One of the antibodies is immobilized on the surface of the chip. As EGFR associates with the antibody, the resonance signal increases. The chip is then regenerated and a mixture of EGFR and another antibody (e.g., an antibody previously determined to bind to EGFR) is injected. If the antibody binds overlapping epitopes with the injected antibody, then the signal will be less compared to EGFR injected alone. The chip is then regenerated again and a mixture of EGF ligand and EGFR is injected. Resonance signal is measured. A decrease in signal indicates overlapping epitopes with EGF ligand. The chip is regenerated for a final time and injected with EGFR to confirm the activity of the antibody.

Example 3

Inhibition of EGFR Phosphorylation in Tumor Cells

Inhibition of EGFR phosphorylation in ADRr, Ovcar3, and A431 cells by particular anti-EGFR antibodies is analyzed as described above.

Example 4

Inhibition of AKT Phosphorylation in Tumor Cells

Inhibition of AKT phosphorylation in Du145 and Ovcar3 cells for antibody combinations is analyzed as described above. Two cell lines are tested based on two parameters: (1) high ($>10^5$ receptors/cell) expression of ErbB1 and (2) dynamic range of induction of pAKT is ≥5-fold.

All anti-EGFR antibodies are combined with another anti-EGFR antibody without regard to epitope mapping. Six point inhibition curves are created (2 µM peak concentration with serial 10× dilutions for many pairs and trios, while some are screened with 4 point dilution curves.

All antibodies that either additively or synergistically inhibit pAKT will map to distinct epitopes. Some pairs will be more potent inhibitors than cetuximab. Results in two cell lines minor each other suggesting that, in the absence of mutated receptors or signaling pathways (e.g., kRAS), high expression of ErbB1 (and perhaps ErbB1>ErbB2/3) is a beginning criteria for synergy.

Short and long-term inhibition studies are conducted using anti-EGFR antibody combinations with 40 minute pre-incubation of antibodies. Assays are repeated with 40 minute, compared to 24 hours, pre-incubation of antibodies. Data show that effects of internalization and degradation of EGFR change readouts.

Example 5

Inhibition of Tumor Cell Proliferation

Inhibition of tumor cell proliferation is analyzed as described above. The inhibitory action of the pairs and trios provided herein on DU145 cells is preferably robust. Also, preferred pairs and trios of antibodies present a greater inhibition of Du145 cell proliferation than an equimolar concentration of cetuximab. Pairs and trios are evaluated in pERK assay as well. Preferred pairs and trios are a potent antagonists of pERK signaling.

EQUIVALENTS

Those skilled in the art will recognize, or be able to ascertain using no more than routine experimentation, many equivalents of the specific embodiments described herein. Such equivalents are intended to be encompassed by the following claims. Any combination of the embodiments disclosed in the any plurality of the dependent claims are contemplated to be within the scope of the disclosure.

INCORPORATION BY REFERENCE

All, patents, pending patent applications and patent publications referred to hereinabove are hereby incorporated by reference in their entireties.

```
(Human EGFR)
                                                          SEQ ID NO: 57
            10         20         30         40         50         60
     MRPSGTAGAA LLALLAALCP ASRALEEKKV CQGTSNKLTQ LGTFEDHFLS LQRMFNNCEV 70         80         90        100        110        120
     VLGNLEITYV QRNYDLSFLK TIQEVAGYVL IALNTVERIP LENLQIIRGN MYYENSYALA 130        140        150        160        170        180
     VLSNYDANKT GLKELPMRNL QEILHGAVRF SNNPALCNVE SIQWRDIVSS DFLSNMSMDF 190        200        210        220        230        240
     QNHLGSCQKC DPSCPNGSCW GAGEENCQKL TKIICAQQCS GRCRGKSPSD CCHNQCAAGC 250        260        270        280        290        300
     TGPRESDCLV CRKFRDEATC KDTCPPLMLY NPTTYQMDVN PEGKYSFGAT CVKKCPRNYV 310        320        330        340        350        360
     VTDHGSCVRA CGADSYEMEE DGVRKCKKCE GPCRKVCNGI GIGEFKDSLS INATNIKHFK 370        380        390        400        410        420
     NCTSISGDLH ILPVAFRGDS FTHTPPLDPQ ELDILKTVKE ITGFLLIQAW PENRTDLHAF 430        440        450        460        470        480
     ENLEIIRGRT KQHGQFSLAV VSLNITSLGL RSLKEISDGD VIISGNKNLC YANTINWKKL 490        500        510        520        530        540
     FGTSGQKTKI ISNRGENSCK ATGQVCHALC SPEGCWGPEP RDCVSCRNVS RGRECVDKCN 550        560        570        580        590        600
     LLEGEPREFV ENSECIQCHP ECLPQAMNIT CTGRGPDNCI QCAHYIDGPH CVKTCPAGVM 610        620        630        640        650        660
     GENNTLVWKY ADAGHVCHLC HPNCTYGCTG PGLEGCPTNG PKIPSIATGM VGALLLLLVV 670        680        690        700        710        720
     ALGIGLFMRR RHIVRKRTLR RLLQERELVE PLTPSGEAPN QALLRILKET EFKKIKVLGS 730        740        750        760        770        780
     GAFGTVYKGL WIPEGEKVKI PVAIKELREA TSPKANKEIL DEAYVMASVD NPHVCRLLGI 790        800        810        820        830        840
     CLTSTVQLIT QLMPFGCLLD YVREHKDNIG SQYLLNWCVQ IAKGMNYLED RRLVHRDLAA 850        860        870        880        890        900
     RNVLVKTPQH VKITDFGLAK LLFAEEKEYH AEFFKCPIKW MALESILHRI YTHQSDVWSY 910        920        930        940        950        960
     GVTVWELMTF GSKPYDGIPA SEISSILEKG ERLPQPPICT IDVYMIMVKC WMIDADSRPK 970        980        990       1000       1010       1020
     FRELIIEFSK MARDPQRYLV IQGDERMHLP SPTDSNFYRA LMDEEDMDDV VDADEYLIPQ 1030       1040       1050       1060       1070       1080
     QGFFSSPSTS RTPLLSSLSA TSNNSTVACI DRNGLQSCPI KEDSFLQRYS SDPTGALTED 1090       1000       1110       1120       1130       1140
     SIDDTFLPVP EYINQSVPKR PAGSVQNPVY HNQPLNPAPS RDPHYQDPHS TAVGNPELYN 1150       1160       1170       1180       1190       1200
     TVQPTCVNST FDSPAHWAQK GSHQISLDNP DYQQDFFPKE AKPNGIFKGS TAENAEYLRV

1210
     APQSSEFIGA
```

What is claimed is:

1. A composition comprising a trio of anti-EGFR antibodies comprising a first monoclonal antibody, a second monoclonal antibody and a third monoclonal antibody, wherein (i) the first antibody is or binds to the same epitope as, antibody ca (comprising heavy chain CDRs 1, 2 and 3 set forth in SEQ ID NOs: 29, 30 and 34, respectively, and light chain CDRs 1, 2 and 3 set forth in SEQ ID NOs: 48, 45 and 49, respectively); (ii) the second antibody is or binds to the same epitope as, antibody cd (comprising heavy chain CDRs 1, 2 and 3 set forth in SEQ ID NOs: 29, 30 and 31, respectively, and light chain CDRs 1, 2 and 3 set forth in SEQ ID NOs: 53, 54 and 55, respectively); and (iii) the third antibody is or binds to the same epitope as, antibody ch (comprising heavy chain CDRs 1, 2 and 3 set forth in SEQ ID NOs: 23, 24 and 26, respectively, and light chain CDRs 1, 2 and 3 set forth in SEQ ID NOs: 39, 40 and 42, respectively).

2. A composition comprising a trio of antibodies of claim 1 wherein each antibody of the trio is an IgG1, IgG2, IgG3, IgG4, IgM, IgA1, IgA2, IgAsec, IgD, or IgE.

3. The composition of claim 1, wherein each of the antibodies comprised by the composition binds to EGFR with a $K_D$ of $10^7$ to $10^{12}$ $M^{-1}$.

4. The composition of claim 1, wherein the composition exhibits at least one of the following properties:
   (a) inhibition of AKT phosphorylation or ERK phosphorylation, as measured in a cell-based in vitro assay;
   (b) inhibition of the growth of tumor cells expressing EGFR in vitro;
   (c) inhibition of the growth of tumor cells expressing EGFR in a xenograft model in vivo;
   (d) inhibition of ligand binding to EGFR extracellular domain in vitro;
   (e) inhibition of EGFR dimerization in vitro; or
   (f) downregulation of EGFR on cell surfaces in vitro.

5. The composition of claim 4, wherein the inhibition or downregulation is additive or synergistic as compared to a preparation comprising an individual antibody comprised by the composition in an amount (in moles) equivalent to the total amount (in moles) of combined antibodies in the composition.

6. A kit comprising the composition of claim in a container.

7. A monoclonal antibody of claim 1, wherein the antibody is selected from the group consisting of a bispecific antibody, immunoconjugate, Fab, Fab'2, and ScFv.

8. A method of using the composition of claim 1 for the treatment of a human subject having a cancer associated with EGFR dependent signaling, the method comprising administering the composition to the subject in an amount sufficient to produce a therapeutic effect.

9. The method of claim 8, wherein the treatment of the cancer is treatment by combination therapy with an additional anti-cancer agent.

10. The method of claim 9 wherein the additional anti-cancer agent comprises a topoisomerase inhibitor.

11. A method of using a composition of claim 2 for the treatment of a human subject having a cancer associated with EGFR dependent signaling, the method comprising administering the composition to the subject as combination therapy with an additional anti-cancer agent.

12. The method of claim 11, wherein the additional anti-cancer agent comprises a topoisomerase inhibitor.

\* \* \* \* \*

UNITED STATES PATENT AND TRADEMARK OFFICE
CERTIFICATE OF CORRECTION

| | |
|---|---|
| PATENT NO. | : 9,044,460 B2 |
| APPLICATION NO. | : 13/100920 |
| DATED | : June 2, 2015 |
| INVENTOR(S) | : Raghida Bukhalid et al. |

It is certified that error appears in the above-identified patent and that said Letters Patent is hereby corrected as shown below:

In the claims

At column 89, claim number 3, line number 8, delete "$K_D$ of $10^7$ to $10^{12}$ $M^{-1}$" and insert -- $K_D$ of $10^{-7}$ to $10^{-12}$ M --

At column 90, claim number 6, line number 4, delete "A kit comprising the composition of claim in a container" and insert -- A kit comprising the composition of claim 1 in a container --

Signed and Sealed this
Seventh Day of June, 2016

Michelle K. Lee
*Director of the United States Patent and Trademark Office*

SEQUENCE LISTING

<160> NUMBER OF SEQ ID NOS: 70

<210> SEQ ID NO 1
<211> LENGTH: 142
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Met Gly Phe Gly Leu Ser Trp Leu Phe Leu Val Ala Ile Leu Lys Gly
1               5                   10                  15

Val Gln Cys Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Thr Ser Tyr Gly Ile Asn Trp Val Arg Gln Ala Pro Gly Gln Gly Leu
    50                  55                  60

Glu Trp Met Gly Trp Ile Ser Ala Tyr Asn Gly Asn Thr Asn Tyr Ala
65                  70                  75                  80

Gln Lys Leu Gln Gly Arg Val Thr Met Thr Thr Asp Thr Ser Thr Ser
                85                  90                  95

Thr Ala Tyr Met Glu Leu Arg Ser Leu Arg Ser Asp Asp Thr Ala Val
            100                 105                 110

Tyr Tyr Cys Ala Arg Asp Ser Gly Gly Tyr Gly Ser Gly Ser Val Pro
        115                 120                 125

Phe Asp Pro Trp Gly Gln Gly Thr Leu Val Thr Val Ser Ser
    130                 135                 140

<210> SEQ ID NO 2
<211> LENGTH: 142
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Met Gly Phe Gly Leu Ser Trp Leu Phe Leu Val Ala Ile Leu Lys Gly
1               5                   10                  15

Val Gln Cys Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Thr Ser Tyr Gly Ile Asn Trp Val Arg Gln Ala Pro Gly Gln Gly Leu
    50                  55                  60

Glu Trp Met Gly Trp Ile Ser Ala Tyr Asn Gly Asn Thr Asn Tyr Ala
65                  70                  75                  80

Gln Lys Leu Gln Gly Arg Val Thr Met Thr Thr Asp Thr Ser Thr Ser
                85                  90                  95

Thr Ala Tyr Met Glu Leu Arg Ser Leu Arg Ser Asp Asp Thr Ala Val
            100                 105                 110

Tyr Tyr Cys Ala Arg Asp Leu Gly Gly Tyr Gly Ser Gly Ser Val Pro
        115                 120                 125

Phe Asp Pro Trp Gly Gln Gly Thr Leu Val Thr Val Ser Ser
    130                 135                 140

```
<210> SEQ ID NO 3
<211> LENGTH: 142
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Met Gly Phe Gly Leu Ser Trp Leu Phe Leu Val Ala Ile Leu Lys Gly
1               5                   10                  15

Val Gln Cys Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Thr Ser Tyr Gly Ile Asn Trp Val Arg Gln Ala Pro Gly Gln Gly Leu
    50                  55                  60

Glu Trp Met Gly Trp Ile Ser Ala Tyr Asn Gly Asn Thr Asn Tyr Ala
65                  70                  75                  80

Gln Lys Leu Gln Gly Arg Val Thr Met Thr Thr Asp Thr Ser Thr Ser
                85                  90                  95

Thr Ala Tyr Met Glu Leu Arg Ser Leu Arg Ser Asp Asp Thr Ala Val
            100                 105                 110

Tyr Tyr Cys Ala Arg Asp Gly Gly Pro Tyr Gly Phe Gly Pro Pro Trp
        115                 120                 125

Phe Asp Pro Trp Gly Gln Gly Thr Leu Val Thr Val Ser Ser
    130                 135                 140

<210> SEQ ID NO 4
<211> LENGTH: 143
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Met Gly Phe Gly Leu Ser Trp Leu Phe Leu Val Ala Ile Leu Lys Gly
1               5                   10                  15

Val Gln Cys Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Thr Ser Tyr Gly Ile Ser Trp Val Arg Gln Ala Pro Gly Gln Gly Leu
    50                  55                  60

Glu Trp Met Gly Trp Ile Ser Ala Tyr Asn Gly Asn Thr Asp Tyr Ala
65                  70                  75                  80

Gln Lys Leu Gln Gly Arg Val Thr Met Thr Thr Asp Thr Ser Thr Ser
                85                  90                  95

Thr Ala Tyr Met Glu Leu Arg Ser Leu Arg Ser Asp Asp Thr Ala Val
            100                 105                 110

Tyr Tyr Cys Ala Arg Asp Leu Gly Gly Tyr Gly Ser Gly Gly Val Gly
        115                 120                 125

Tyr Phe Asp Pro Trp Gly Arg Gly Thr Ser Val Thr Val Ser Ser
    130                 135                 140

<210> SEQ ID NO 5
<211> LENGTH: 143
<212> TYPE: PRT
```

<213> ORGANISM: Artificial Sequence
<220> FEATURE:
<223> OTHER INFORMATION: Description of Artificial Sequence: Synthetic
      polypeptide

<400> SEQUENCE: 5

```
Met Gly Phe Gly Leu Ser Trp Leu Phe Leu Val Ala Ile Leu Lys Gly
1               5                   10                  15

Val Gln Cys Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Thr Ser Tyr Gly Ile Ser Trp Val Arg Gln Ala Pro Gly Gln Gly Leu
    50                  55                  60

Glu Trp Met Gly Trp Ile Ser Ala Tyr Asn Gly Asn Thr Asn Tyr Ala
65                  70                  75                  80

Gln Lys Leu Gln Gly Arg Val Thr Met Thr Thr Asp Thr Ser Thr Ser
                85                  90                  95

Thr Ala Tyr Met Glu Leu Arg Ser Leu Arg Ser Asp Asp Thr Ala Val
            100                 105                 110

Tyr Tyr Cys Ala Arg Asp Leu Gly Gly Tyr Gly Ser Gly Val Gly
        115                 120                 125

Tyr Phe Asp Pro Trp Gly Arg Gly Thr Leu Val Thr Val Ser Ser
    130                 135                 140
```

<210> SEQ ID NO 6
<211> LENGTH: 138
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

```
Met Gly Phe Gly Leu Ser Trp Leu Phe Leu Val Ala Ile Leu Lys Gly
1               5                   10                  15

Val Gln Cys Gln Val Gln Leu Val Gln Ser Gly Ala Glu Val Lys Lys
            20                  25                  30

Pro Gly Ser Ser Val Lys Val Ser Cys Lys Ala Ser Gly Gly Thr Phe
        35                  40                  45

Gly Ser Tyr Ala Ile Ser Trp Val Arg Gln Ala Pro Gly Gln Gly Leu
    50                  55                  60

Glu Trp Met Gly Ser Ile Ile Pro Ile Phe Gly Thr Ala Asn Tyr Ala
65                  70                  75                  80

Gln Lys Phe Gln Gly Arg Val Thr Ile Thr Ala Asp Glu Ser Thr Ser
                85                  90                  95

Thr Ala Tyr Met Glu Leu Ser Ser Leu Arg Ser Glu Asp Thr Ala Val
            100                 105                 110

Tyr Tyr Cys Ala Arg Met Gly Arg Gly Lys Val Ala Phe Asp Ile Trp
        115                 120                 125

Gly Gln Gly Thr Met Val Thr Ala Ser Ser
    130                 135
```

<210> SEQ ID NO 7
<211> LENGTH: 138
<212> TYPE: PRT
<213> ORGANISM: Artificial Sequence
<220> FEATURE:
<223> OTHER INFORMATION: Description of Artificial Sequence: Synthetic -continued

```
      polypeptide

<400> SEQUENCE: 7

Met Gly Phe Gly Leu Ser Trp Leu Phe Leu Val Ala Ile Leu Lys Gly
1               5                   10                  15

Val Gln Cys Gln Val Gln Leu Val Gln Ser Gly Ala Glu Val Lys Lys
            20                  25                  30

Pro Gly Ser Ser Val Lys Val Ser Cys Lys Ala Ser Gly Gly Thr Phe
        35                  40                  45

Gly Ser Tyr Ala Ile Ser Trp Val Arg Gln Ala Pro Gly Gln Gly Leu
    50                  55                  60

Glu Trp Met Gly Ser Ile Ile Pro Ile Phe Gly Thr Ala Asn Tyr Ala
65                  70                  75                  80

Gln Lys Phe Gln Gly Arg Val Thr Ile Thr Ala Asp Glu Ser Thr Ser
                85                  90                  95

Thr Ala Tyr Met Glu Leu Ser Ser Leu Arg Ser Glu Asp Thr Ala Val
            100                 105                 110

Tyr Tyr Cys Ala Arg Met Ala Arg Gly Lys Val Ala Phe Asp Ile Trp
        115                 120                 125

Gly Gln Gly Thr Met Val Thr Val Ser Ser
    130                 135

<210> SEQ ID NO 8
<211> LENGTH: 138
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Met Gly Phe Gly Leu Ser Trp Leu Phe Leu Val Ala Ile Leu Lys Gly
1               5                   10                  15

Val Gln Cys Gln Val Gln Leu Val Gln Ser Gly Ala Glu Val Lys Lys
            20                  25                  30

Pro Gly Ser Ser Val Lys Val Ser Cys Lys Ala Ser Gly Gly Thr Phe
        35                  40                  45

Ser Ser Tyr Ala Ile Ser Trp Val Arg Gln Ala Pro Gly Gln Gly Leu
    50                  55                  60

Glu Trp Met Gly Ser Ile Ile Pro Ile Phe Gly Thr Ala Asn Tyr Ala
65                  70                  75                  80

Gln Lys Phe Gln Gly Arg Val Thr Ile Thr Ala Asp Glu Ser Thr Ser
                85                  90                  95

Thr Ala Tyr Met Glu Leu Ser Ser Leu Arg Ser Glu Asp Thr Ala Val
            100                 105                 110

Tyr Tyr Cys Ala Arg Met Val Arg Gly Lys Val Ala Phe Asp Ile Trp
        115                 120                 125

Gly Gln Gly Thr Met Val Thr Val Ser Ser
    130                 135

<210> SEQ ID NO 9
<211> LENGTH: 140
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9
```

Met Gly Phe Gly Leu Ser Trp Leu Phe Leu Val Ala Ile Leu Lys Gly
1               5                   10                  15

Val Gln Cys Gln Val Gln Leu Val Gln Ser Gly Ala Glu Val Lys Lys
            20                  25                  30

Pro Gly Ser Ser Val Lys Val Ser Cys Lys Ala Ser Gly Gly Thr Phe
        35                  40                  45

Ser Ser Tyr Ala Ile Ser Trp Val Arg Gln Ala Pro Gly Gln Gly Leu
    50                  55                  60

Glu Trp Met Gly Ser Ile Ile Pro Ile Phe Gly Thr Ala Asn Tyr Ala
65              70                  75                  80

Gln Lys Phe Gln Gly Arg Val Thr Ile Thr Ala Asp Glu Ser Thr Ser
                85                  90                  95

Thr Ala Tyr Met Glu Leu Ser Ser Leu Arg Ser Glu Asp Thr Ala Val
            100                 105                 110

Tyr Tyr Cys Ala Arg Asp Pro Ser Val Asp Leu Tyr Trp Tyr Phe Asp
        115                 120                 125

Leu Trp Gly Arg Gly Thr Leu Val Thr Val Ser Ser
    130                 135                 140

<210> SEQ ID NO 10
<211> LENGTH: 138
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Met Gly Phe Gly Leu Ser Trp Leu Phe Leu Val Ala Ile Leu Lys Gly
1               5                   10                  15

Val Gln Cys Gln Val Gln Leu Gln Glu Ser Gly Pro Gly Leu Val Lys
            20                  25                  30

Pro Ser Glu Thr Leu Ser Leu Thr Cys Thr Val Ser Gly Gly Ser Val
        35                  40                  45

Asn Ser Gly Ser Tyr Tyr Trp Ser Trp Val Arg Gln Pro Pro Gly Lys
    50                  55                  60

Gly Leu Trp Ile Gly Ser Ile Tyr Tyr Ser Gly Ser Thr Asn Tyr Asn
65              70                  75                  80

Pro Ser Leu Lys Ser Arg Val Thr Ile Ser Val Asp Thr Ser Lys Asn
                85                  90                  95

Gln Phe Ser Leu Lys Leu Ser Ser Val Thr Ala Ala Asp Thr Ala Val
            100                 105                 110

Tyr Tyr Cys Ala Arg Asp Ser Pro Tyr Tyr Gly Tyr Phe Asp Tyr Trp
        115                 120                 125

Gly Gln Gly Thr Leu Val Thr Val Ser Ser
    130                 135

<210> SEQ ID NO 11
<211> LENGTH: 139
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Met Gly Phe Gly Leu Ser Trp Leu Phe Leu Val Ala Ile Leu Lys Gly
1               5                   10                  15

Val Gln Cys Gln Val Gln Leu Gln Glu Ser Gly Pro Gly Leu Val Lys
            20                  25                  30

Pro Ser Glu Thr Leu Ser Leu Thr Cys Thr Val Ser Gly Gly Ser Val
            35                  40                  45

Ser Ser Gly Ser Tyr Tyr Trp Ser Trp Ile Arg Gln Pro Pro Gly Lys
50                  55                  60

Gly Leu Trp Ile Gly Arg Ile Tyr Tyr Ser Gly Ser Thr Asn Tyr Asn
65                  70                  75                  80

Pro Ser Leu Lys Ser Arg Val Thr Ile Ser Val Asp Thr Ser Lys Asn
                85                  90                  95

Gln Phe Ser Leu Lys Leu Ser Ser Val Thr Ala Ala Asp Thr Ala Val
            100                 105                 110

Tyr Tyr Cys Ala Arg Glu Pro Leu Tyr Asp Ser Ser Gly Phe Gln His
            115                 120                 125

Trp Gly Gln Gly Thr Leu Val Thr Val Ser Ser
        130                 135

<210> SEQ ID NO 12
<211> LENGTH: 128
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Met Gly Thr Pro Ala Gln Leu Leu Phe Leu Leu Leu Leu Trp Leu Pro
1               5                   10                  15

Asp Thr Thr Gly Glu Ile Val Met Thr Gln Ser Pro Ala Thr Leu Ser
            20                  25                  30

Val Ser Pro Gly Glu Arg Ala Thr Leu Ser Cys Arg Ala Ser Gln Ser
            35                  40                  45

Val Ser Ser Asn Leu Ala Trp Tyr Gln Gln Lys Pro Gly Gln Ala Pro
50                  55                  60

Arg Leu Leu Ile Tyr Gly Ala Ser Thr Arg Ala Thr Gly Ile Pro Ala
65                  70                  75                  80

Arg Phe Ser Gly Ser Gly Ser Gly Thr Glu Phe Thr Leu Thr Ile Ser
            85                  90                  95

Ser Leu Gln Ser Glu Asp Phe Ala Val Tyr Tyr Cys Gln Asp Tyr Arg
            100                 105                 110

Ser Trp Pro Arg Arg Ala Phe Gly Gly Gly Thr Lys Val Glu Ile Lys
            115                 120                 125

<210> SEQ ID NO 13
<211> LENGTH: 128
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Met Gly Thr Pro Ala Gln Leu Leu Phe Leu Leu Leu Leu Trp Leu Pro
1               5                   10                  15

Asp Thr Thr Gly Glu Ile Val Met Thr Gln Ser Pro Ala Thr Leu Ser
            20                  25                  30

Val Ser Pro Gly Glu Arg Ala Thr Leu Ser Cys Arg Ala Ser Gln Ser
            35                  40                  45

Val Ser Ser Asn Leu Ala Trp Tyr Gln Gln Lys Pro Gly Gln Ala Pro
    50                  55                  60

Arg Leu Leu Ile Tyr Gly Ala Ser Thr Arg Ala Thr Gly Ile Pro Ala
65                  70                  75                  80

Arg Phe Ser Gly Ser Gly Ser Gly Thr Glu Phe Thr Leu Thr Ile Ser
                85                  90                  95

Ser Leu Gln Ser Glu Asp Phe Ala Val Tyr Tyr Cys Gln Asp Tyr Arg
                100                 105                 110

Thr Trp Pro Arg Arg Ala Phe Gly Gly Gly Thr Lys Val Glu Ile Lys
            115                 120                 125

<210> SEQ ID NO 14
<211> LENGTH: 128
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Met Gly Thr Pro Ala Gln Leu Leu Phe Leu Leu Leu Trp Leu Pro
1               5                   10                  15

Asp Thr Thr Gly Glu Ile Val Met Thr Gln Ser Pro Ala Thr Leu Ser
                20                  25                  30

Val Ser Pro Gly Glu Arg Ala Thr Leu Ser Cys Arg Ala Ser Gln Ser
            35                  40                  45

Val Ser Ser Asn Leu Ala Trp Tyr Gln Gln Lys Pro Gly Gln Ala Pro
    50                  55                  60

Arg Leu Leu Ile Tyr Gly Ala Ser Thr Arg Ala Thr Gly Ile Pro Ala
65                  70                  75                  80

Arg Phe Ser Gly Ser Gly Ser Gly Thr Glu Phe Thr Leu Thr Ile Ser
                85                  90                  95

Ser Leu Gln Ser Glu Asp Phe Ala Val Tyr Tyr Cys Gln Gln Tyr Asn
                100                 105                 110

Asp Trp Pro Arg Trp Thr Phe Gly Gly Gly Thr Lys Val Glu Ile Lys
            115                 120                 125

<210> SEQ ID NO 15
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Met Gly Thr Pro Ala Gln Leu Leu Phe Leu Leu Leu Trp Leu Pro
1               5                   10                  15

Asp Thr Thr Gly Glu Ile Val Leu Thr Gln Ser Pro Ala Thr Leu Ser
                20                  25                  30

Leu Ser Pro Gly Glu Arg Ala Thr Leu Ser Cys Arg Ala Ser Gln Ser
            35                  40                  45

Val Ser Ser Tyr Leu Ala Trp Tyr Gln Gln Lys Pro Gly Ala Pro Arg
    50                  55                  60

Leu Leu Ile Tyr Asp Ala Ser Asn Arg Ala Thr Gly Ile Pro Ala Arg
65                  70                  75                  80

Phe Ser Gly Ser Gly Ser Gly Thr Asp Phe Thr Leu Thr Ile Ser Ser
                85                  90                  95

Leu Glu Pro Glu Asp Phe Ala Val Tyr Tyr Cys Gln Gln Arg Gly Ser
                100                 105                 110

Trp Pro Arg Ile Thr Phe Gly Gly Gly Thr Lys Val Glu Ile Lys
        115                 120                 125

<210> SEQ ID NO 16
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Met Gly Thr Pro Ala Gln Leu Leu Phe Leu Leu Leu Leu Trp Leu Pro
1               5                   10                  15

Asp Thr Thr Gly Glu Ile Val Leu Thr Gln Ser Pro Ala Thr Leu Ser
            20                  25                  30

Leu Ser Pro Gly Glu Arg Ala Thr Leu Ser Cys Arg Ala Ser Gln Ser
        35                  40                  45

Val Ser Ser Tyr Leu Ala Trp Tyr Gln Gln Lys Pro Gly Ala Pro Arg
50                  55                  60

Leu Leu Ile Tyr Asp Ala Ser Asn Arg Ala Thr Gly Ile Pro Ala Arg
65                  70                  75                  80

Phe Ser Gly Ser Gly Ser Gly Thr Asp Phe Thr Leu Thr Ile Ser Ser
                85                  90                  95

Leu Glu Pro Glu Asp Phe Ala Val Tyr Tyr Cys His Gln Arg Gly Thr
            100                 105                 110

Trp Pro Ser Met Thr Phe Gly Gly Gly Thr Lys Val Glu Ile Lys
        115                 120                 125

<210> SEQ ID NO 17
<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Met Gly Thr Pro Ala Gln Leu Leu Phe Leu Leu Leu Leu Trp Leu Pro
1               5                   10                  15

Asp Thr Thr Gly Asp Ile Val Met Thr Gln Ser Pro Asp Ser Leu Ala
            20                  25                  30

Val Ser Leu Gly Glu Arg Ala Thr Ile Asn Cys Lys Ser Ser Gln Ser
        35                  40                  45

Val Leu Tyr Ser Ser Asn Asn Lys Asn Tyr Leu Ala Trp Tyr Gln Gln
50                  55                  60

Lys Pro Gly Gln Pro Pro Lys Leu Leu Ile Tyr Trp Ala Ser Thr Arg
65                  70                  75                  80

Glu Ser Gly Val Pro Asp Arg Phe Ser Gly Ser Gly Ser Gly Thr Asp
                85                  90                  95

Phe Thr Leu Thr Ile Ser Ser Leu Gln Ala Glu Asp Val Ala Val Tyr
            100                 105                 110

Tyr Cys Gln Gln Tyr Tyr Gly Ser Pro Ile Thr Phe Gly Gly Gly Thr
        115                 120                 125

Lys Val Glu Ile Lys
        130

<210> SEQ ID NO 18
<211> LENGTH: 329
<212> TYPE: PRT
<213> ORGANISM: Artificial Sequence
<220> FEATURE:
<223> OTHER INFORMATION: Description of Artificial Sequence: Synthetic
     polypeptide

<400> SEQUENCE: 18

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Thr Cys Leu Val Lys Gly Phe Tyr Pro
                245                 250                 255

Ser Asp Ile Ala Val Glu Trp Glu Ser Asn Gly Gln Pro Glu Asn Asn
            260                 265                 270

Tyr Lys Thr Thr Pro Pro Val Leu Asp Ser Asp Gly Ser Phe Phe Leu
        275                 280                 285

Tyr Ser Lys Leu Thr Val Asp Lys Ser Arg Trp Gln Gln Gly Asn Val
    290                 295                 300

Phe Ser Cys Ser Val Met His Glu Ala Leu His Asn His Tyr Thr Gln
305                 310                 315                 320

Lys Ser Leu Ser Leu Ser Pro Gly Lys
                325

<210> SEQ ID NO 19
<211> LENGTH: 132
<212> TYPE: PRT

<213> ORGANISM: Artificial Sequence
<220> FEATURE:
<223> OTHER INFORMATION: Description of Artificial Sequence: Synthetic polypeptide

<400> SEQUENCE: 19

```
Met Gly Thr Pro Ala Gln Leu Leu Phe Leu Leu Leu Leu Trp Leu Pro
1               5                   10                  15

Asp Thr Thr Gly Asp Ile Val Met Thr Gln Ser Pro Asp Ser Leu Ala
            20                  25                  30

Val Ser Leu Gly Glu Arg Ala Thr Ile Asn Cys Lys Ser Ser Gln Ser
        35                  40                  45

Val Leu Tyr Ser Ser Asn Asn Lys Asn Tyr Leu Ala Trp Tyr Gln Gln
    50                  55                  60

Lys Pro Gly Gln Pro Pro Lys Leu Leu Ile Ser Trp Ala Ser Thr Arg
65                  70                  75                  80

Glu Ser Gly Val Pro Asp Arg Phe Ser Gly Ser Gly Ser Gly Thr Asp
                85                  90                  95

Phe Thr Leu Thr Ile Ser Ser Leu Gln Ala Glu Asp Val Ala Val Tyr
            100                 105                 110

Tyr Cys Gly Gln Phe Tyr Gly Ser Ile Thr Phe Gly Gly Gly Thr Lys
        115                 120                 125

Val Glu Ile Lys
    130
```

<210> SEQ ID NO 20
<211> LENGTH: 127
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 20

```
Met Gly Thr Pro Ala Gln Leu Leu Phe Leu Leu Leu Leu Trp Leu Pro
1               5                   10                  15

Asp Thr Thr Gly Asp Ile Gln Met Thr Gln Ser Pro Ser Thr Leu Ser
            20                  25                  30

Ala Ser Val Gly Asp Arg Val Thr Ile Thr Cys Arg Ala Ser Gln Ser
        35                  40                  45

Ile Ser Ser Trp Leu Ala Trp Tyr Gln Gln Lys Pro Gly Lys Ala Pro
    50                  55                  60

Lys Leu Leu Ile Tyr Asp Ala Ser Ser Leu Glu Ser Gly Val Pro Ser
65                  70                  75                  80

Arg Phe Ser Gly Ser Gly Ser Gly Thr Glu Phe Thr Leu Thr Ile Ser
                85                  90                  95

Ser Leu Gln Pro Asp Asp Phe Ala Thr Tyr Tyr Cys Gln Gln Phe Ala
            100                 105                 110

Ala His Ala Thr Thr Phe Gly Gly Gly Thr Lys Val Glu Ile Lys
        115                 120                 125
```

<210> SEQ ID NO 21
<211> LENGTH: 127
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 21

```
Met Gly Thr Pro Ala Gln Leu Leu Phe Leu Leu Leu Trp Leu Pro
1               5                   10                  15

Asp Thr Thr Gly Asp Ile Gln Met Thr Gln Ser Pro Ser Ser Leu Ser
            20                  25                  30

Ala Ser Val Gly Asp Arg Val Thr Ile Thr Cys Gln Ala Ser Gln Asp
        35                  40                  45

Ile Thr Asn Tyr Leu Asn Trp Tyr Gln Gln Lys Pro Gly Lys Ala Pro
    50                  55                  60

Lys Leu Leu Ile Tyr Asp Ala Ser Asn Leu Glu Thr Gly Val Pro Ser
65                  70                  75                  80

Arg Phe Ser Gly Ser Gly Ser Gly Thr Asp Phe Thr Phe Thr Ile Ser
                85                  90                  95

Ser Leu Gln Pro Glu Asp Ile Ala Thr Tyr Tyr Cys His Gln Tyr Asn
            100                 105                 110

Ala Phe Pro Ile Thr Phe Gly Gly Gly Thr Lys Val Glu Ile Lys
        115                 120                 125
```

<210> SEQ ID NO 22
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

```
Met Gly Thr Pro Ala Gln Leu Leu Phe Leu Leu Leu Trp Leu Pro
1               5                   10                  15

Asp Thr Thr Gly Asp Ile Gln Met Thr Gln Ser Pro Ser Thr Leu Ser
            20                  25                  30

Ala Ser Val Gly Asp Arg Val Thr Ile Thr Cys Arg Ala Ser Gln Ser
        35                  40                  45

Ile Ser Ser Trp Leu Ala Trp Tyr Gln Gln Lys Pro Gly Lys Ala Pro
    50                  55                  60

Lys Leu Leu Ile Tyr Asp Ala Ser Ser Leu Glu Ser Gly Val Pro Ser
65                  70                  75                  80

Arg Phe Ser Gly Ser Gly Ser Gly Thr Glu Phe Thr Leu Thr Ile Ser
                85                  90                  95

Ser Leu Gln Pro Asp Asp Phe Ala Thr Tyr Tyr Cys Gln Gln Tyr Ile
            100                 105                 110

Glu Tyr Ala Thr Thr Phe Gly Gly Gly Thr Lys Val Glu Ile Lys
        115                 120                 125
```

<210> SEQ ID NO 23
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

```
Ser Tyr Gly
1
```

<210> SEQ ID NO 24
<211> LENGTH: 8
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 24

Ile Ser Ala Tyr Asn Gly Asn Thr
1               5

<210> SEQ ID NO 25
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Asp Ser Gly Gly Tyr Gly Ser Gly Ser
1               5

<210> SEQ ID NO 26
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Asp Leu Gly Gly Tyr Gly Ser Gly Ser
1               5

<210> SEQ ID NO 27
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Asp Gly Gly Pro Tyr Gly Phe Gly Pro
1               5

<210> SEQ ID NO 28
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Asp Leu Gly Gly Tyr Gly Ser Gly Gly Val
1               5                   10

<210> SEQ ID NO 29
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Ser Tyr Ala
1
```

```
<210> SEQ ID NO 30
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Ile Ile Pro Ile Phe Gly Thr Ala
1               5

<210> SEQ ID NO 31
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Met Gly Arg Gly Lys Val
1               5

<210> SEQ ID NO 32
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Met Ala Arg Gly Lys Val
1               5

<210> SEQ ID NO 33
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Met Val Arg Gly Lys Val
1               5

<210> SEQ ID NO 34
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Asp Pro Ser Val Asp Leu
1               5

<210> SEQ ID NO 35
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 35

Ser Gly Ser Tyr Tyr
1               5

<210> SEQ ID NO 36
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Ile Tyr Tyr Ser Gly Ser Thr
1               5

<210> SEQ ID NO 37
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Asp Ser Pro Tyr Tyr Gly
1               5

<210> SEQ ID NO 38
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Glu Pro Leu Tyr Asp
1               5

<210> SEQ ID NO 39
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Gln Ser Val Ser Ser Asn
1               5

<210> SEQ ID NO 40
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Gly Ala Ser
1

<210> SEQ ID NO 41
<211> LENGTH: 8
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 41

Gln Asp Tyr Arg Ser Trp Pro Arg
1               5

<210> SEQ ID NO 42
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Gln Asp Tyr Arg Thr Trp Pro Arg
1               5

<210> SEQ ID NO 43
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Gln Gln Tyr Asn Asp Trp Pro Arg
1               5

<210> SEQ ID NO 44
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Gln Ser Val Ser Ser Tyr
1               5

<210> SEQ ID NO 45
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Asp Ala Ser
1

<210> SEQ ID NO 46
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Gln Gln Arg Gly Ser Trp Pro Arg
1               5
```

<210> SEQ ID NO 47
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

His Gln Arg Gly Thr Trp Pro Ser
1               5

<210> SEQ ID NO 48
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Gln Ser Ile Ser Ser Trp
1               5

<210> SEQ ID NO 49
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Gln Gln Phe Ala Ala His Ala
1               5

<210> SEQ ID NO 50
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Gln Asp Ile Thr Asn Tyr
1               5

<210> SEQ ID NO 51
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

His Gln Tyr Asn Ala Phe Pro
1               5

<210> SEQ ID NO 52
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide -continued

```
<400> SEQUENCE: 52

Gln Gln Tyr Ile Glu Tyr Ala
1               5

<210> SEQ ID NO 53
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Gln Ser Val Leu Tyr Ser Ser Asn Asn Lys Asn Tyr
1               5                   10

<210> SEQ ID NO 54
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Trp Ala Ser
1

<210> SEQ ID NO 55
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Gln Gln Tyr Tyr Gly Ser Pro
1               5

<210> SEQ ID NO 56
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Gly Gln Phe Tyr Gly Ser
1               5

<210> SEQ ID NO 57
<211> LENGTH: 1210
<212> TYPE: PRT
<213> ORGANISM: Homo sapiens

<400> SEQUENCE: 57

Met Arg Pro Ser Gly Thr Ala Gly Ala Ala Leu Leu Ala Leu Leu Ala
1               5                   10                  15

Ala Leu Cys Pro Ala Ser Arg Ala Leu Glu Glu Lys Lys Val Cys Gln
                20                  25                  30

Gly Thr Ser Asn Lys Leu Thr Gln Leu Gly Thr Phe Glu Asp His Phe
            35                  40                  45
```

-continued

```
Leu Ser Leu Gln Arg Met Phe Asn Asn Cys Glu Val Val Leu Gly Asn
 50                  55                  60

Leu Glu Ile Thr Tyr Val Gln Arg Asn Tyr Asp Leu Ser Phe Leu Lys
 65                      70                  75                  80

Thr Ile Gln Glu Val Ala Gly Tyr Val Leu Ile Ala Leu Asn Thr Val
                     85                  90                  95

Glu Arg Ile Pro Leu Glu Asn Leu Gln Ile Ile Arg Gly Asn Met Tyr
                100                 105                 110

Tyr Glu Asn Ser Tyr Ala Leu Ala Val Leu Ser Asn Tyr Asp Ala Asn
            115                 120                 125

Lys Thr Gly Leu Lys Glu Leu Pro Met Arg Asn Leu Gln Glu Ile Leu
130                 135                 140

His Gly Ala Val Arg Phe Ser Asn Asn Pro Ala Leu Cys Asn Val Glu
145                     150                 155                 160

Ser Ile Gln Trp Arg Asp Ile Val Ser Ser Asp Phe Leu Ser Asn Met
                165                 170                 175

Ser Met Asp Phe Gln Asn His Leu Gly Ser Cys Gln Lys Cys Asp Pro
            180                 185                 190

Ser Cys Pro Asn Gly Ser Cys Trp Gly Ala Gly Glu Glu Asn Cys Gln
            195                 200                 205

Lys Leu Thr Lys Ile Ile Cys Ala Gln Gln Cys Ser Gly Arg Cys Arg
210                 215                 220

Gly Lys Ser Pro Ser Asp Cys Cys His Asn Gln Cys Ala Ala Gly Cys
225                 230                 235                 240

Thr Gly Pro Arg Glu Ser Asp Cys Leu Val Cys Arg Lys Phe Arg Asp
                245                 250                 255

Glu Ala Thr Cys Lys Asp Thr Cys Pro Pro Leu Met Leu Tyr Asn Pro
            260                 265                 270

Thr Thr Tyr Gln Met Asp Val Asn Pro Glu Gly Lys Tyr Ser Phe Gly
        275                 280                 285

Ala Thr Cys Val Lys Lys Cys Pro Arg Asn Tyr Val Val Thr Asp His
290                 295                 300

Gly Ser Cys Val Arg Ala Cys Gly Ala Asp Ser Tyr Glu Met Glu Glu
305                 310                 315                 320

Asp Gly Val Arg Lys Cys Lys Lys Cys Glu Gly Pro Cys Arg Lys Val
                325                 330                 335

Cys Asn Gly Ile Gly Ile Gly Glu Phe Lys Asp Ser Leu Ser Ile Asn
            340                 345                 350

Ala Thr Asn Ile Lys His Phe Lys Asn Cys Thr Ser Ile Ser Gly Asp
            355                 360                 365

Leu His Ile Leu Pro Val Ala Phe Arg Gly Asp Ser Phe Thr His Thr
370                 375                 380

Pro Pro Leu Asp Pro Gln Glu Leu Asp Ile Leu Lys Thr Val Lys Glu
385                 390                 395                 400

Ile Thr Gly Phe Leu Leu Ile Gln Ala Trp Pro Glu Asn Arg Thr Asp
                405                 410                 415

Leu His Ala Phe Glu Asn Leu Glu Ile Ile Arg Gly Arg Thr Lys Gln
            420                 425                 430

His Gly Gln Phe Ser Leu Ala Val Val Ser Leu Asn Ile Thr Ser Leu
        435                 440                 445

Gly Leu Arg Ser Leu Lys Glu Ile Ser Asp Gly Asp Val Ile Ile Ser
450                 455                 460

Gly Asn Lys Asn Leu Cys Tyr Ala Asn Thr Ile Asn Trp Lys Lys Leu
```

```
                465                 470                 475                 480
            Phe Gly Thr Ser Gly Gln Lys Thr Lys Ile Ile Ser Asn Arg Gly Glu
                            485                 490                 495
            Asn Ser Cys Lys Ala Thr Gly Gln Val Cys His Ala Leu Cys Ser Pro
                        500                 505                 510
            Glu Gly Cys Trp Gly Pro Glu Pro Arg Asp Cys Val Ser Cys Arg Asn
                        515                 520                 525
            Val Ser Arg Gly Arg Glu Cys Val Asp Lys Cys Asn Leu Leu Glu Gly
                        530                 535                 540
            Glu Pro Arg Glu Phe Val Glu Asn Ser Glu Cys Ile Gln Cys His Pro
            545                 550                 555                 560
            Glu Cys Leu Pro Gln Ala Met Asn Ile Thr Cys Thr Gly Arg Gly Pro
                            565                 570                 575
            Asp Asn Cys Ile Gln Cys Ala His Tyr Ile Asp Gly Pro His Cys Val
                        580                 585                 590
            Lys Thr Cys Pro Ala Gly Val Met Gly Glu Asn Asn Thr Leu Val Trp
                        595                 600                 605
            Lys Tyr Ala Asp Ala Gly His Val Cys His Leu Cys His Pro Asn Cys
                        610                 615                 620
            Thr Tyr Gly Cys Thr Gly Pro Gly Leu Glu Gly Cys Pro Thr Asn Gly
            625                 630                 635                 640
            Pro Lys Ile Pro Ser Ile Ala Thr Gly Met Val Gly Ala Leu Leu Leu
                            645                 650                 655
            Leu Leu Val Val Ala Leu Gly Ile Gly Leu Phe Met Arg Arg Arg His
                        660                 665                 670
            Ile Val Arg Lys Arg Thr Leu Arg Arg Leu Leu Gln Glu Arg Glu Leu
                        675                 680                 685
            Val Glu Pro Leu Thr Pro Ser Gly Glu Ala Pro Asn Gln Ala Leu Leu
                        690                 695                 700
            Arg Ile Leu Lys Glu Thr Glu Phe Lys Lys Ile Lys Val Leu Gly Ser
            705                 710                 715                 720
            Gly Ala Phe Gly Thr Val Tyr Lys Gly Leu Trp Ile Pro Glu Gly Glu
                            725                 730                 735
            Lys Val Lys Ile Pro Val Ala Ile Lys Glu Leu Arg Glu Ala Thr Ser
                        740                 745                 750
            Pro Lys Ala Asn Lys Glu Ile Leu Asp Glu Ala Tyr Val Met Ala Ser
                        755                 760                 765
            Val Asp Asn Pro His Val Cys Arg Leu Leu Gly Ile Cys Leu Thr Ser
                        770                 775                 780
            Thr Val Gln Leu Ile Thr Gln Leu Met Pro Phe Gly Cys Leu Leu Asp
            785                 790                 795                 800
            Tyr Val Arg Glu His Lys Asp Asn Ile Gly Ser Gln Tyr Leu Leu Asn
                            805                 810                 815
            Trp Cys Val Gln Ile Ala Lys Gly Met Asn Tyr Leu Glu Asp Arg Arg
                        820                 825                 830
            Leu Val His Arg Asp Leu Ala Ala Arg Asn Val Leu Val Lys Thr Pro
                        835                 840                 845
            Gln His Val Lys Ile Thr Asp Phe Gly Leu Ala Lys Leu Leu Phe Ala
                        850                 855                 860
            Glu Glu Lys Glu Tyr His Ala Glu Phe Phe Lys Cys Pro Ile Lys Trp
            865                 870                 875                 880
            Met Ala Leu Glu Ser Ile Leu His Arg Ile Tyr Thr His Gln Ser Asp
                            885                 890                 895
```

Val Trp Ser Tyr Gly Val Thr Val Trp Glu Leu Met Thr Phe Gly Ser
            900                 905                 910

Lys Pro Tyr Asp Gly Ile Pro Ala Ser Glu Ile Ser Ser Ile Leu Glu
        915                 920                 925

Lys Gly Glu Arg Leu Pro Gln Pro Pro Ile Cys Thr Ile Asp Val Tyr
    930                 935                 940

Met Ile Met Val Lys Cys Trp Met Ile Asp Ala Asp Ser Arg Pro Lys
945                 950                 955                 960

Phe Arg Glu Leu Ile Ile Glu Phe Ser Lys Met Ala Arg Asp Pro Gln
                965                 970                 975

Arg Tyr Leu Val Ile Gln Gly Asp Glu Arg Met His Leu Pro Ser Pro
            980                 985                 990

Thr Asp Ser Asn Phe Tyr Arg Ala Leu Met Asp Glu Glu Asp Met Asp
        995                 1000                1005

Asp Val Val Asp Ala Asp Glu Tyr Leu Ile Pro Gln Gln Gly Phe
    1010                1015                1020

Phe Ser Ser Pro Ser Thr Ser Arg Thr Pro Leu Leu Ser Ser Leu
    1025                1030                1035

Ser Ala Thr Ser Asn Asn Ser Thr Val Ala Cys Ile Asp Arg Asn
    1040                1045                1050

Gly Leu Gln Ser Cys Pro Ile Lys Glu Asp Ser Phe Leu Gln Arg
    1055                1060                1065

Tyr Ser Ser Asp Pro Thr Gly Ala Leu Thr Glu Asp Ser Ile Asp
    1070                1075                1080

Asp Thr Phe Leu Pro Val Pro Glu Tyr Ile Asn Gln Ser Val Pro
    1085                1090                1095

Lys Arg Pro Ala Gly Ser Val Gln Asn Pro Val Tyr His Asn Gln
    1100                1105                1110

Pro Leu Asn Pro Ala Pro Ser Arg Asp Pro His Tyr Gln Asp Pro
    1115                1120                1125

His Ser Thr Ala Val Gly Asn Pro Glu Leu Tyr Asn Thr Val Gln
    1130                1135                1140

Pro Thr Cys Val Asn Ser Thr Phe Asp Ser Pro Ala His Trp Ala
    1145                1150                1155

Gln Lys Gly Ser His Gln Ile Ser Leu Asp Asn Pro Asp Tyr Gln
    1160                1165                1170

Gln Asp Phe Phe Pro Lys Glu Ala Lys Pro Asn Gly Ile Phe Lys
    1175                1180                1185

Gly Ser Thr Ala Glu Asn Ala Glu Tyr Leu Arg Val Ala Pro Gln
    1190                1195                1200

Ser Ser Glu Phe Ile Gly Ala
    1205                1210

<210> SEQ ID NO 58
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 58

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr

```
            20                  25                  30

Gly Ile Ser Trp Val Arg Gln Ala Pro Gly Gln Gly Leu Glu Trp Met
            35                  40                  45

Gly Trp Ile Ser Ala Tyr Asn Gly Asn Thr Asn Tyr Ala Gln Lys Leu
        50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asn Trp Phe Asp Pro Trp Gly Gln Gly Thr Leu Val Thr Val
                100                 105                 110

Ser Ser

<210> SEQ ID NO 59
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Met Gly Phe Gly Leu Ser Trp Leu Phe Leu Val Ala Ile Leu Lys Gly
1               5                   10                  15

Val Gln Cys Gln
            20

<210> SEQ ID NO 60
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 60

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
            35                  40                  45

Gly Gly Ile Ile Pro Ile Phe Gly Thr Ala Asn Tyr Ala Gln Lys Phe
        50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ala Phe Asp Ile Trp Gly Gln Gly Thr Met Val Thr Val Ser
                100                 105                 110

Ser

<210> SEQ ID NO 61
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide
```

-continued

```
<400> SEQUENCE: 61

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Tyr Trp Tyr Phe Asp Leu Trp Gly Arg Gly Thr Leu Val Thr
            100                 105                 110

Val Ser Ser
        115

<210> SEQ ID NO 62
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 62

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Val Ser Ser Gly
            20                  25                  30

Ser Tyr Tyr Trp Ser Trp Ile Arg Gln Pro Pro Gly Lys Gly Leu Trp
        35                  40                  45

Ile Gly Tyr Ile Tyr Tyr Ser Gly Ser Thr Asn Tyr Asn Pro Ser Leu
    50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Tyr Phe Asp Tyr Trp Gly Gln Gly Thr Leu Val Thr Val Ser
            100                 105                 110

Ser

<210> SEQ ID NO 63
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 63

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Val Ser Ser Gly
            20                  25                  30

Ser Tyr Tyr Trp Ser Trp Ile Arg Gln Pro Pro Gly Lys Gly Leu Trp
        35                  40                  45
```

```
Ile Gly Tyr Ile Tyr Tyr Ser Gly Ser Thr Asn Tyr Asn Pro Ser Leu
        50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Ala Glu Tyr Phe Gln His Trp Gly Gln Gly Thr Leu Val Thr
            100                 105                 110

Val Ser Ser
        115

<210> SEQ ID NO 64
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 64

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro Leu
                85                  90                  95

Thr Phe Gly Gly Gly Thr Lys Val Glu Ile Lys
                100                 105

<210> SEQ ID NO 65
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 65

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
                100                 105
```

<210> SEQ ID NO 66
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Met Gly Thr Pro Ala Gln Leu Leu Phe Leu Leu Leu Leu Trp Leu Pro
1               5                   10                  15

Asp Thr Thr Gly
            20

<210> SEQ ID NO 67
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 67

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Ser Tyr Ser Leu
                85                  90                  95

Thr Phe Gly Gly Gly Thr Lys Val Glu Ile Lys
            100                 105

<210> SEQ ID NO 68
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 68

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Tyr Asp Asn Leu Pro Leu
                85                  90                  95

```
<210> SEQ ID NO 69
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 69

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Ala Pro Arg Leu Leu Ile Tyr
        35                  40                  45

Asp Ala Ser Asn Arg Ala Thr Gly Ile Pro Ala Arg Phe Ser Gly Ser
    50                  55                  60

Gly Ser Gly Thr Asp Phe Thr Leu Thr Ile Ser Ser Leu Glu Pro Glu
65                  70                  75                  80

Asp Phe Ala Val Tyr Tyr Cys Gln Gln Arg Ser Asn Trp Pro Leu Thr
                85                  90                  95

Phe Gly Gly Gly Thr Lys Val Glu Ile Lys
            100                 105

<210> SEQ ID NO 70
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 70

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Thr Pro Leu Thr Phe Gly Gly Gly Thr Lys Val Glu Ile
            100                 105                 110

Lys
```